United States Patent
Campagna

(10) Patent No.: US 11,786,188 B2
(45) Date of Patent: *Oct. 17, 2023

(54) ARTICULATING PATIENT POSITIONING APPARATUS

(71) Applicant: Michael Campagna, Naperville, IL (US)

(72) Inventor: Michael Campagna, Naperville, IL (US)

(*) Notice: Subject to any disclaimer, the term of this patent is extended or adjusted under 35 U.S.C. 154(b) by 658 days.

This patent is subject to a terminal disclaimer.

(21) Appl. No.: 16/900,509

(22) Filed: Jun. 12, 2020

(65) Prior Publication Data

US 2020/0375552 A1   Dec. 3, 2020

Related U.S. Application Data

(63) Continuation of application No. 13/902,939, filed on May 27, 2013, now Pat. No. 10,820,866, which is a
(Continued)

(51) Int. Cl.
*A61B 6/04* (2006.01)
*A61B 6/03* (2006.01)
(Continued)

(52) U.S. Cl.
CPC ............ *A61B 6/0442* (2013.01); *A61B 5/055* (2013.01); *A61B 6/032* (2013.01); *A61B 6/0487* (2020.08);
(Continued)

(58) Field of Classification Search
CPC ....... A61B 6/04; A61B 6/0442; A61B 6/0487; A61G 7/07; A61G 7/072; A61G 7/0755; A61G 7/075; A61G 7/065; A61G 7/0506; A61G 13/121; A61G 13/124; A61G 13/125; A61G 13/1235; A61G 13/1205; A61G 13/1245; B66D 1/12; B66D 1/26;
(Continued)

(56) References Cited

U.S. PATENT DOCUMENTS

| 5,569,099 A * | 10/1996 | Jackson ................. A63B 53/10 473/319 |
| 6,378,149 B1 * | 4/2002 | Sanders ................. A61G 13/12 5/624 |
| 2011/0224585 A1 * | 9/2011 | Hall ....................... A61H 1/008 601/34 |

* cited by examiner

Primary Examiner — Camtu T Nguyen
(74) Attorney, Agent, or Firm — AddyHart P.C.

(57) ABSTRACT

An apparatus comprises means for engaging a patient platform. The means comprises at least one layer of laminar sheeting of radiolucent material. At least one anatomical support member which comprises at least one layer of laminar sheeting of radiolucent material. At least one articulating joint unit is in engagement with the at least one of anatomical support member. The at least one articulating joint unit comprise at least one layer of laminar sheeting of radiolucent material with a primarily non-metallic connector at a central pivot point. The at least one articulating joint unit is positionable in at least a vertical and horizontal orientations enabling positioning of portions of an anatomy in three dimensions along x, y, and z axes. At least one primarily non-metallic locking member is configured to lock the at least one articulating joint unit at selectable position(s), in which a load bearing stress is spread across lengths of the laminar sheeting to mitigate a susceptibility to stress fractures and load failure.

13 Claims, 52 Drawing Sheets

Related U.S. Application Data continuation-in-part of application No. 13/251,985, filed on Oct. 3, 2011, now Pat. No. 11,076,817, and a continuation-in-part of application No. 12/464,456, filed on May 12, 2009, now Pat. No. 8,510,882, and a continuation-in-part of application No. 12/684,934, filed on Jan. 9, 2010, now Pat. No. 8,544,471.

(60) Provisional application No. 61/682,279, filed on Aug. 12, 2012.

(51) Int. Cl.
- *A61B 6/00* (2006.01)
- *A61G 13/04* (2006.01)
- *A61G 13/08* (2006.01)
- *A61B 5/055* (2006.01)

(52) U.S. Cl.
CPC ............ *A61B 6/4085* (2013.01); *A61G 13/04* (2013.01); *A61G 13/08* (2013.01)

(58) Field of Classification Search
CPC .... B66D 1/36; B66D 1/46; B66D 1/60; A61F 5/3761; A61F 5/37
See application file for complete search history.

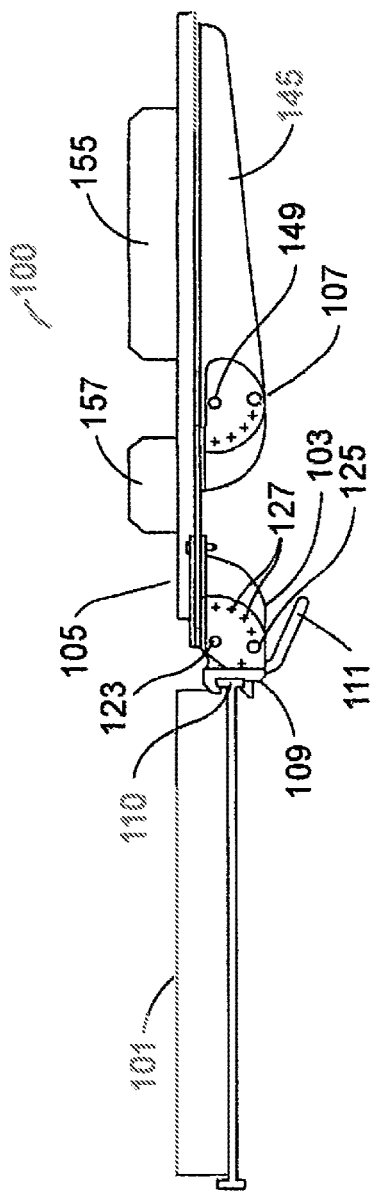
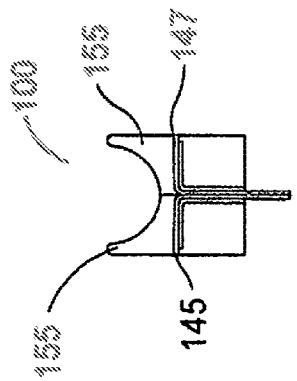
FIG. 1A
FIG. 1B

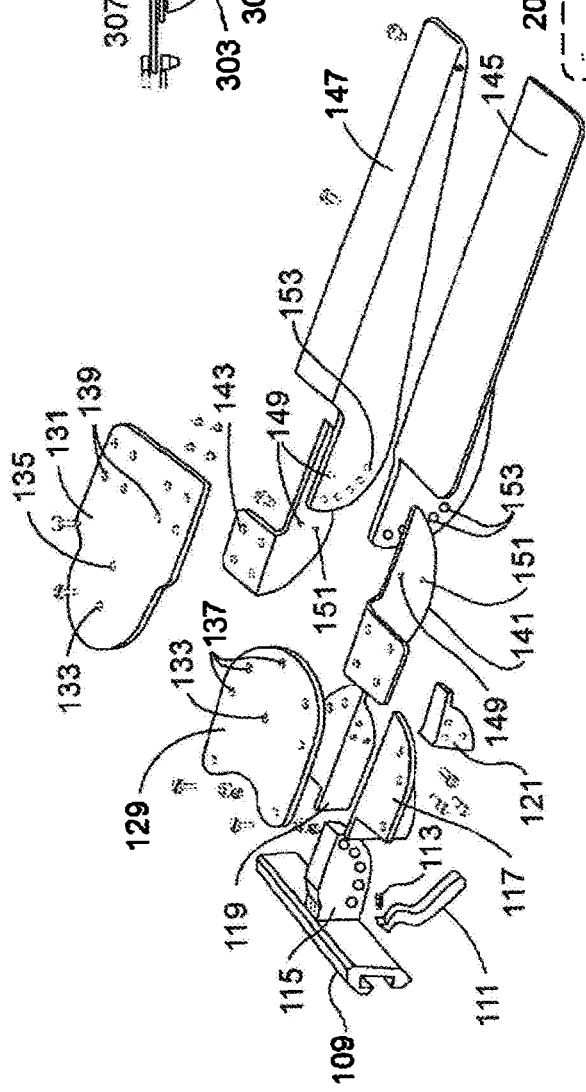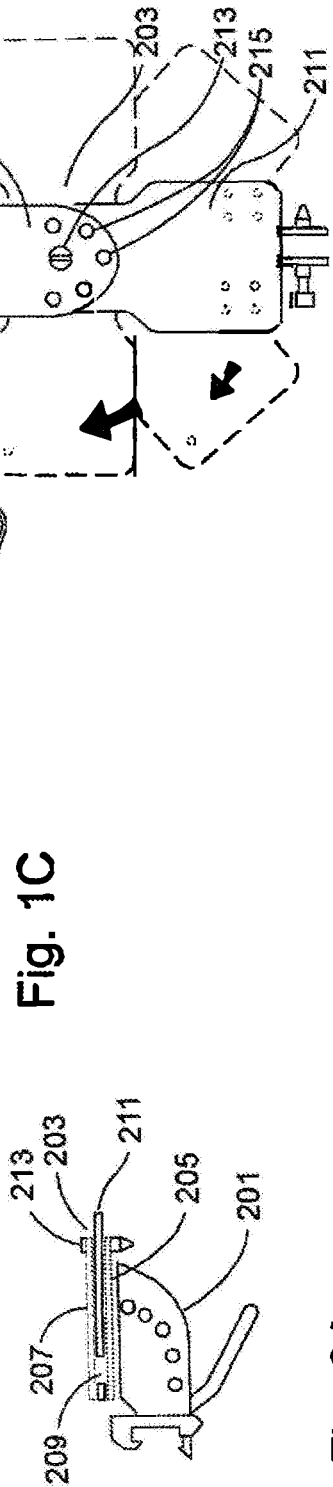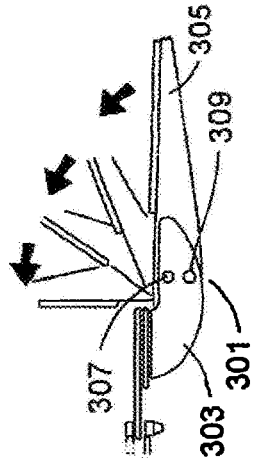

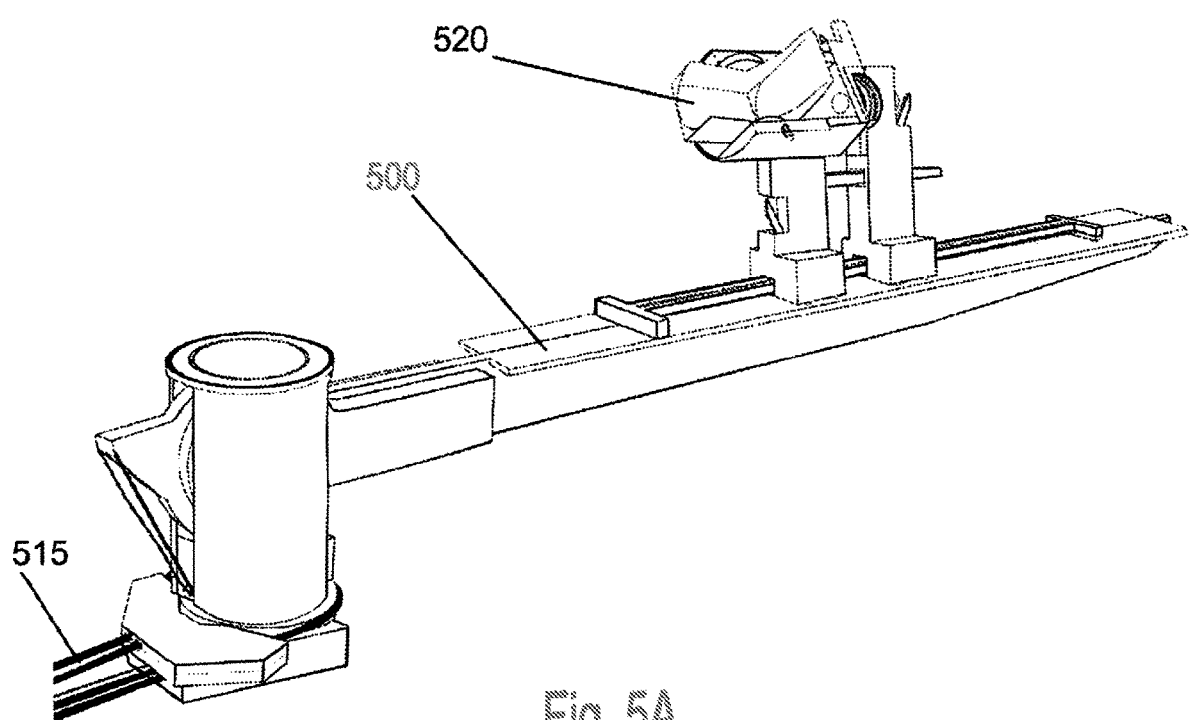

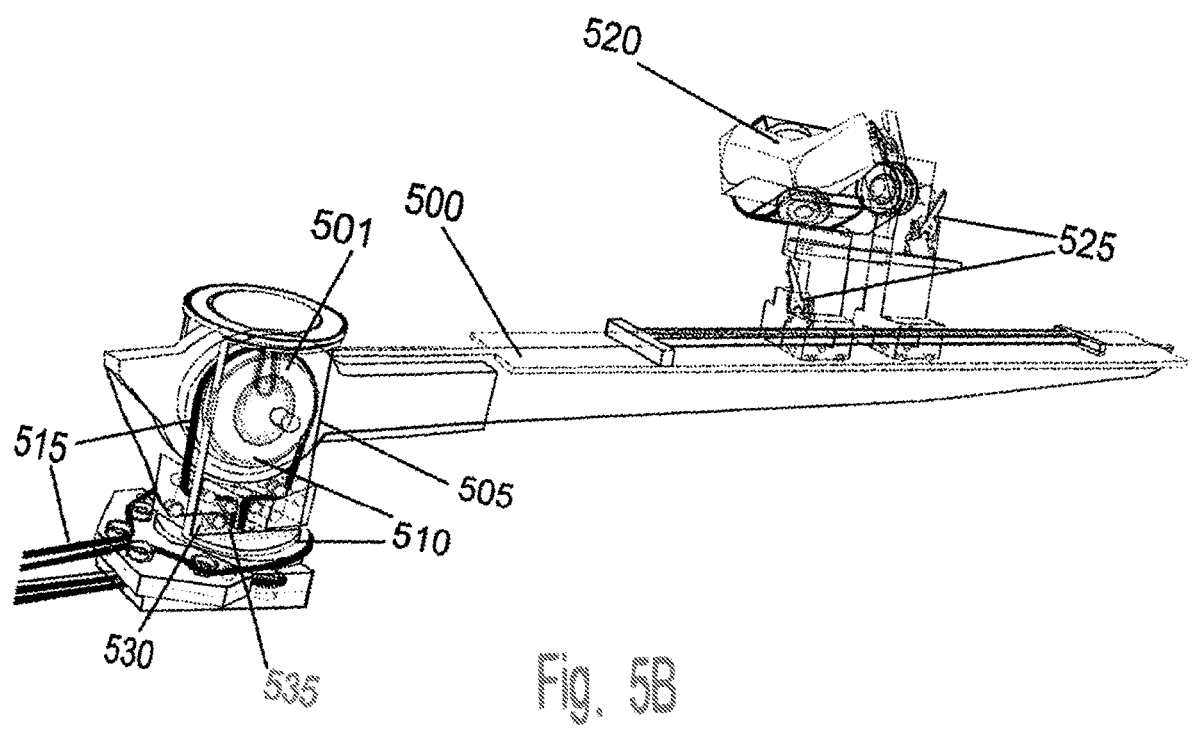

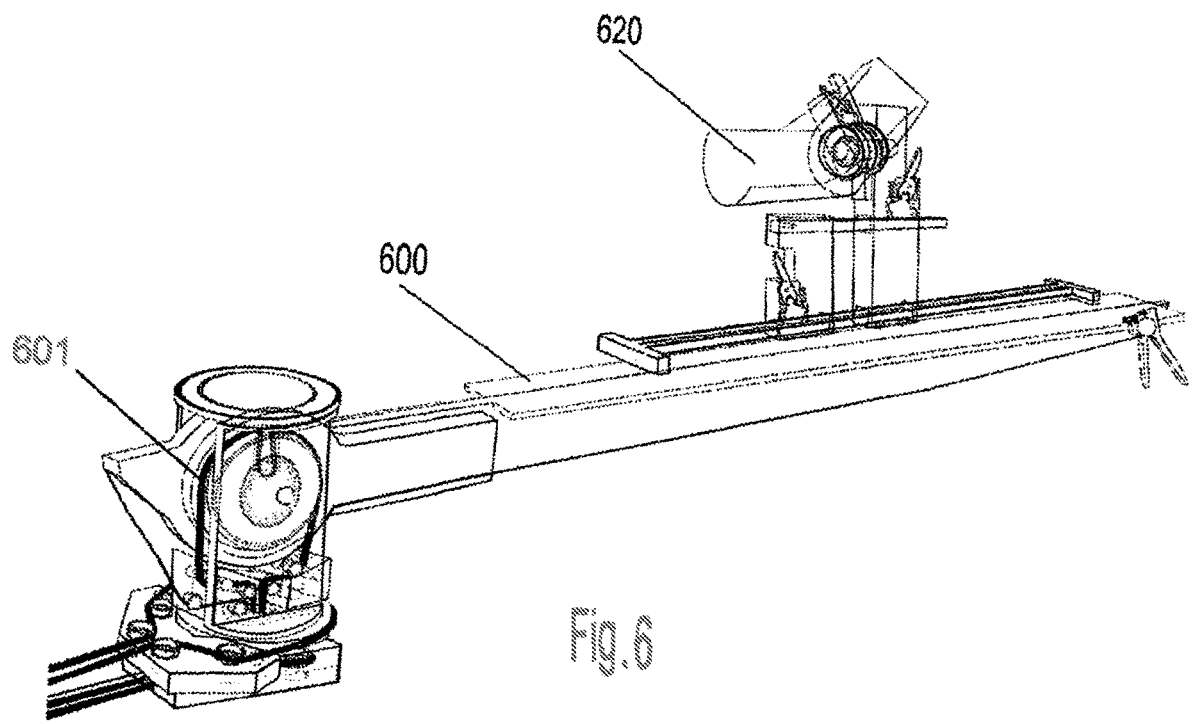

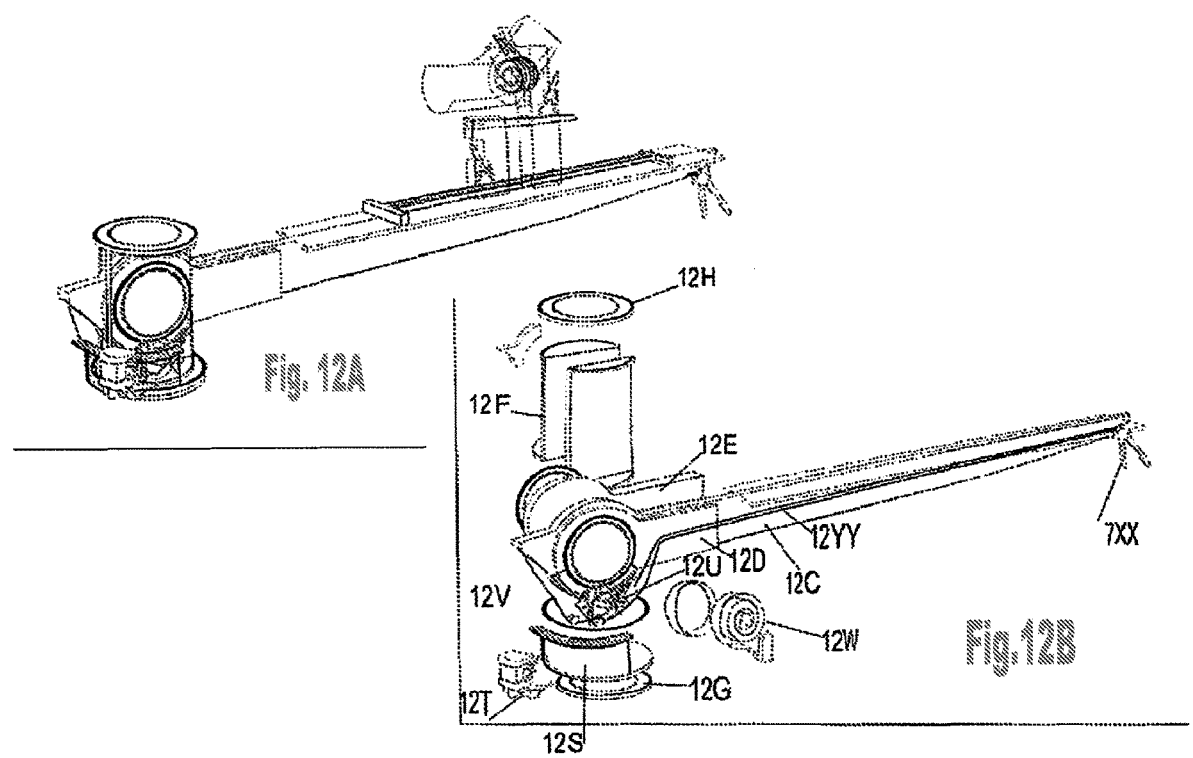

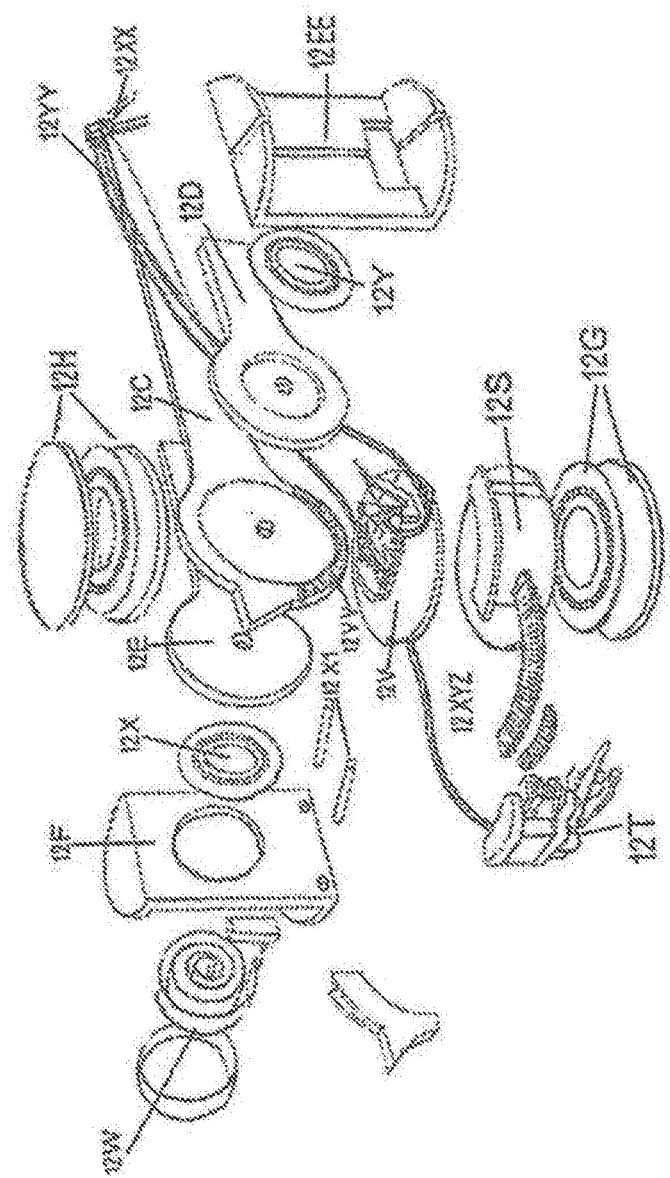

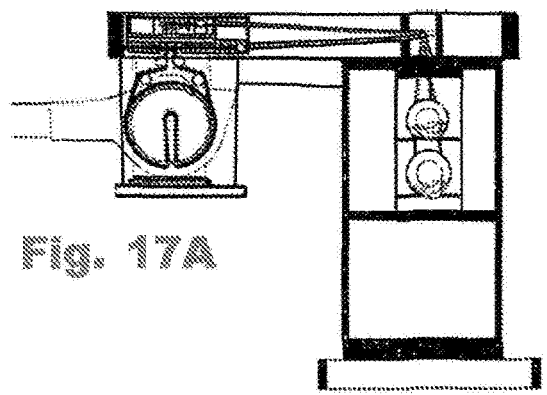
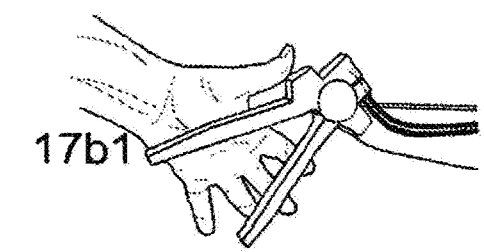
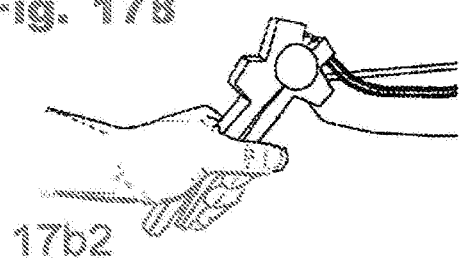
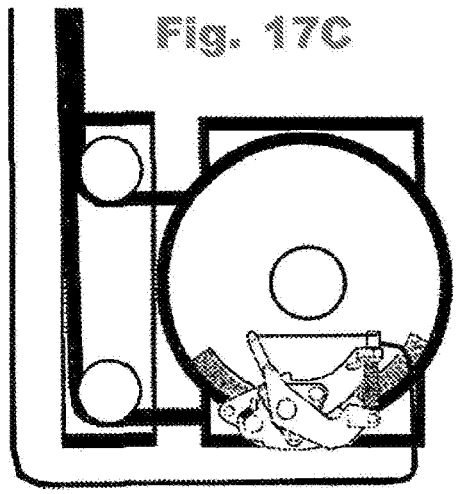
Fig. 17

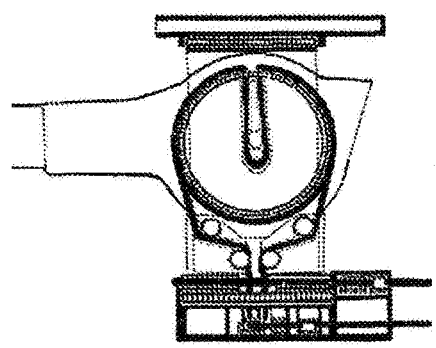
Fig. 18A
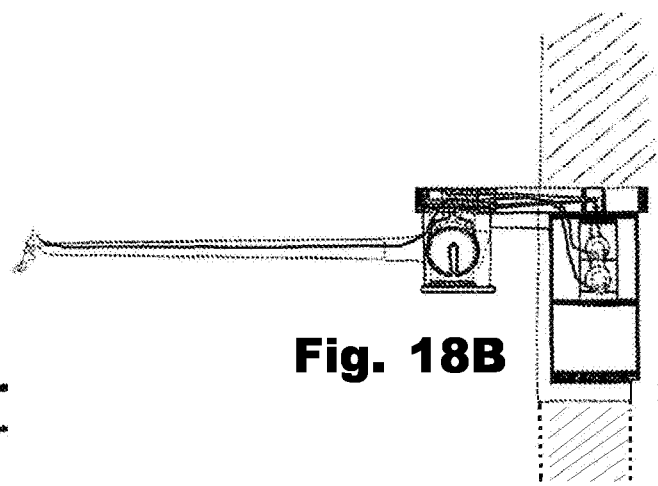
Fig. 18B
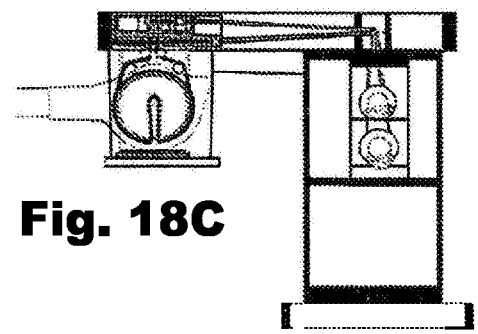
Fig. 18C
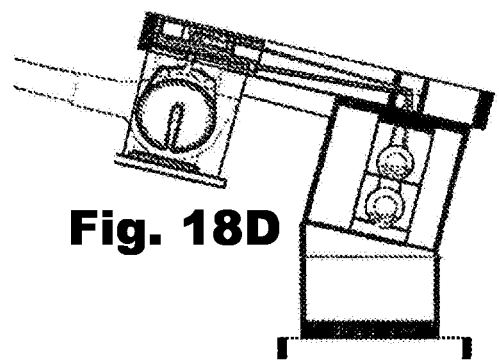
Fig. 18D
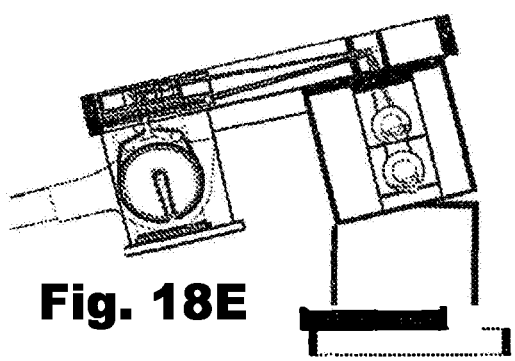
Fig. 18E
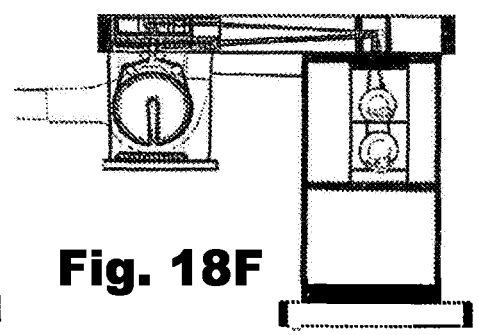
Fig. 18F
Fig. 18

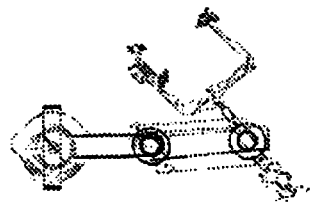
Fig. 19C1
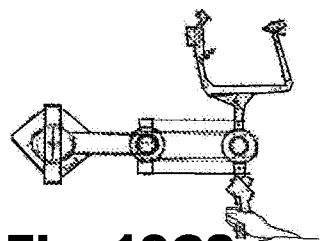
Fig. 19C2
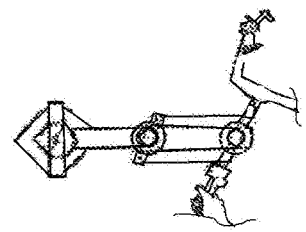
Fig. 19C3
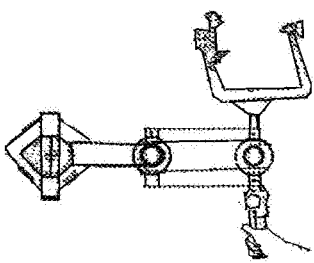
Fig. 19C4
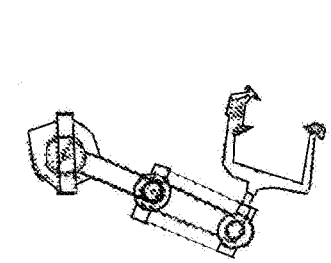
Fig. 19C5
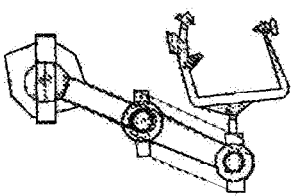
Fig. 19C6
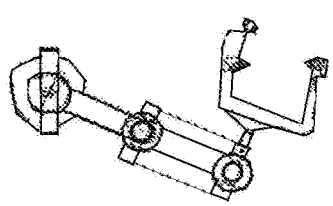
Fig. 19C7
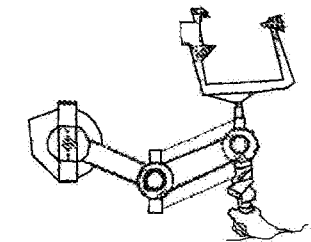
Fig. 19C8
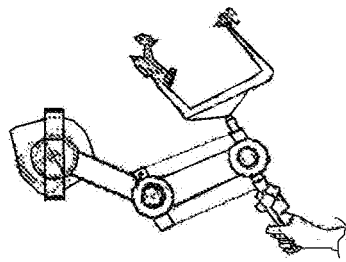
Fig. 19C9
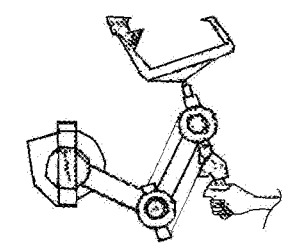
Fig. 19C10
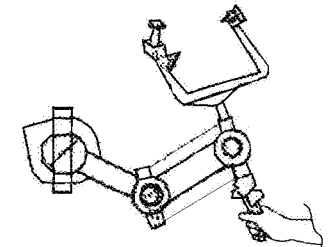
Fig. 19C11
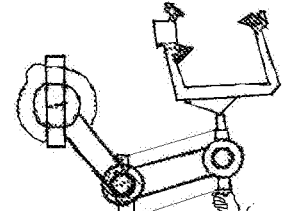
Fig. 19C12
Fig. 19C

 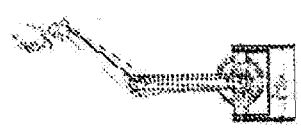 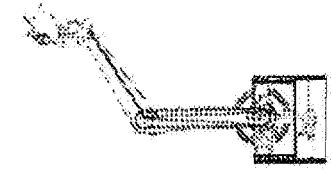
Fig. 21A1　　Fig. 21A2　　Fig. 21A3
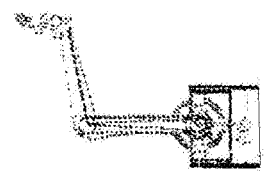 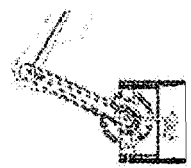 
Fig. 21A4　　Fig. 21A5　　Fig. 21A6
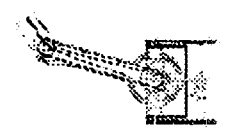  
Fig. 21A7　　Fig. 21A8　　Fig. 21A9
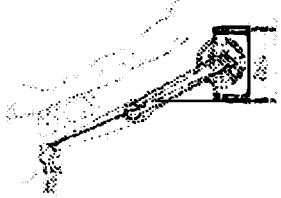 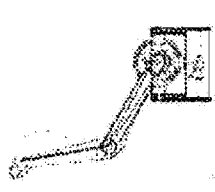 
Fig. 21A10　　Fig. 21A11　　Fig. 21A12

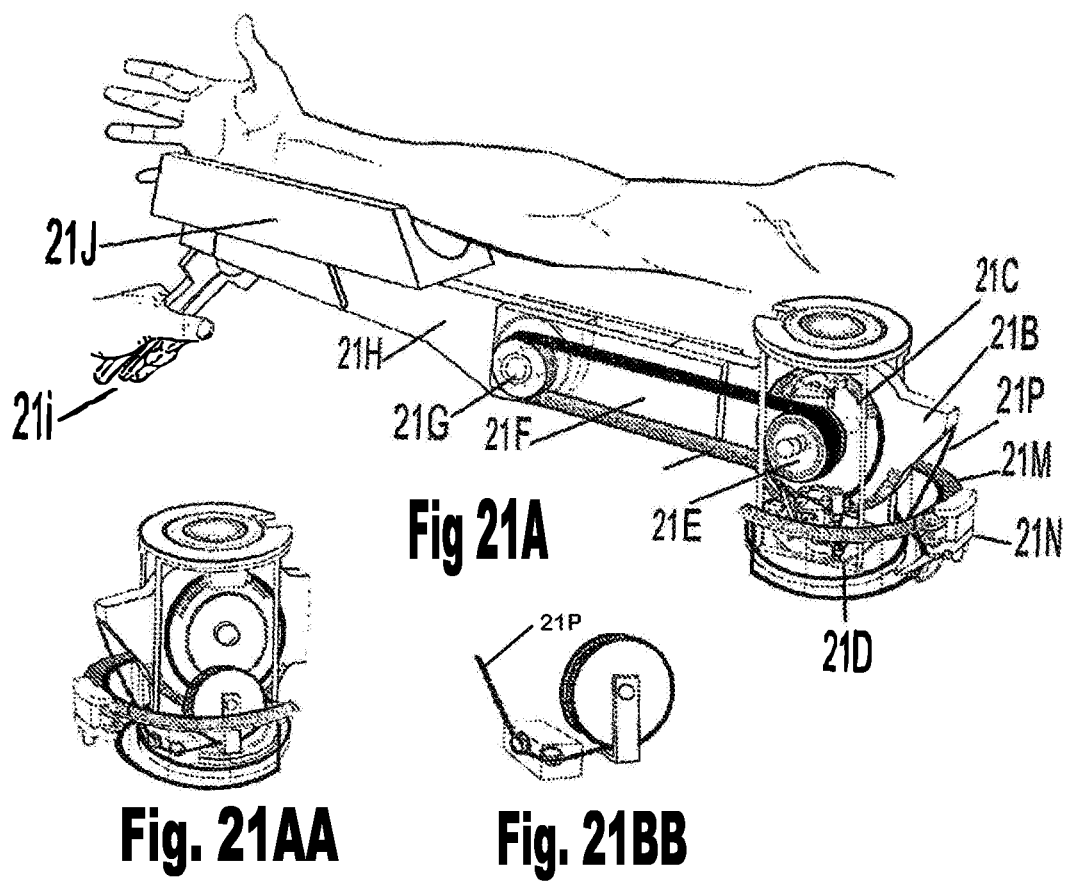

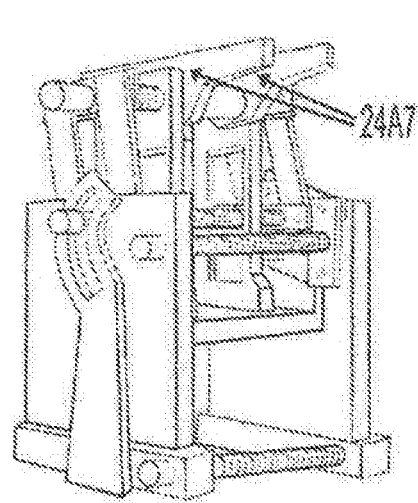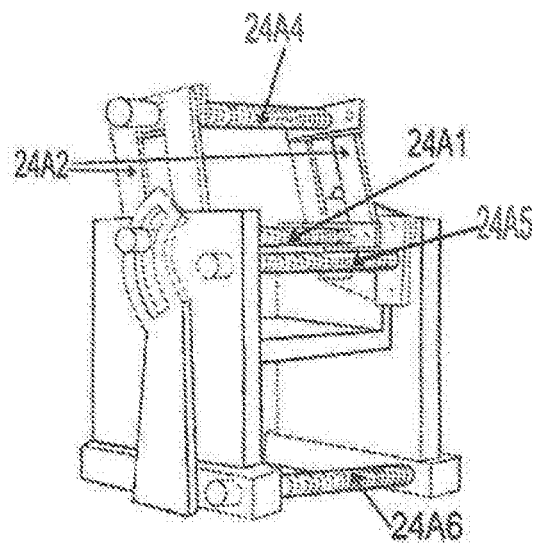
Fig. 24A   Fig. 24AA

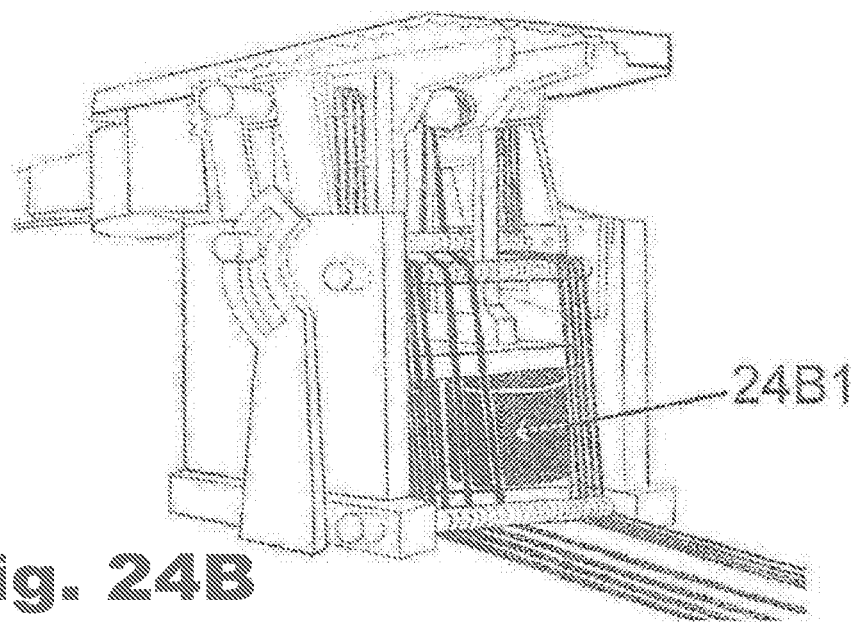
Fig. 24B
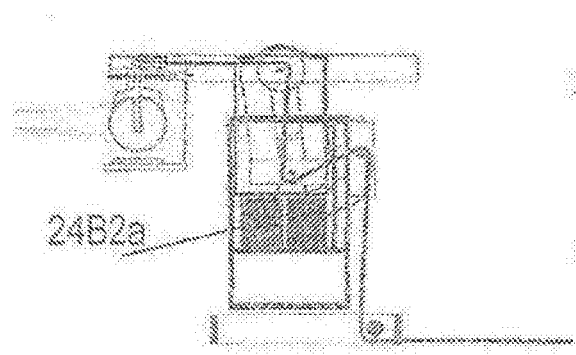
Fig. 24B2
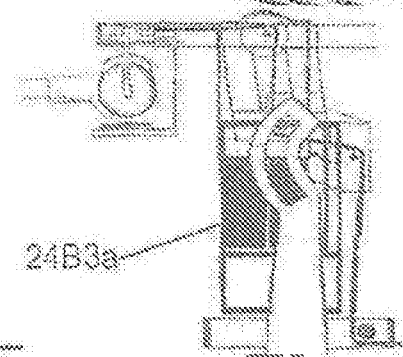
Fig. 24B3
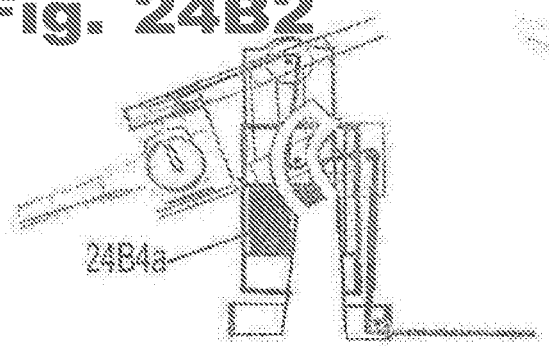
Fig. 24B4
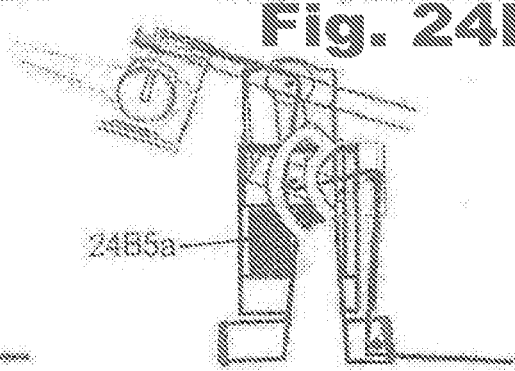
Fig. 24B5

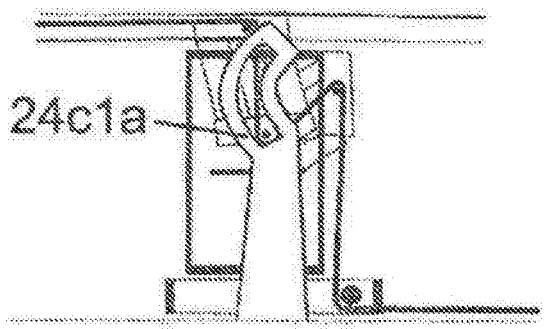
Fig. 24C1
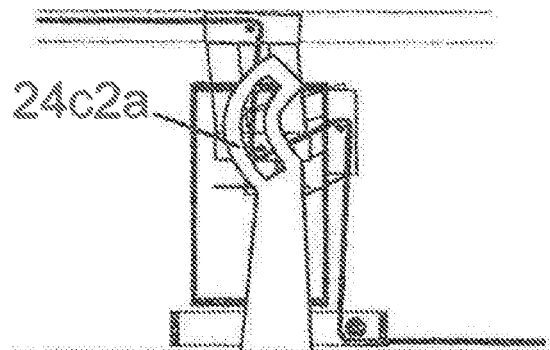
Fig. 24C2
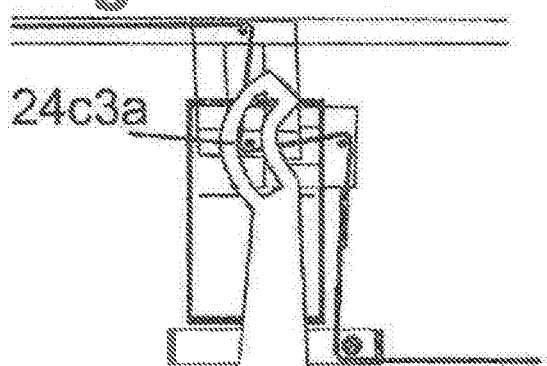
Fig. 24C3
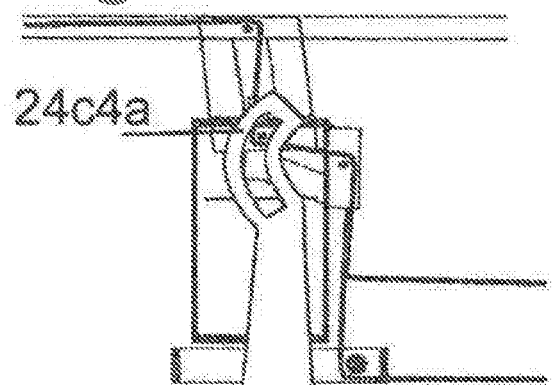
Fig. 24C4
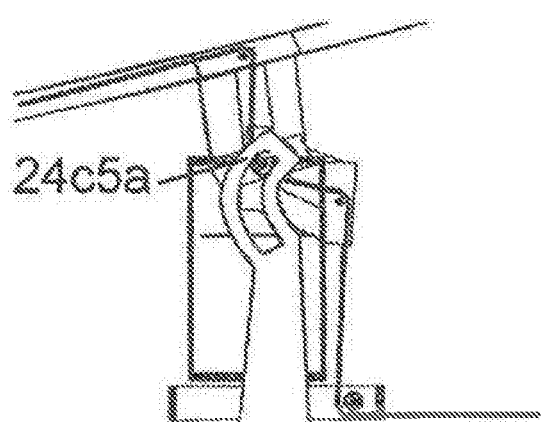
Fig. 24C5
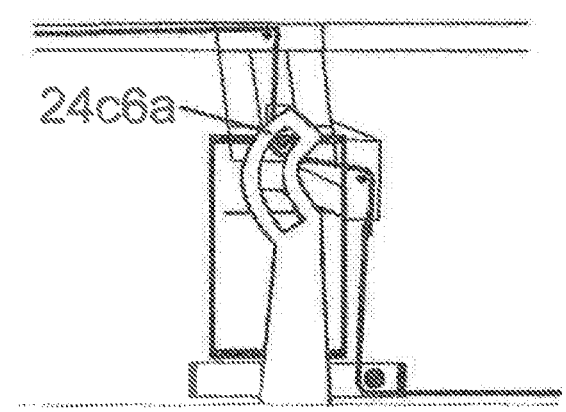
Fig. 24C6
Fig. 24C

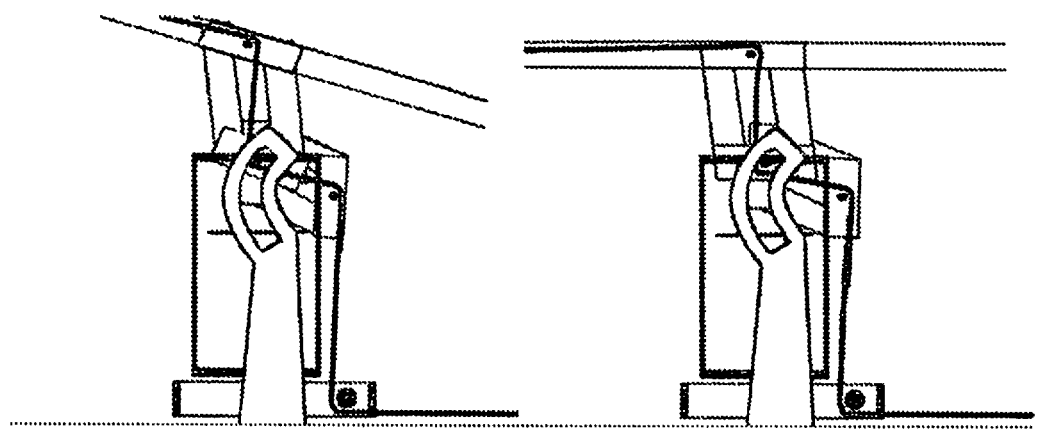
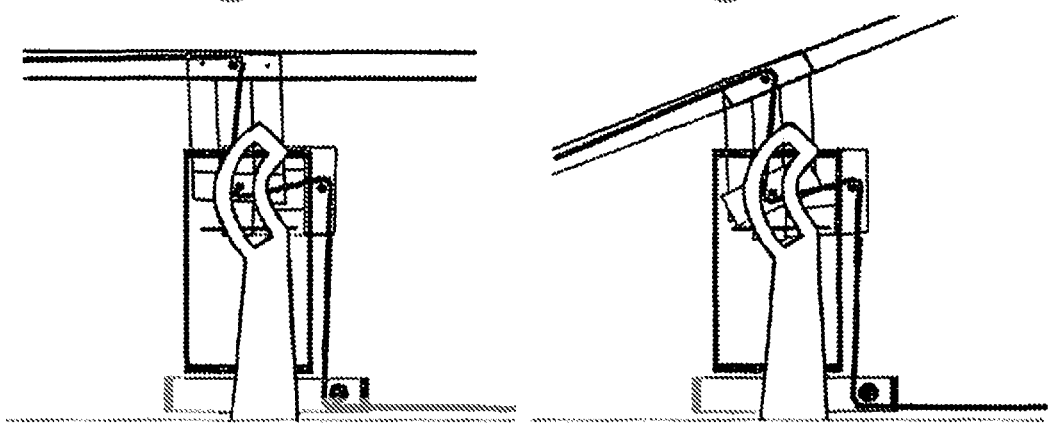
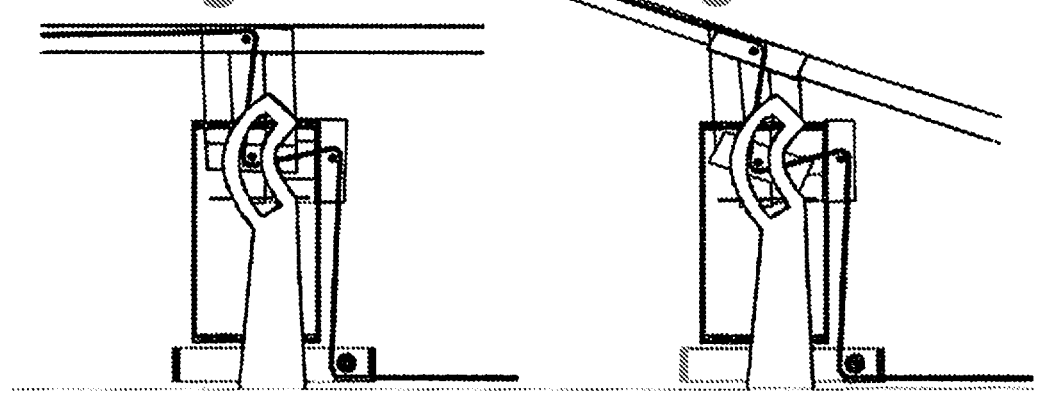
Fig. 24D

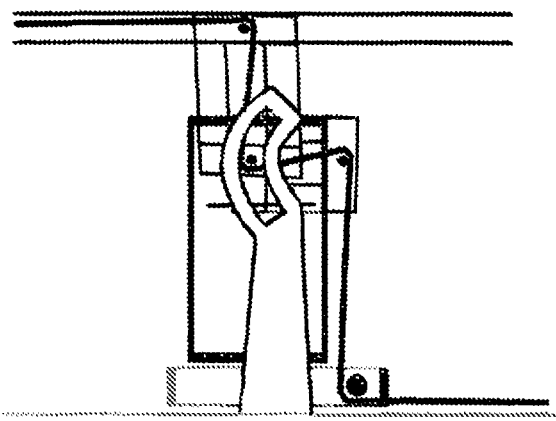
Fig. 24E1
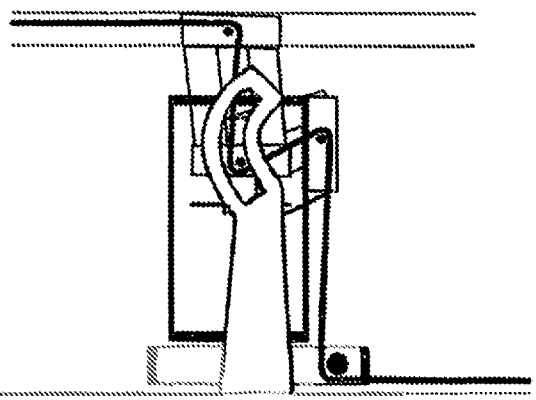
Fig. 24E2
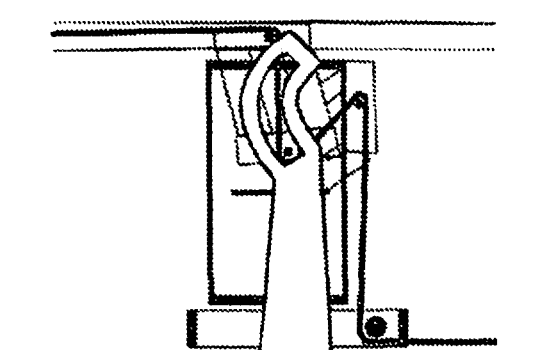
Fig. 24E3
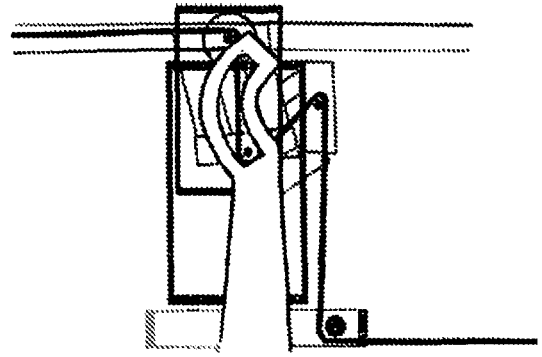
Fig. 24E4
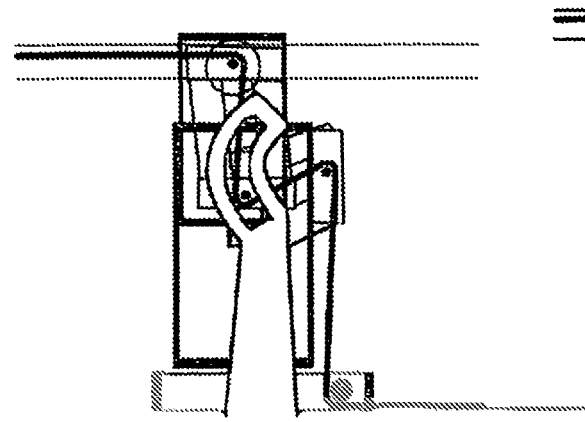
Fig. 24E5
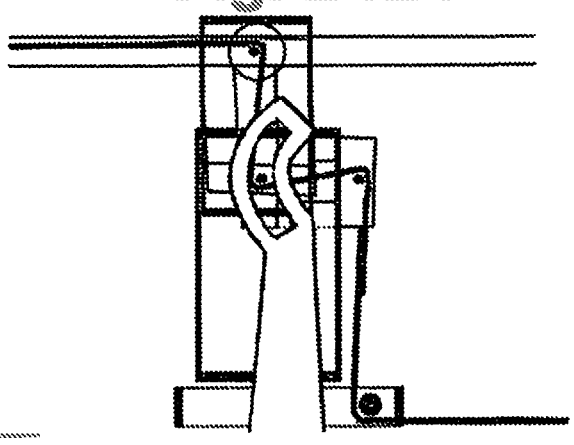
Fig. 24E6
Fig. 24E

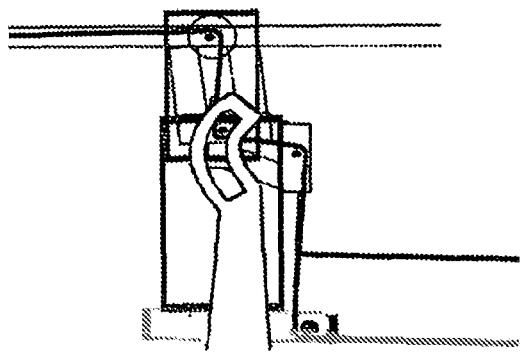
Fig. 24F1
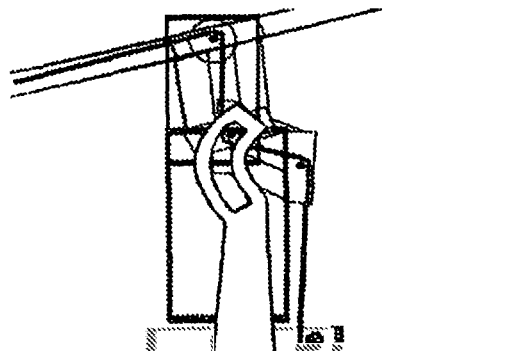
Fig. 24F2
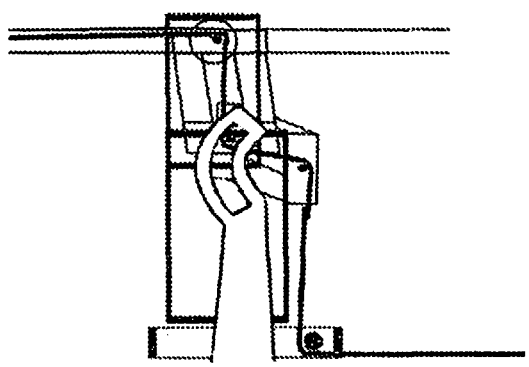
Fig. 24F3
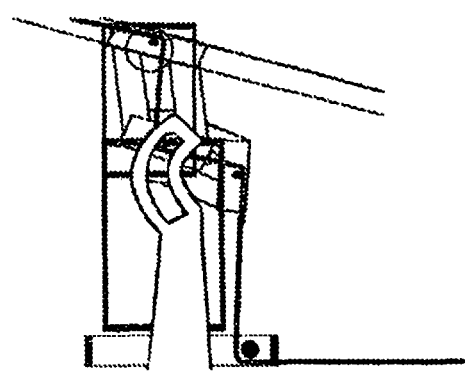
Fig. 24F4
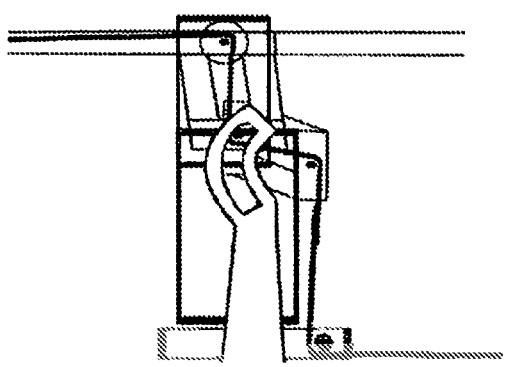
Fig. 24F5
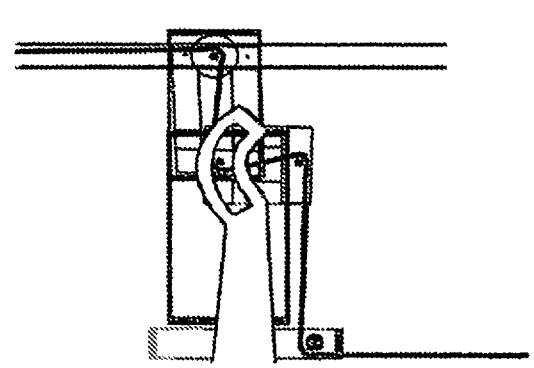
Fig. 24F6
Fig. 24F

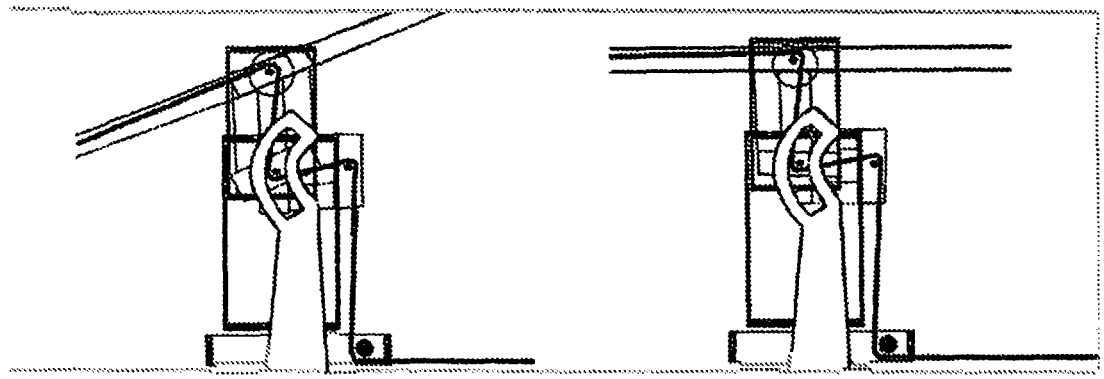
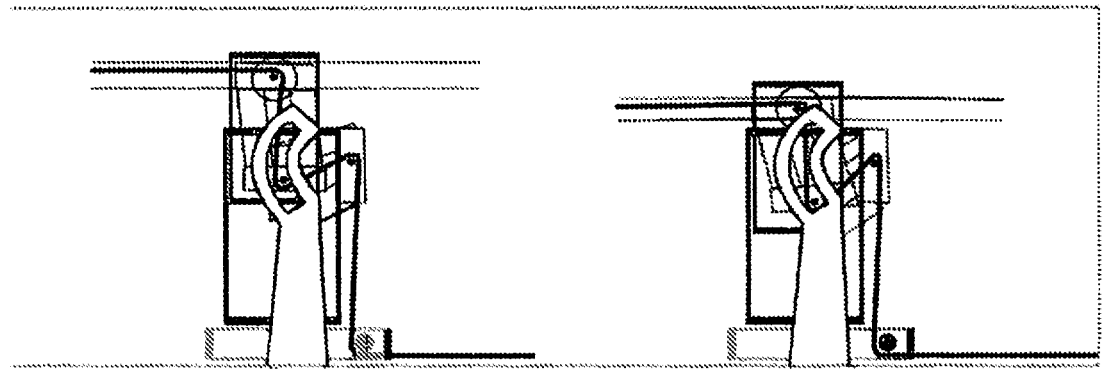
Fig. 24G

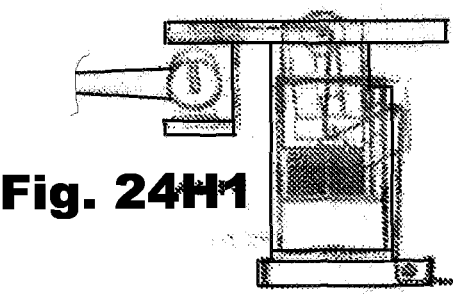
Fig. 24H1
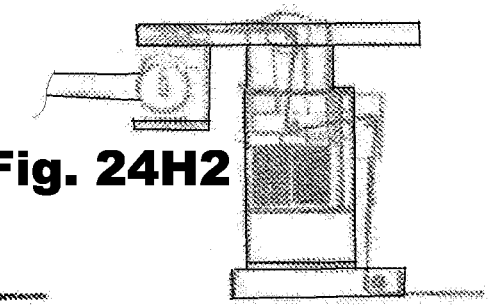
Fig. 24H2
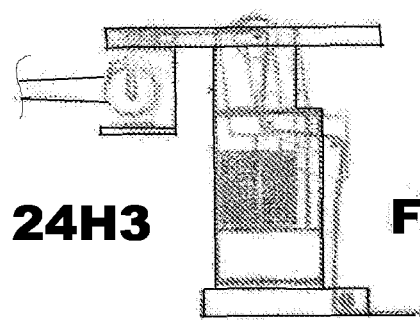
Fig. 24H3
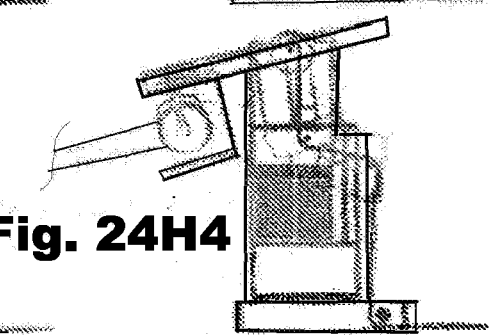
Fig. 24H4
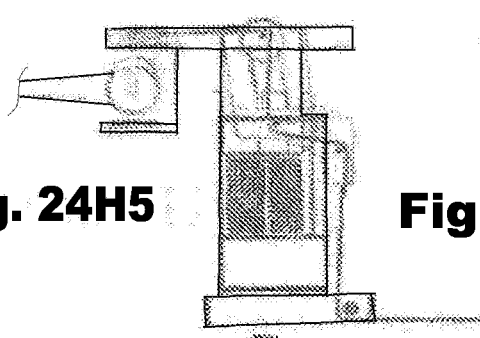
Fig. 24H5
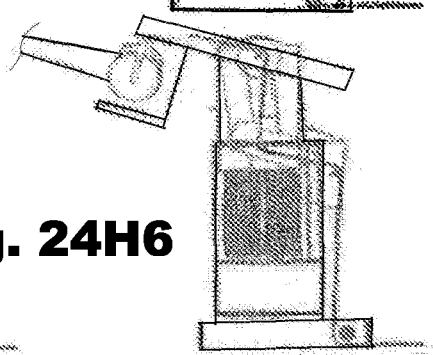
Fig. 24H6
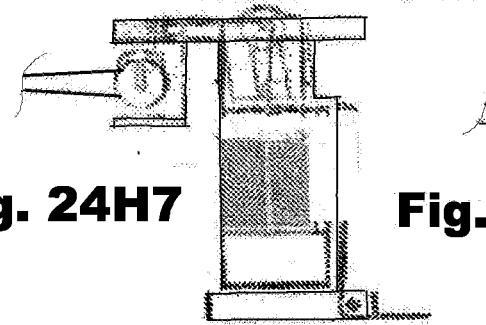
Fig. 24H7
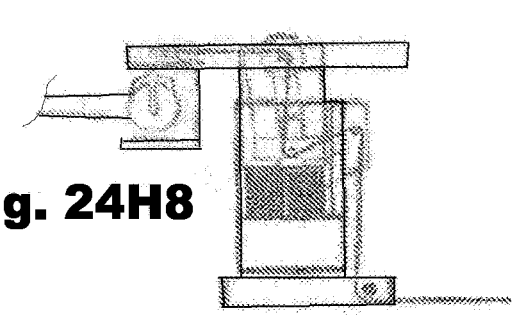
Fig. 24H8

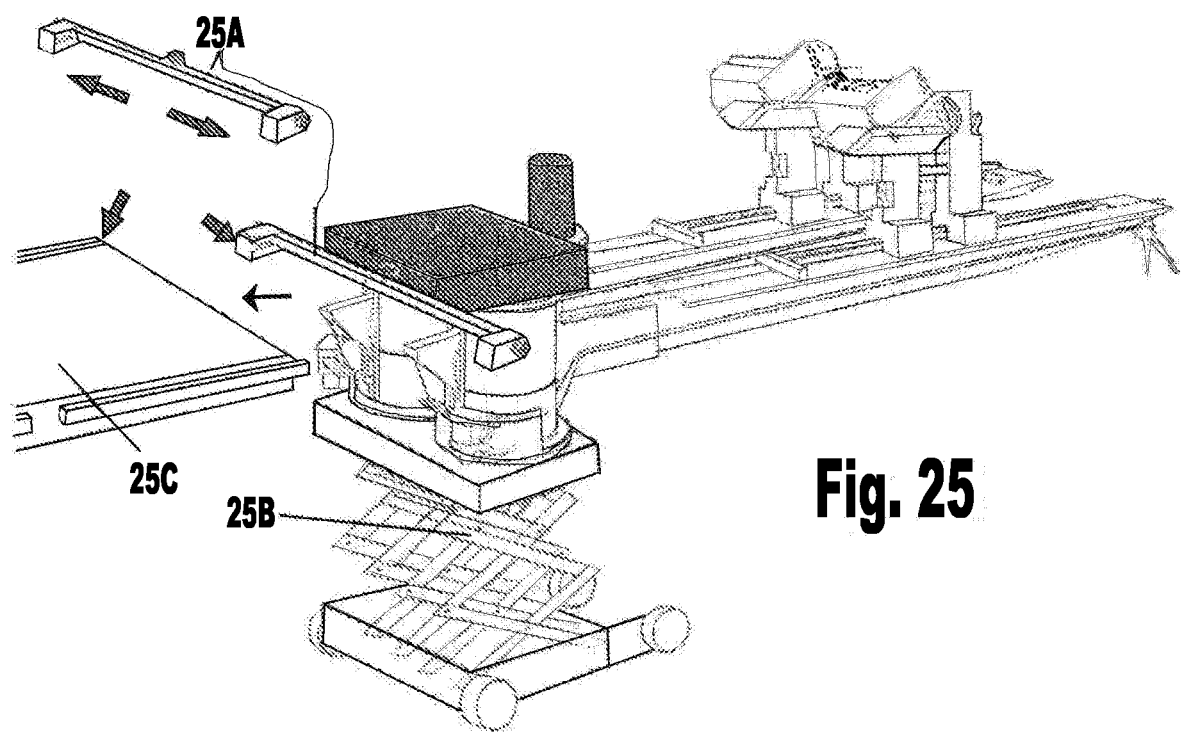

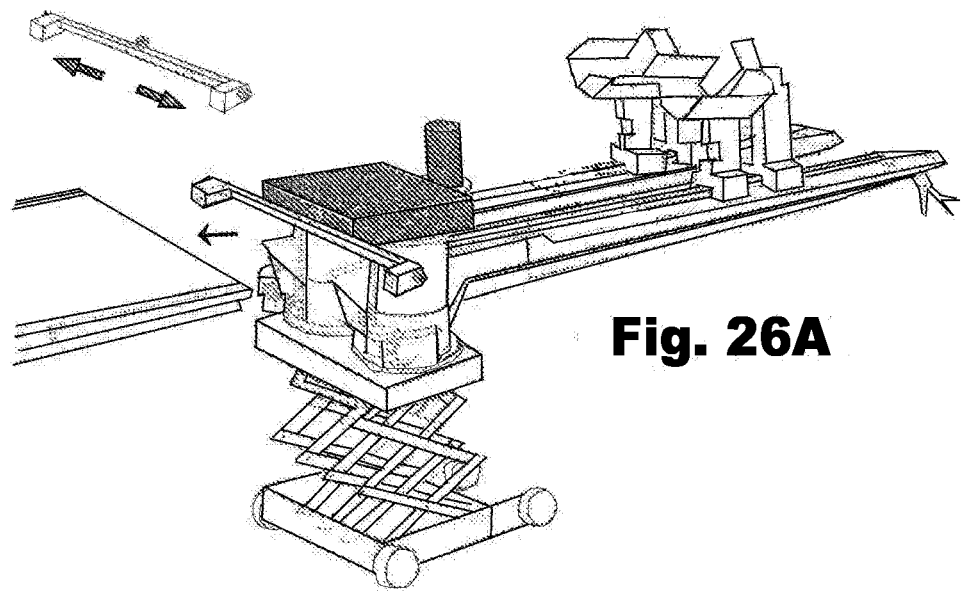
Fig. 26A
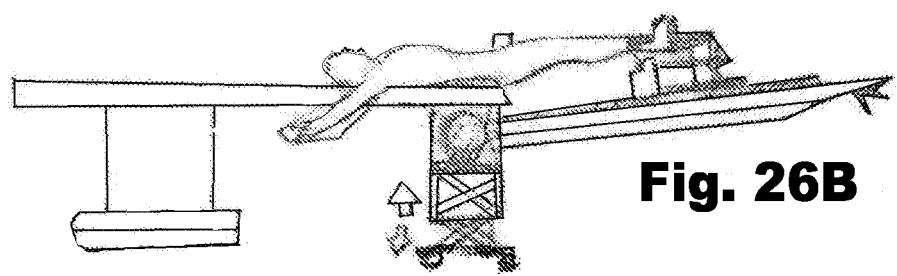
Fig. 26B
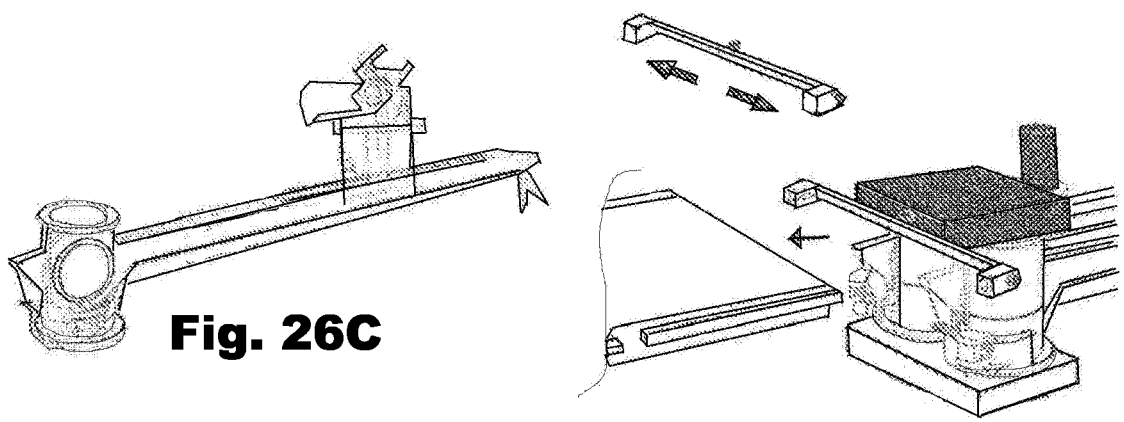
Fig. 26C
Fig. 26D

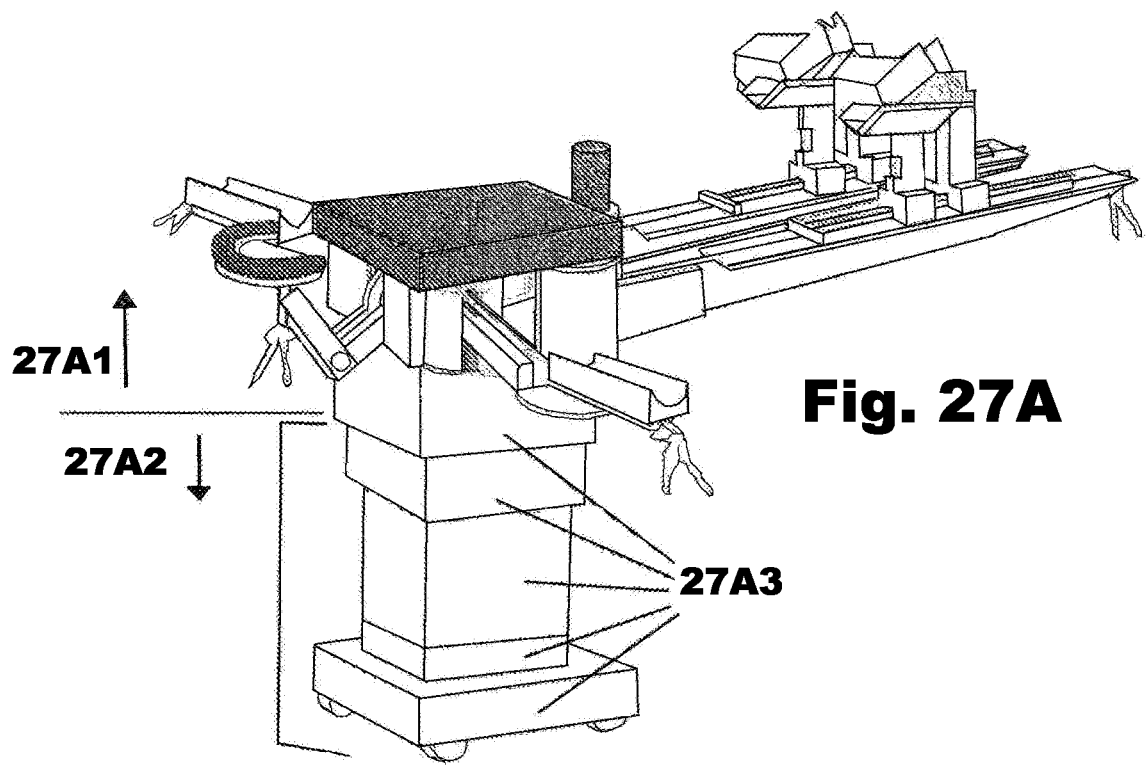

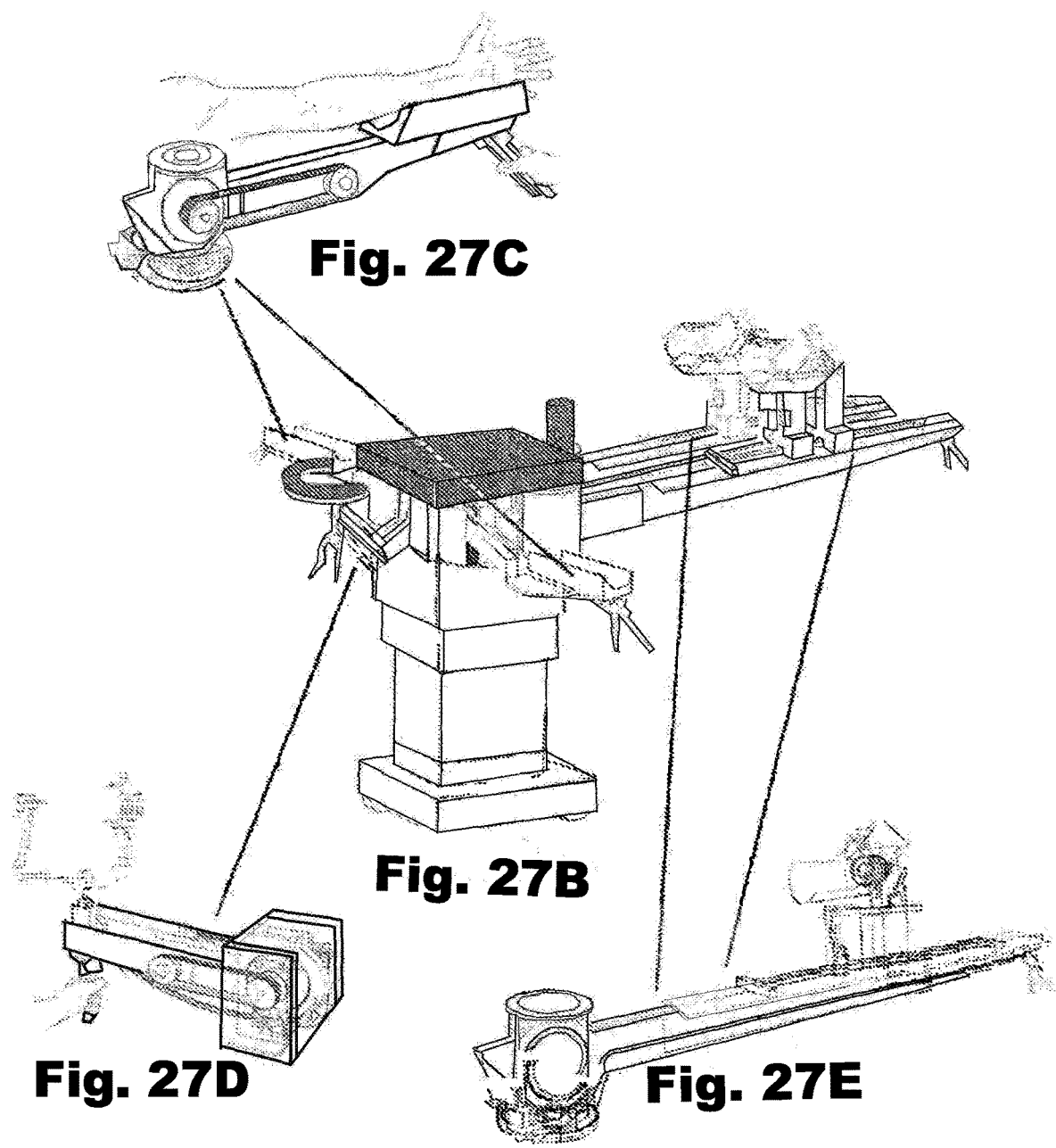

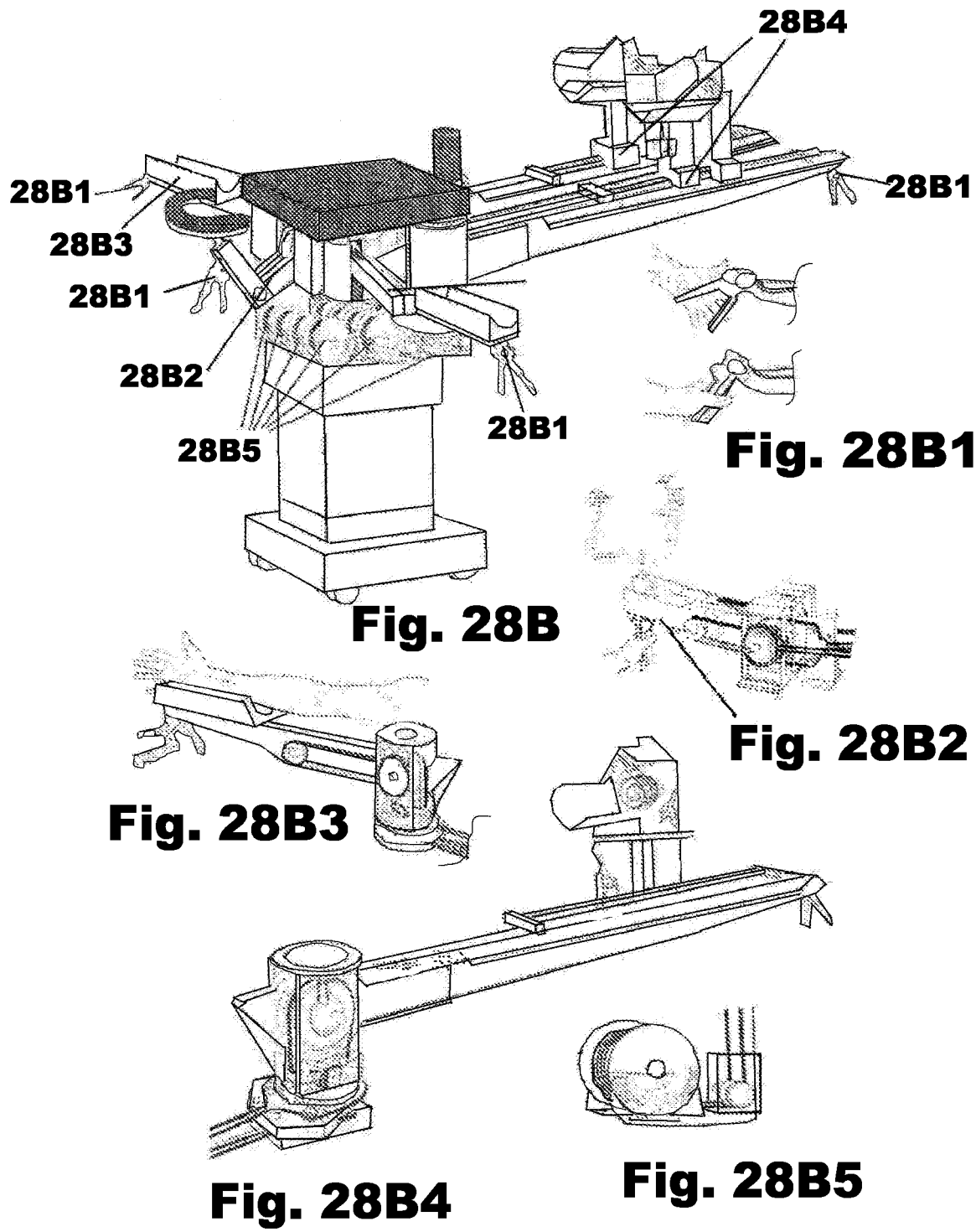

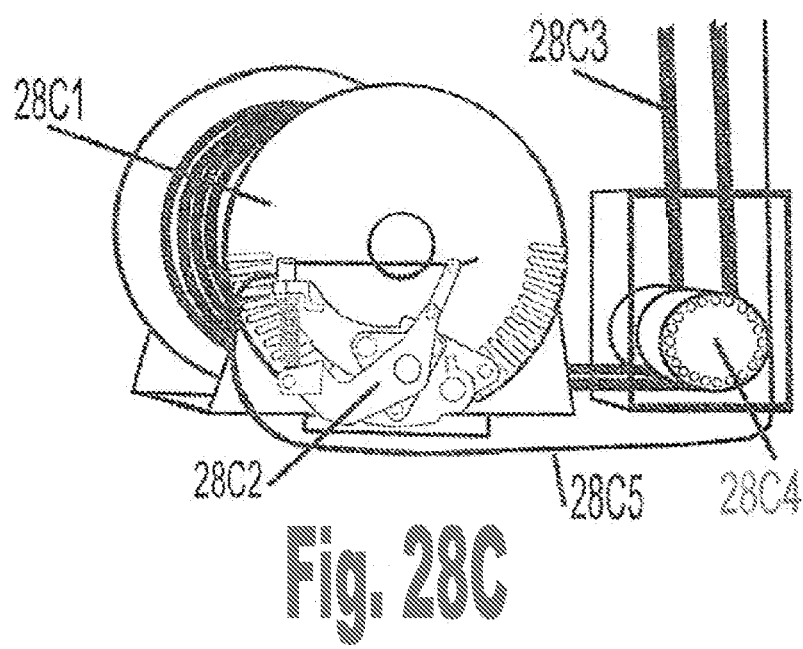

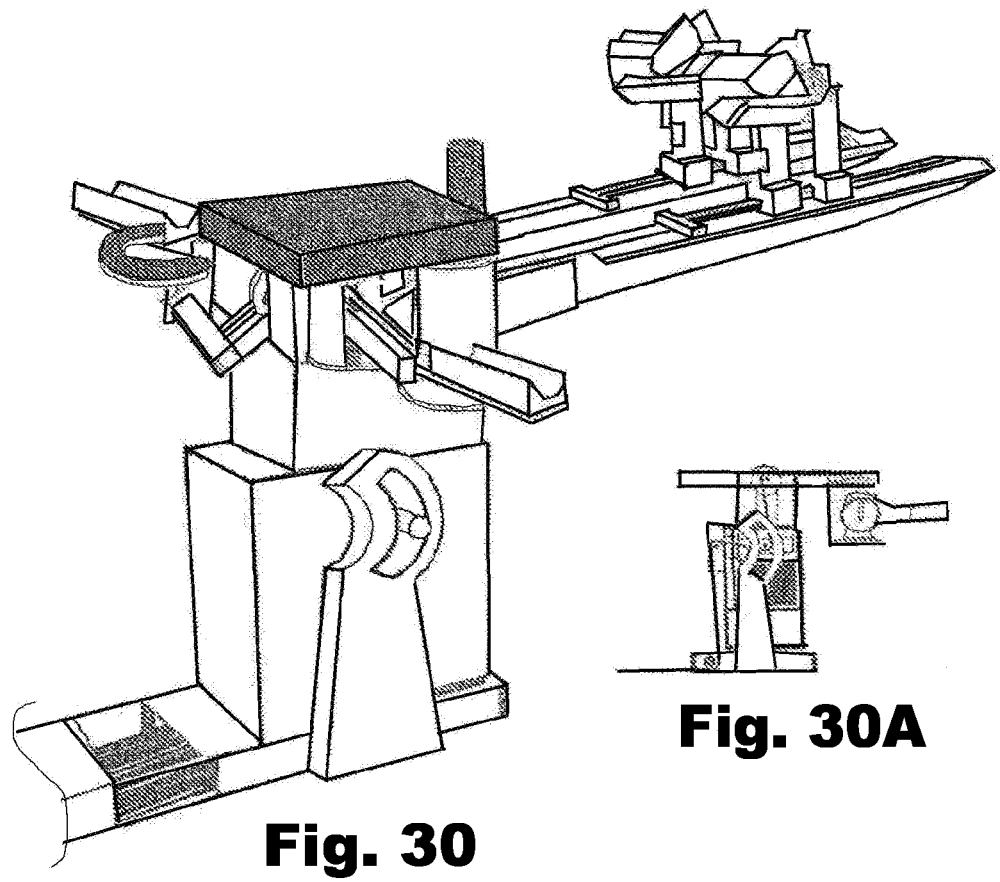
Fig. 30A
Fig. 30
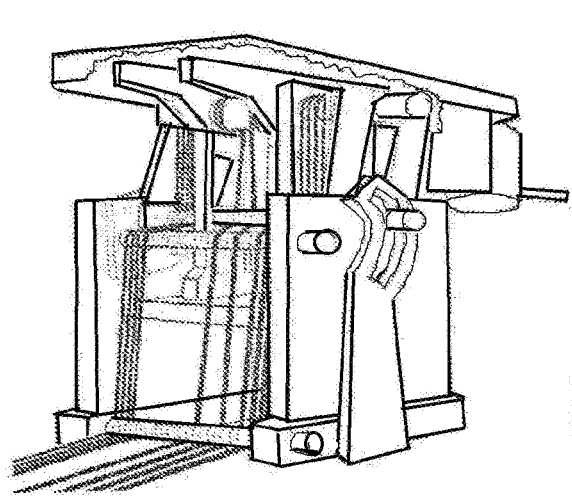
Fig. 30B
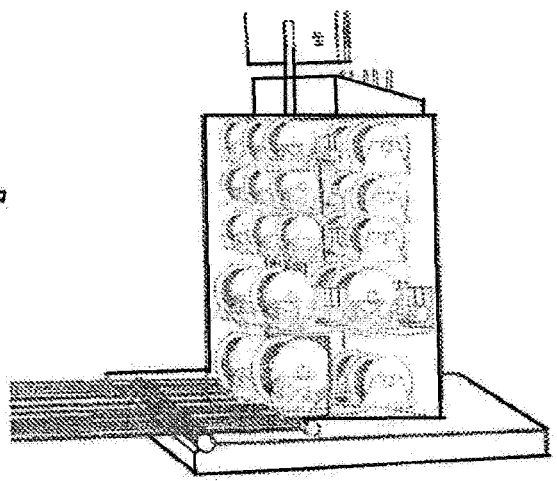
Fig. 30C

ARTICULATING PATIENT POSITIONING APPARATUS

CROSS-REFERENCE TO RELATED APPLICATIONS

The present patent application is a continuation patent application that claims priority to U.S. patent application Ser. No. 13/902,939, titled "An Articulating Patient Positioning Apparatus", filed on May 27, 2013, that claims priority to the continuation-in-part patent application of the U.S. patent application Ser. No. 13/251,985 entitled "Method and Apparatus for Radiolucent Anatomic Positioning", filed on 3 Oct. 2011 under 35 USC 111(a), which in turn claims priority benefit of the U.S. provisional application for patent Ser. No. 61/389,271 filed on 3 Oct. 2010 under 35 U.S.C. 120 and entitled "Method and Apparatus for Achieving Variable Radiolucent Anatomic Positioning Via the Usage of Non Metallic, Articulating, Variably Positioning, an Lockable Interconnecting Radiolucent Joints", under 35 U.S.C. 119(e); all of which are hereby incorporated by reference herein. The present continuation-in-part patent application also claims priority benefit of the U.S. provisional application for patent Ser. No. 61/682,279 filed on 12 Aug. 2012 under 35 U.S.C. 120 and entitled "Method and Apparatus for Radiolucent, Non Metallic, Articulating ANATOMIC Limb Positioning in the XYZ coordinates, powered and non powered", under 35 U.S.C. 119(e); the contents of which are also incorporated herein by reference for all purposes to the extent that such subject matter is not inconsistent herewith or limiting hereof.

RELATED CO-PENDING U.S. PATENT APPLICATIONS

The following related U.S. patent application(s), submitted by at least one of the present Applicant(s)/Inventor(s) is/(are) recently co-pending: U.S. utility patent application Ser. No. 13/251,985 filed, entitled" Method and Apparatus for Radiolucent Anatomic Positioning", submitted to the United States Patent and Trademark Office (USPTO) on 3 Oct. 2011.

U.S. utility patent application Ser. No. 13/902,932 filed, entitled" A System, Apparatus and Method for Shoulder Migration", submitted to the United States Patent and Trademark Office on 27 May 2013.

FEDERALLY SPONSORED RESEARCH OR DEVELOPMENT

Not applicable.

REFERENCE TO SEQUENCE LISTING, A TABLE, OR A COMPUTER LISTING APPENDIX

Not applicable.

COPYRIGHT NOTICE

A portion of the disclosure of this patent document contains material that is subject to copyright protection. The copyright owner has no objection to the facsimile reproduction by anyone of the patent document or patent disclosure as it appears in the Patent and Trademark Office, patent file or records, but otherwise reserves all copyright rights whatsoever.

FIELD OF THE INVENTION

One or more embodiments of the invention generally relate to medical and surgical patient positioning. More particularly, the invention relates to a primarily non-metallic, articulating patient positioning system.

BACKGROUND OF THE INVENTION

The following background information may present examples of specific aspects of the prior art (e.g., without limitation, approaches, facts, or common wisdom) that, while expected to be helpful to further educate the reader as to additional aspects of the prior art, is not to be construed as limiting the present invention, or any embodiments thereof, to anything stated or implied therein or inferred thereupon. In the field of Orthopedic Surgery, one may expect that many procedures performed are related to the lower extremities and may require the sustained anatomic positioning of the weight of the lower extremities variably throughout the x, y, and z coordinates. Present systems for providing said positioning and traction of the lower extremities often involve the usage of an entire surgical table to accomplish this task, motorized controls as well as a substantial usage of metallic components, which can be a significant source of imaging artifact that may be detrimental to optimum imaging in the newly evolving imaging environment as characterized by technologies such as, but not limited to, MRI, Computer assisted CT, and Cone Beam. It is believed that the next generation of surgery will likely involve the evolution of surgical robotics, surgical imaging and patient positioning all intersecting within an imaging zone of a hybrid operating room. Furthermore, one may expect that other portable means of combining these arts into one discipline may be useful in this evolution. Presently, the size of the imaging bores of imaging technology and imaging zones within hybrid operating rooms seems to be increasing. This increase in bore size may result in situations in which the usage of even non ferro-magnetic metals in minute amounts, for example, without limitation, one small screw, can affect the sensitive image gathering of these tools, which may, in some cases negate the clinical efficacy of such tools.

The following is an example of a specific aspect in the prior art that, while expected to be helpful to further educate the reader as to additional aspects of the prior art, is not to be construed as limiting the present invention, or any embodiments thereof, to anything stated or implied therein or inferred thereupon. By way of educational background, another aspect of the prior art generally useful to be aware of is that there are currently many types of metallic means and partially metallic means of providing anatomical support in the field of surgical patient positioning. Some of these means may provide positioning and articulation of the upper and lower extremities, the head and neck, leg traction, hip positioning, etc. Said means often utilize non ferro-magnetic metals, for example, without limitation, stainless steel and aluminum, in order to interface with current imaging array technologies. Yet, these means may contribute to imaging artifact due to incidents such as, but not limited to metallic streak formation, high attenuation distortion, and density artifacts as well as "Black Hole" artifacts that may occur in MRI even when the usage of metallic components is generally confined to such areas as the providers of these positioning devices deem are outside of the imaging field. This may, at least in part, be due to the emergence of larger imaging bores. Some currently available anatomic positioners may be fashioned from nonmetallic materials. Many of these positioners use the same designs as their metallic counterparts, such that the weakness of these materials in comparison to metal may cause structural failure over time. In addition, it is believed that such positioners may be unequal to metallic means in the task of load bearing or, if designed for load bearing, feature only limited ability to dynamically position the extremities, head and neck. Non-limiting examples of such nonmetallic positioners may include leg or arm positioners with a portion of the positioner fashioned from radiolucent materials, but with all joints and load bearing components fashioned from metallic materials, positioners which are entirely nonmetallic yet only feature rudimentary positioning along one coordinate and may be fragile, head positioners which can be readily positioned yet cannot be placed inside of an imaging bore, or head positioners which are entirely nonmetallic yet are fragile and may require the tightening and untightening of screw fasteners by one person while another person supports the head and neck of an anesthetized patient in order to effect positioning and usage of this positioning aid.

The following is an example of a specific aspect in the prior art that, while expected to be helpful to further educate the reader as to additional aspects of the prior art, is not to be construed as limiting the present invention, or any embodiments thereof, to anything stated or implied therein or inferred thereupon. By way of educational background, another aspect of the prior art generally useful to be aware of is that there is know to be a crowded field of conventional solutions which are known to not be keeping pace with the quantum performance leaps of ever improving modem imaging technology, and which often impede accurate and efficient anatomical positioning, often, due to the introduction of errors such as imaging artifact, poor positioning efficacy, limited load support, etc. Additionally, there are few, if any, attempts to address the much higher imaging accuracy needs of next generation surgery technologies, such as, without limitation, the evolution of surgical robotics, surgical imaging and patient positioning all intersecting within the imaging bore of the hybrid operating room.

In view of the foregoing, it is clear that these traditional techniques are not perfect and leave room for more optimal approaches.

BRIEF DESCRIPTION OF THE DRAWINGS

The present invention is illustrated by way of example, and not by way of limitation, in the Figs. of the accompanying drawings and in which like reference numerals refer to similar elements and in which:

Figs. IA, IB and IC illustrate an exemplary radiolucent anatomical positioner with articulating joints, in accordance with an embodiment of the present invention. Fig. IA is a diagrammatic side view of the positioner attached to a patient platform. Fig. IB is a diagrammatic front view, and Fig. IC is an exploded view;

FIGS. 2A and 2B illustrate an exemplary articulating vertical base joint and an exemplary articulating horizontal joint, in accordance with an embodiment of the present invention. FIG. 2A is a diagrammatic side view, and FIG. 2B is a diagrammatic top view;

FIG. 3 is a diagrammatic side view of an exemplary articulating vertical joint, in accordance with an embodiment of the present invention;

FIGS. 5A and 5B illustrate an exemplary radiolucent and lockable lower extremity anatomical positioner with articulating joints that may be positioned virtually anywhere within the x, y, and z coordinates, in accordance with an embodiment of the present invention. FIG. 5A is a side perspective view, and FIG. 5B is a transparent side perspective view;

FIG. 6 is a transparent side perspective view of an exemplary nonmetallic, radiolucent, articulating and lockable lower extremity anatomical positioner with articulating joints, in accordance with an embodiment of the present invention;

FIG. 9A is a side perspective view. FIG. 9B is a transparent side perspective view, and FIG. 9C is an exploded view;

FIGS. 12A through 12C illustrate an exemplary anatomical positioner that may be actuated by a caliper and rotor system, in accordance with an embodiment of the present invention. FIG. 12A is a side perspective view. FIG. 12B is an exploded side perspective view, and FIG. 12C is an exploded view of a turntable hub portion of the positioner;

FIG. 14A shows a closed caliper with the hand control released, and FIG. 14B displays an open caliper with the hand control engaged allowing full position-ability;

FIG. 17 illustrates exemplary rotor caliper equipped free spinning winches located within the hub of an operating room table, in accordance with an embodiment of the present invention;

FIG. 18 illustrates an exemplary caliper cable rotor hybrid system in use positioning in a Trendelennberg and a reverse Trendelenberg modality, in accordance with an embodiment of the present invention;

FIGS. 19A through 19C illustrate an exemplary hand operated radiolucent and primarily nonmetallic head positioner, accordance with an embodiment of the present invention. FIG. 19A is a side perspective view. FIG. 19B is an exploded view, and FIG. 19C illustrates the range of motion of the head positioner;

FIGS. 21A1-21A12, FIGS. 21A, 21AA and 21BB illustrate an exemplary upper extremity positioner 13A actuated by a caliper rotor with a 90 degree elbow bend, in accordance with an embodiment of the present invention;

FIG. 25 illustrates an exemplary remotely operated, non-metallic, height adjustable Trendelenberg and reverse Trendelenberg imaging compatible operating table, in accordance with an embodiment of the present invention;

FIGS. 26a and 26b illustrates an exemplary embodiment of the lower extremity positioning module, in accordance with an embodiment of the present invention. FIG. 26C illustrates an exemplary hand actuated caliper brake lower extremity positioner; FIG. 26D illustrates a detailed view of the means of mounting the lower extremity positioning module to a standard operating room table;

FIG. 27A illustrates an exemplary embodiment of a hand actuated cable rotor operating table, utilizing the present invention in concert with a conventional height adjustable table in accordance with an embodiment of the present invention; 27A1 is the non-metallic portions of the operating table; 27A2 is the metallic conventional height adjustable table portion; 27A3 is the Height Adjustable and Trendelenberg Tilt components of the conventional metallic operating table;

FIG. 27b illustrates an exemplary embodiment of a hand actuated caliper rotor operating table, in accordance with an embodiment of the present invention; FIG. 27C illustrates a set of hand actuated caliper rotor upper extremity positioners in accordance with an embodiment of the present invention; FIG. 27D illustrates a hand actuated caliper rotor head and neck positioner in accordance with an embodiment of the present invention; FIG. 27E illustrates a set of hand actuated caliper rotor lower extremity positioners in accordance with an embodiment of the present invention;

FIGS. 28B, and 28B1-28B5 illustrates the constituent components of 28A;

FIG. 30 illustrate exemplary transparent views of a remotely operated non metallic height adjustable, trendelenberg tilt, flexion extension operating room table, in accordance with an embodiment of the present invention; 30A illustrating a transparent side view, 30B illustrating a view of the control and counterbalance cables and control cable mechanisms, and 30C illustrating a transparent view of the remote cable windlass and counterbalance cable assembly with control system, in accordance with an embodiment of the present invention;

Figure 4A:
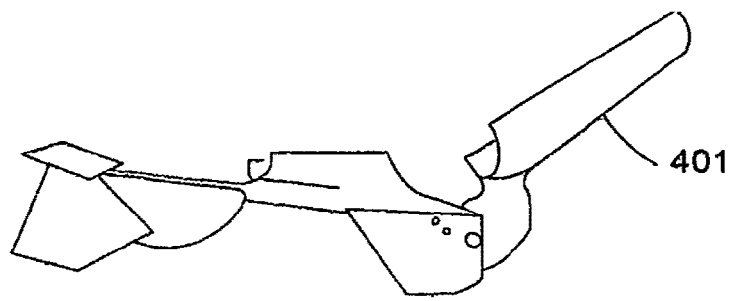
FIGS. 4A through 4G illustrate an exemplary radiolucent anatomical positioner in a variety of positions, in accordance with an embodiment of the present invention.

Unless otherwise indicated illustrations in the Figs. are not necessarily drawn to scale.

DETAILED DESCRIPTION OF SOME EMBODIMENTS

The present invention is best understood by reference to the detailed Figs. and description set forth herein.

Embodiments of the invention are discussed below with reference to the Figs. However, those skilled in the art will readily appreciate that the detailed description given herein with respect to these Figs. is for explanatory purposes as the invention extends beyond these limited embodiments. For example, it should be appreciated that those skilled in the art will, in light of the teachings of the present invention, recognize a multiplicity of alternate and suitable approaches, depending upon the needs of the particular application, to implement the functionality of any given detail described herein, beyond the particular implementation choices in the following embodiments described and shown. That is, there are numerous modifications and variations of the invention that are too numerous to be listed but that all fit within the scope of the invention. Also, singular words should be read as plural and vice versa and masculine as feminine and vice versa, where appropriate, and alternative embodiments do not necessarily imply that the two are mutually exclusive.

It is to be further understood that the present invention is not limited to the particular methodology, compounds, materials, manufacturing techniques, uses, and applications, described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to "an element" is a reference to one or more elements and includes equivalents thereof known to those skilled in the art. Similarly, for another example, a reference to "a step" or "a means" is a reference to one or more steps or means and may include sub-steps and subservient means. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures. Language that may be construed to express approximation should be so understood unless the context clearly dictates otherwise.

Unless defined otherwise, all technical and scientific terms used herein have the same meanings as commonly understood by one of ordinary skill in the art to which this invention belongs. Preferred methods, techniques, devices, and materials are described, although any methods, techniques, devices, or materials similar or equivalent to those described herein may be used in the practice or testing of the present invention. Structures described herein are to be understood also to refer to functional equivalents of such structures. The present invention will now be described in detail with reference to embodiments thereof as illustrated in the accompanying drawings.

From reading the present disclosure, other variations and modifications will be apparent to persons skilled in the art. Such variations and modifications may involve equivalent and other features which are already known in the art, and which may be used instead of or in addition to features already described herein.

Although Claims have been formulated in this Application to particular combinations of features, it should be understood that the scope of the disclosure of the present invention also includes any novel feature or any novel combination of features disclosed herein either explicitly or implicitly or any generalization thereof, whether or not it relates to the same invention as presently claimed in any Claim and whether or not it mitigates any or all of the same technical problems as does the present invention.

Features which are described in the context of separate embodiments may also be provided in combination in a single embodiment. Conversely, various features which are, for brevity, described in the context of a single embodiment, may also be provided separately or in any suitable subcombination. The Applicants hereby give notice that new Claims may be formulated to such features and/or combinations of such features during the prosecution of the present Application or of any further Application derived therefrom.

References to "one embodiment," "an embodiment," "example embodiment," "various embodiments," etc., may indicate that the embodiment(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment, although they may.

Headings provided herein are for convenience and are not to be taken as limiting the disclosure in any way.

The enumerated listing of items does not imply that any or all of the items are mutually exclusive, unless expressly specified otherwise.

The terms "a", "an" and "the" mean "one or more", unless expressly specified otherwise. Devices or system modules that are in at least general communication with each other need not be in continuous communication with each other, unless expressly specified otherwise. In addition, devices or system modules that are in at least general communication with each other may communicate directly or indirectly through one or more intermediaries.

A description of an embodiment with several components in communication with each other does not imply that all such components are required. On the contrary a variety of optional components are described to illustrate the wide variety of possible embodiments of the present invention.

As is well known to those skilled in the art many careful considerations and compromises typically must be made when designing for the optimal manufacture of a commercial implementation any system, and in particular, the embodiments of the present invention. A commercial implementation in accordance with the spirit and teachings of the present invention may configured according to the needs of the particular application, whereby any aspect(s), feature(s), function(s), result(s), component(s), approach(es), or step(s) of the teachings related to any described embodiment of the present invention may be suitably omitted, included, adapted, mixed and matched, or improved and/or optimized by those skilled in the art, using their average skills and known techniques, to achieve the desired implementation that addresses the needs of the particular application.

It is to be understood that any exact measurements/dimensions or particular construction materials indicated herein are solely provided as examples of suitable configurations and are not intended to be limiting in any way. Depending on the needs of the particular application, those skilled in the art will readily recognize, in light of the following teachings, a multiplicity of suitable alternative implementation details.

A practical embodiment of the present invention pertains to a method of fashioning mechanisms and apparatuses for variable intra-operative and diagnostic radiolucent anatomic patient positioning utilizing articulating and lockable interconnecting joints. Many practical embodiments are implemented without the use of metallic components while providing sufficient strength to support a sustained load, the implementation of which may facilitate and make possible the art of articulated anatomic positioning within current and newly emerging imaging technologies such as the 0-Arm and seamless interface with the next generation of operating room based open MRI imaging surgical suites. Some practical embodiments teach the fashioning of joints which utilize a narrow, interlocking male/female channels constructed of high strength laminar sheeting to replace the need for metal in the construction of an articulated joint with means for variable articulation and locking of such joints. Furthermore, some practical embodiments enable the construction of non-metallic, radiolucent anatomic support apparatuses which exhibit the full range of variable positioning throughout the entire range of the three plane (i.e., x, y, z) axes while simultaneously supporting weight bearing loads equal to those addressed by anatomic support structures utilizing metallic components.

Various embodiments of the present invention, may provide, in various combinations as needed, the various arts of surgical imaging, image guidance and surgical robotics into one discipline, by introducing dynamic patient positioning and support which may interface seamlessly within this environment, be able to non metallically deliver and coordinate pinpoint movement in concert with surgical robotics within the live imaging bore without artifact, be able to deliver tables and modules which may provide such upper and lower extremity and head and neck support in either modules or in substantially non metallic tables which may allow insertion, and provide dynamic articulation and support of the entire extremity, or even the entire patient anatomy within the live imaging bore.

FIGS. 1A, 1B and 1C illustrate an exemplary radiolucent anatomical positioner 100 with articulating joints, in accordance with an embodiment of the present invention. FIG. 1A is a diagrammatic side view of positioner 100 attached to a patient platform 101. FIG. 1B is a diagrammatic front view, and FIG. 1C is an exploded view. In the present embodiment, the articulating joints comprise interconnecting channels and members fashioned from high strength, rigid laminar sheeting arranged into an interlocking male/female configuration, similar to a book (i.e., male member) sliding into a slipcase (i.e., female member) with non-metallic connectors at pivot points. Said channels are fashioned in such a way as to allow the male and female members to articulate similarly to a patient's anatomical joint and to provide variable positioning along all axes (i.e., x, y, and z) in whatever number and arrangement is most applicable to the anatomical positioning solution desired.

Referring to FIG. 1A in the present embodiment, anatomical positioner 100 comprises a series of three hinged articulation points, an articulating vertical base joint 103, a pivoting horizontal joint 105 and an articulating vertical end joint 107, with locking actuated via variable insertion of non-metallic positioning pins. It is contemplated that some alternate embodiments may be implemented with more or fewer articulating joints depending on factors such as, but not limited to, the portion of the anatomy being positioned, the type of positioning solution desired, the size of the patient, etc. In the present embodiment, anatomical positioner 100 is secured to patient platform 101 via a rail attachment 109, which is a lockable channel designed to grasp a standard sized radiolucent accessory side rail 110 typical on patient platforms within imaging environments. Rail attachment 109 may be latched and unlatched via a rail latch 111 that is held in a latched position by a radiolucent spring 113. A user may depress rail latch 111 to release rail attachment 109 from side rail 110. It is contemplated that in some alternate embodiments, positioners may be implemented with various alternative means of attachment such as, but not limited to, various clamps, slotted members, friction pads, vise-like arrangements, bolts, screws, etc.

Referring to FIG. 1C in the present embodiment, vertical base joint 103 comprises an interior load bearing vertical support member 115 and two right angled supports 117 and 119 connected by an interconnecting buttress member 121. Interconnecting buttress member 121 creates space between right angled supports 117 and 119 into which load bearing vertical support member 115 is inserted. Referring to FIG. 1A, right angled supports 117 and 119 are connected to load bearing vertical support member 115 by a fixed pivot connection point 123 and an adjustable connection point 125. Load bearing vertical support member 115 and right angled supports 117 and 119 comprise multiple holes 127 into which the connection means (e.g., pin, bolt, screw, etc.) of adjustable connection point 125 may be inserted. This enables right angled supports 117 and 119 to rotate between a horizontal position and a vertical position and to be locked in place at multiple points between these positions.

Referring to FIG. 1C, horizontal joint 105 comprises a fixed support member 129, which is attached to right angled supports 117 and 119, and a rotating support member 131, which is movably attached between fixed support member 129 and right angled supports 117 and 119 by a fixed pivot connection point 133. Rotating support member 131 rotates about pivot connection point 133 and may be locked in place by a locking member being inserted into an adjustment hole 135 on rotating support member 131 and one of a multiplicity of adjustment holes 137 on fixed support member 129. The end of rotating support member 131 opposite connection point 133 comprises a multiplicity of attachment holes 139 to which two right angled supports with interconnecting buttress members 141 and 143 may be attached. Two limb supports with interconnecting load bearing vertical support members 145 and 147 connect to right angled supports with interconnecting buttress members 141 and 143 at vertical end joint 107. Referring to FIGS. 1A and 1C, a fixed pivot connection point 149 holds these members together and enables limb supports with interconnecting load bearing buttresses 145 and 147 to rotate between a horizontal position and a vertical position. An adjustment hole 151 enables locking means to be inserted into right angled supports with interconnecting buttress members 141 and 143 and then into one of a multiplicity of adjustment holes 153 on limb supports with interconnecting load bearing buttresses 145 and 147 to hold these members at a chosen angle.

In the present embodiment, the various male and female interconnecting laminar members may be variably positioned and made to maintain said position via a means of temporary securement for purposes of variable positioning and adjustable fixation of anatomical positioner 100. To accomplish this, some of the members of positioner 100 comprise a series of small circular holes arranged within the male and female interconnecting laminar sheets with locking and unlocking effected by the insertion and removal of a non-metallic positioning pin through both the male and female members as a means to retard further motion. Those skilled in the art, in light of the teachings of the present invention, will readily recognize that a multiplicity of suitable means of locking and unlocking the joints may be used in some alternate embodiments including, but not limited to, friction, toothed gears, pneumatic means, other mechanical means, etc. In one alternative embodiment, the locking means may be effected via an internal system of pulleys constructed from radiolucent Kevlar (i.e., Mountaineering) rope and threaded both thru and around the rim of the vertical support member such that the flexor and tensor functions of the joint may be effected via the variable motion of the rope in the manner of an artificial muscle with means of securement of said lock provided by a windlass or spool in the manner of a lockable reel. In other alternative embodiments, the means of locking and securing the joint may be affected via the interposition of a PEEK spring actuator enclosed in a housing. Said housing equipped with an internal slotted mechanism interfacing with said Peek spring actuator so that the joint locks automatically when released after having been manipulated into optimum positioning.

In the present embodiment, anatomical positioner 100 is constructed of laminar sheets of radiolucent carbon fiber. In some alternate embodiments, the same method of construction may be applied to various different materials such as, but not limited to, Poly Ethyl Ethyl Ketone (PEEK), exotic materials as are presently available or as will present in future, etc. Furthermore, the present embodiment describes flat laminar sheeting connected to the articulating joints to provide support to various portions of a patient's anatomy such as, but not limited to, arms, legs and heads. It is contemplated that in some alternate embodiments, various different means of support may be provided, including, but not limited to, rods, sheets, cylinders, tubes, tube like sections, assemblies, arches, etc. In addition, in some alternate embodiments the support members may be adjustable in length and/or width.

Referring to FIGS. 1A and 1B, limb supports 145 and 147 comprise padding 155 and fixed support member 129 comprises padding 157. Padding 155 and 157 is made of radiolucent positioning foam shaped ergonomically to the anatomic feature to be positioned. Padding 155 and 157 is also contained within a hypo-allergenic sheeting material. Those skilled in the art, in light of the teachings of the present invention, will readily recognize that a multiplicity of suitable means of padding may be used in some alternate embodiments such as, but not limited to, memory foam, gel pads, liquid filled bladders, disposable or non-disposable fabric, non-fabric sheathing, rubber sleeves, padded sleeves which slip over the entire apparatus and are fitted with straps to retain anatomic portions, hook and loop attached radiolucent foam forms fitted with straps to retain anatomic portions, padded straps which wrap circumferentially around the apparatus, etc. Other alternate embodiments may be implemented without padding. Some embodiments of the present invention also comprise means of securing the patient's anatomy to the positioner such as, but not limited to, straps comprising hook and loop material, elastic bands, foam clamshells, various different fabric closures, catchments, etc.

In typical use of the present embodiment, a user depresses rail latch 111 and attaches rail attachment 109 to accessory side rail 110 on patient platform 100. Articulating joints 103, 105 and 107 are then adjusted so that positioner 100 can hold the patient's anatomy in the desired position for example, without limitation, holding the arm out from the body with the elbow bent at a 90-degree angle or holding the leg with the hip and knee bent so that the knee is pointing upward. Locking means secure joints 103, 105 and 107 in the desired positions. The patient is then placed on patient platform 100 with the portion of the anatomy to be supported placed on positioner 100. Padding 155 and 157 provides comfort to the patient. If desired, securing means may be utilized to hold the patient's anatomy to positioner 100. Imaging of the patient may then be performed. Positioner 100 is designed to replicate the natural movement of the patient's anatomy in such a way as to facilitate placement and intra-operative anatomic positioning within the workable bore openings of state of the art 3D fluoroscopy and imaging technologies, including, but not limited to, MRis, C-Arms, the Medtronic 0-Arm, as well as emerging portable MRI devices, open MRI suites, and other technologies as yet to be introduced, as well as implementation as a either components within a patient care platform, such as, but not limited to, an operating or imaging room bed or chair, or as the main support components of an operating room bed or chair, such that the present invention acts in the manner of a variably positionable, radiolucent articulating suit of armor beneath a patient in the imaging setting, effectively replacing the need for preexisting means of patient platforms to include beds and chairs.

Positioner 100 is generally functional within the surgical and diagnostic environments and typically meets all load-bearing criteria with respect to anatomical positioning apparatuses. The present embodiment presents a means of using the combined strength of multiple articulating layers of laminar sheets of radiolucent material as a means of providing variable positioning, lockable, load bearing support and positioning of portions of the anatomy across the entire three dimensional xyz axes, as opposed to merely along the xy axes, while functioning within the magnetic and radiographic medical imaging environment. The spreading of the load bearing stress across the entire length and continuum of the laminar sheeting of the multiple components of the articulating joints has the effect of generally avoiding the susceptibility to stress fractures and load failure which the concentration of stress through the thickening of load bearing components in currently available non-metallic radiolucent anatomic positioners often leads to. Each component of the joint acts as a load bearing support upon which rests the portion of the anatomy. As such, lateral downward pressure/load bearing stress in the anatomic support plane translates into an increased compression force which presses together the segments of the joint which form the vertical support. Meanwhile, lateral stress in the vertical support translates into a firmer bond between the segments forming the vertical support and increased load bearing potential.

FIGS. 2A and 2B illustrate an exemplary articulating vertical base joint 201 and an exemplary articulating horizontal joint 203, in accordance with an embodiment of the present invention. FIG. 2A is a diagrammatic side view, and FIG. 2B is a diagrammatic top view. In the present embodiment, vertical joint 201 is able to articulate 90 degrees from a horizontal position to a vertical position, and horizontal joint 203 is able to rotate 180 degrees from parallel to the patient platform in a proximal direction to parallel to the patient platform in a distal direction. Articulating joints 201 and 203 comprise interconnecting channels and moving members fashioned from high strength, rigid laminar sheeting arranged into a male/female configurations with nonmetallic connectors at central pivot points. For example, without limitation, horizontal joint 203 comprises right angled members 205 and a fixed support member 207 that create a channel 209 into which a rotating support member 211 is inserted. These members are held together at a central pivot point by a non-metallic connector 213. Referring to FIG. 2B, locking means such as, but not limited to, a non-metallic pin, may be inserted into adjustment holes 215 on fixed support member 207 to hold rotating support member 211 at a desired position.

In the present embodiment, vertical base joint 201 is configured to bisect the length of the underside of the anatomic support structure. In some alternate embodiments, joint assemblies may be configured to be positioned laterally along the length of the side of the anatomic support structure, similar to the manner of positioning joints in a suit of armor, whereby the joint design is repositioned at the lateral aspect of the natural anatomic joint as opposed to directly beneath the natural anatomic joint. In other alternate embodiments, the joint may be placed in various different locations such as, but not limited to, offset from the center of the underside of the support structure, on top of the support structure, etc.

FIG. 3 is a diagrammatic side view of an exemplary articulating vertical joint 301, in accordance with an embodiment of the present invention. In the present embodiment, a right angled support with interconnecting buttress member 303 is attached to a limb support member 305 by a non-metallic pin inserted into a central pivot point 307. Locking means inserted into an adjustment point 309 on right angled support with interconnecting buttress member 303 corresponds to a multiplicity of adjustment holes (not shown) on limb support member 305 to lock limb support member 305 in one of a multiplicity of positions. Vertical joint 301 is able to articulate 90 degrees from a horizontal position to a vertical position and may be locked in various different positions between these positions.

Figure 4B:
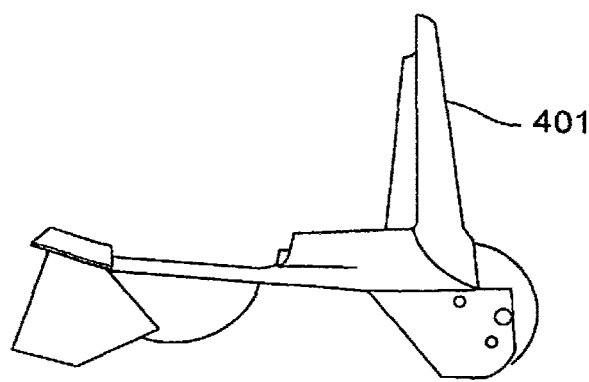
Figure 4D:
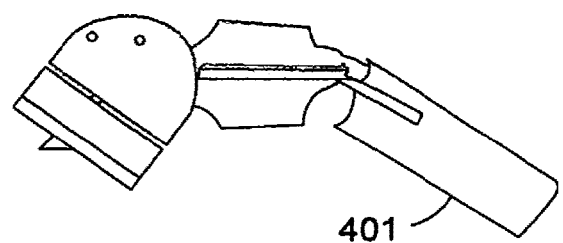
Figure 4C:
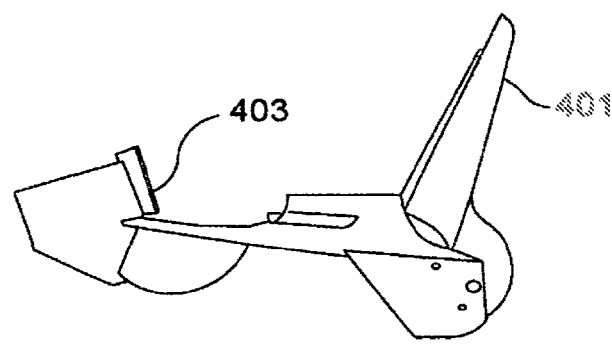
Figure 4E:
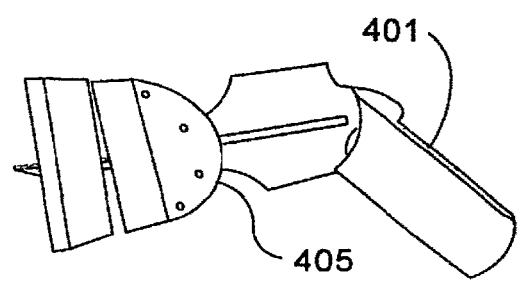
Figure 4G:
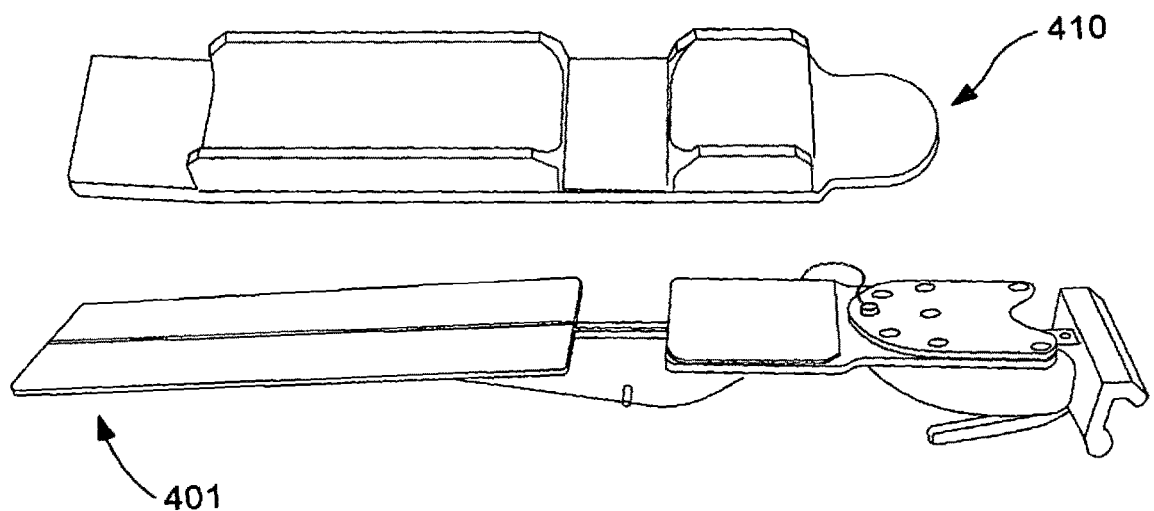
Figure 4F:
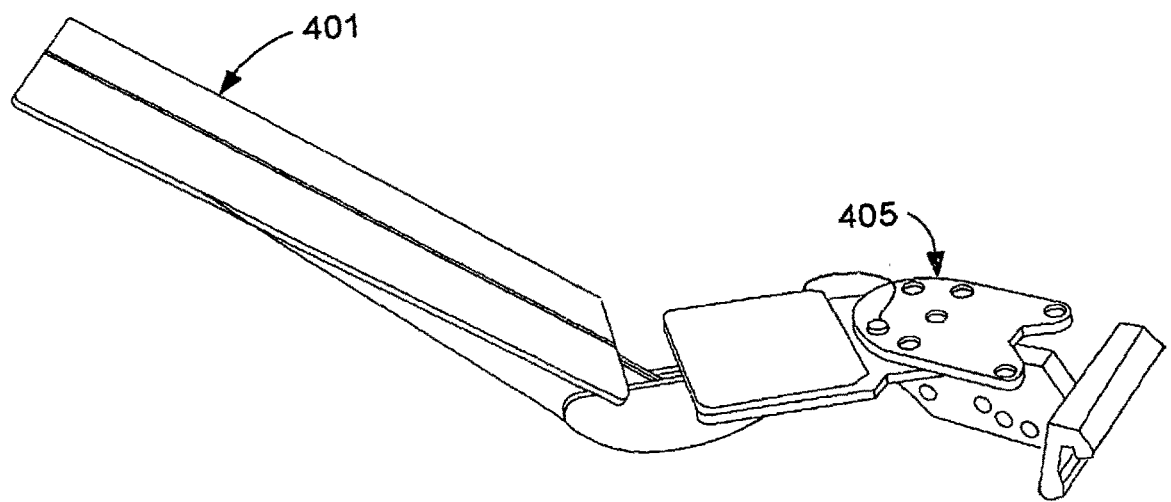

FIGS. 4A through 4G illustrate an exemplary radiolucent anatomical positioner in a variety of positions, in accordance with an embodiment of the present invention. FIG. 4A is a side view of the positioner with a limb support 401 in a partially raised position. FIG. 4B is a side view of the positioner with limb support 401 raised to a 90-degree angle. FIG. 4C is a side view of the positioner with limb support 401 in a raised position and a base joint 403 articulated to a near 90-degree angle. FIG. 4D is a top view of the positioner with limb support 401 in a raised position. FIG. 4E is a top view of the positioner with limb support 401 in a raised position and a horizontal joint 405 rotated to the right. FIG. 4F is a top view of the positioner with limb support 401 in a raised position and a horizontal joint 405 rotated to the left. FIG. 4G is a top view of the positioner with limb support 401 in a flat position and padding 410.

The exemplary anatomical positioners illustrated by way of example in the foregoing were related to upper extremity limb positioners. However, alternate embodiments of the present invention may be implemented as various different types of anatomical positioners and are not limited to the specific lengths, dimensions, number of joints, etc. illustrated by way of example in the foregoing embodiments. It is contemplated that those skilled in the art, in light of the teachings of the present invention, will readily recognize that the usage of high strength laminar sheeting in the construction of lockable radiolucent articulating joints may be implemented with regards to the construction of non-metallic, variably articulated and lockable radiolucent positioning aids in various different shapes and sizes and with various different numbers of joints for use with virtually any portion of the anatomy. For example, without limitation, some alternate embodiments may be implemented as an anatomic load bearing support for a lower extremity, as a neurosurgical head support, or as a hip positioner, all with full spectrum applicability to the entirety of magnetic and radiographic imaging environments. In some alternate embodiments, the radius of the vertical support members and buttresses may be increased to be configured for up to 360 degrees of rotation. As such, the articulating joint design may be combined into various different supports and positioners and may be placed laterally to the anatomical joint, as opposed to medially.

The embodiments described and illustrated by way of example in the forgoing comprise flat laminar sheets of radiolucent material configured as the means of anatomic support which may or may not be configured to accommodate various shaped, low-density (i.e., radiolucent) pads which have been curved or fashioned to mirror the parameters of specific anatomic shapes. In some alternate embodiments, the flat laminar sheets may be fashioned as simple planes, as truncated cylinders, as segments of parabola, or as various other more complex shapes and size as would be deemed applicable to one skilled in the art in light of the teachings of the present invention. Additionally, some alternative embodiments may include, without limitation, a series of open ended, flat concentric adjustable rings or ring segments configured to work in concert with various shaped low-density (i.e., radiolucent) pads which are curved or fashioned to mirror the parameters of specific anatomic shapes. Other alternate embodiments may comprise a multiplication of the method of interlocking male and female laminar sheets via an arrangement of any number of said articulating joints working in tandem and in varying sizes and arrangements, so that these interlocking joints might be arranged side by side in the manner of the blades of a threshing machine, or fashioned in such a manner as to scissor much like the blades of a hinged shrubbery trimmer. Other alternative embodiments may do away with the laminar sheets in favor of the usage of corrugated members as the solution to reduction of density artifact, or may alter the method of usage of flat laminar sheets via the introduction of eccentric curvature to these sheets in the manner of leafs or petals, thereby emulating nature, and yet essentially working within the method as herein introduced. In other alternative embodiments, fenestrations or openings may be introduced to either the laminar sheets utilized in the exemplary embodiment or to other members, which may replace the laminar sheets. In another embodiment of the present invention the laminar sheets are given support via movable structures placed beneath said articulating laminar sheets in the manner of shadow puppetry, wherein adjustable length tubes, rods or members provide the load bearing support, or via the usage of load bearing radiolucent cables, strings, slings or various other rigid or non-rigid assemblages suspended via an armature from above, in the manner of marionette puppetry; puppetry being an excellent description of said alternative embodiments, in that puppetry, like the present invention, deals with the support and positioning of articulated anatomic members. In other alternative embodiments of the present invention, a series of nested, overlapping cylindrical segments constructed so as to articulate in the manner of a centipede's exoskeleton utilizing an articulating joint beneath the anatomic joint or lateral to the anatomic joint. Yet other alternate embodiments may replace the articulating joint with a lockable spool/windlass utilizing the strength and radiolucent qualities of Kevlar mountaineering rope as both flexor and tensor threaded thru semi cylindrical articulating radiolucent exoskeleton segments. Still other alternative embodiments may replace the articulating joint with a piston or interconnecting assemblage of male female components arranged along the side of the natural anatomic joint, such that the variable elongation or shortening of the total length of the piston like male and female assembly would result in a replication of the flexor tensor operation of the anatomic joint, such a piston like arrangement may be actuated via an internal radiolucent pulley, such that operation of a spool/windlass would lengthen or shorten said piston. Other alternative embodiments may include various other methods of actuating the lengthening and shortening of said male female piston like assemblies, said piston relying upon it's own internal strength for load bearing, or utilizing methods of load bearing and positioning based upon the aforementioned marionette and or shadow puppetry based solutions. Other alternative methods utilize flat and or eccentrically shaped laminar sheets as the piston like mechanism, said lockable and interconnecting laminar sheets adjustable in length in the manner of a man's belt threading thru various forms of buckle, and connected to the anatomic supports via either a slotted channel or a flat spool revolving on a center point, thereby allowing replication of the articulated hinge function while still offering no density artifact. Still other alternative embodiments of the present invention replace the articulating hinge with an overlapping series of male female members in the manner of two hands spreading their fingers and interconnecting, thereby emulating the natural hinge mechanism of an anatomical joint. Said "holding hands" method of interconnecting finger like protrusions may be variably positioned and locked via the interaction of lateral thumb-like mechanisms. Said thumb like mechanisms may communicate in the manner of a piston, a slotted belt like assembly configured from laminar sheeting, or via interaction with a rotating flat spools situated at the lateral end of the assembly. Such an alternative embodiment of an articulating hinge would mirror the action of two hands locked in the prayer position, with scissoring thumb like structures interacting as an adjustable component, and would thereby replicate the 180 degree function of a natural anatomic joint while exhibiting much improved radiolucent properties and maybe constructed of laminar sheets of radiolucent material.

Furthermore, those skilled in the art, in light of the teachings of the present invention, will readily recognize that at least some the foregoing embodiments may be readily configured to generally support a multiplicity of body parts, including, but not limited to, a limb, a head, as a lateral support during hip revision arthroplasty, etc. Similarly, some embodiments may also be configured as a general object support, which may be useful when the object/equipment must be used with a body part being imaged during medical imaging whereby the radiolucent properties of the object/equipment support apparatus is important.

Furthermore, those skilled in the art, in light of the teachings of the present invention, will readily recognize that at least some of the foregoing embodiments may be readily (re)configured and properly combined to achieve a replacement for a conventional surgical bed or chair.

Another practical embodiment of the present invention pertains to a method and apparatus for providing a portable modular component which may enable a conventional patient platform to accommodate surgical procedures of the lower extremities, while generally preventing metallic components from interfering with imaging of the patient anatomy, particularly in the area from the hips thru the foot. Furthermore, some embodiments may accomplish this while also providing effortless counterbalancing of the weight of the lower extremity or extremities as well as extreme ease of use thru a simple one position actuator and an automatic hands free braking system for positioning of the lower extremities throughout the x, y, and z coordinates as necessary for surgical and imaging access. Building upon use of flat, laminar, radiolucent sheeting, which is typically strong, nonmetallic, and imaging compatible, one embodiment comprises a vertical flat laminar turntable joint atop a horizontal flat laminar turntable joint to provide a means of nonmetallic positioning in the x, y, and z coordinates in the form of a nonmetallic boom and rotating hub. Some embodiments may be able to replicate the dynamic anatomical movement of various different portions of the human body such as, but not limited to, upper and lower extremities, the head and neck, the bend of elbow and knee joints, etc.

FIGS. 5A and 5B illustrate an exemplary radiolucent and lockable lower extremity anatomical positioner with articulating joints that may be positioned virtually anywhere within the x, y, and z coordinates, in accordance with an embodiment of the present invention. FIG. 5A is a side perspective view, and FIG. 5B is a transparent side perspective view. In the present embodiment, the positioner may employ remotely operable, pinpoint manipulation for various purposes such as, but not limited to, controlled microsurgery either in concert or not in concert with surgical robotics and either within or without an imaging array. Referring to FIG. 5B, the movement of a boom 500 may be performed thru the action of simultaneously rotating cable windlasses 501 positioned within a turntable hub 505 constructed from hi-strength, nonmetallic, flat laminar sheets utilizing ceramic bearings within nonmetallic turntables 510 m order to enable motion. Boom 500 may be used in a multiplicity of suitable positions to hold lower extremities such as, but not limited to, thighs, lower legs, hips, etc. in various different postures. The lower extremity positioner may be operable via remotely positioned winches or table housed winches which communicate motion to turntables 510 via controlled reeling and unreeling of cables 515. It is contemplated that these winches may be controlled via various different means, such as, but not limited to, a toggle, a joystick, via a computer program working in concert with image guidance, dials, levers, etc. In the present embodiments the remote winches are free spinning, which, when attached to the system, may create a closed system such an operator may use the winches to rotate boom 501 thru the rotation of windlasses 501 located in hub 505 or may move boom 500 at the tip of boom 500 and thereby cause windlasses 501 to rotate and cables 515 to automatically spool within the self-reeling winch. Typically, the closed system generally ensures that an equal amount of cable 515 is spooled into the system as is spooled out of the system regardless of the direction in which boom 500 is moved. This usually causes turntables 510 to rotate and the winches to spool or unspool automatically. Some embodiments comprising this type of closed system may comprise a hand control on the end of the boom to activate and deactivate a lock on the free spinning winch.

In the present embodiment, the positioner is counterbalanced non-metallically and remotely via the action of a spring reel, which may or may not be adjustable for tension. The length of boom 500 acts as a lever with turntable hub 505 as the fulcrum, which may create stress upon the effort side of boom 500 and make boom 500 difficult to use as a leg positioner due to weight. Conventionally, this problem is generally solved with brute force with the use of a massive metallic universal joint. In the present embodiment, the counterbalance weight is added to the effort end of boom 500 to mitigate stress on hub 505 while delivering sufficient load support to the load end of boom 500. The counterbalance may be used to render the apparatus into a state of equilibrium, thereby offsetting the natural lever action of boom 500 upon cable windlass hub 505 and typically providing effortless positioning of the apparatus. In some practical embodiments, this spring reel may be positioned apart from the patient surface and away from any imaging arrays that may be in use. The equilibrium typically created by the counterbalance provided by the spring reels may aid in minimizing stress and wear on the nonmetallic components of hub 505, thereby generally eliminating the necessity of metal ball joints or other types of metal joints or supports, which are frequently used in the current state of the field of lower extremity positioning. One embodiment may provide a variable spring reel, operable by a lever such that an operator could vary the load of the counterweight based upon the weight of the patient via a simple actuator such as, but not limited to, a lever, knob, sliding mechanism, etc.

In the present embodiment, the positioner also comprises an entirely nonmetallic foot positioner 520 which may enable rotation and angulation of the foot for optimized patient positioning of the lower extremities for purposes of hip and knee arthroplasty as well as for other purposes such as, but not limited to, the treatment of trauma, foot surgery, imaging of the lower extremities, etc. Foot positioner 520 may be able to migrate the lower extremity of a patient caudally as well as distally due to the angulation option via one handed usage and may be locked automatically. Foot positioner 520 may also allow for a fully extended leg or for a variable bend to the knee. In some applications, foot positioner 520 may also provide traction to the lower extremity, again with one handed manipulation and automatic, hands free locking. Referring to FIG. 5B, foot positioner 520 comprises spring operated hand controls 525 which typically allow for this one handed rotation and angulation with automatic hands free braking of foot positioner 520 as well as one handed caudal and distal migration of the entire leg with one handed bi directional traction and release of the leg. Referring to FIG. 1A, the positioner is shown with coverings, which may help to prevent tissue contamination or interference with the operable components during clinical or surgical usage.

Referring to FIG. 5B, the dynamic principles at work within turntable hub 505, which typically controls the positioning of the lower extremity support boom 500 in the x, y, and z coordinates via rotation and interaction of the cable windlasses 501 with the remotely positioned powered winches via the reeling and unreeling of nonmetallic, high strength cable 515, in the present embodiment are shown. FIG. 5B also illustrates, by way of example, sealed pulley blocks 530, which may enable directional control of the vertical and horizontal turntables 510 via interaction of nonmetallic cable 515 thru a centrally positioned foramen-like opening 535 in the center of the horizontal turntable 510. Vertical portions of cables 515 are typically able to spool and twist thru opening 535, which may typically allow for complete function of the vertical positioning of boom 500, even if the horizontal turntable 535 is in the action of swiveling or has been positioned at either extreme of the range of horizontal motion of boom 500. The configuration of cables 515 thru opening 535 functions similarly to the foramen magnum at the base of the human skull, which enables rotational mobility of the neurovascular bundle. Pulley blocks 530 comprise ceramic bearings within a solid sealed block of synthetic material such as, but not limited to, urethane or Delrin®. Any synthetic or non synthetic material providing sufficient strength may be used in many practical embodiments. Carbon Fiber, Polyethylethylketones (PEEK), DELRIN acetal polymer, TORLON polyamide-imide, PES Carbon Composite, as well as a plethora of other high performance polymers such as, but not limited to, Polyphenylene Sulfides, Polyetherimides, and Polyaryletherketones, as well as an array of emerging carbon fiber reinforced thermoplastic and polymer composites. which may provide friction free or low friction communication within the exemplary embodiment. Pulley blocks 530 also comprise channels through which cables 515 may be guided. In the present embodiment, pulley blocks 530 are configured so as to be press fitted to a housing to generally eliminate any unwanted migration. In some embodiments the pulley blocks may be held in place using a multiplicity of suitable means such as, but not limited to, adhesives, clips, plastic bolts, etc. To reiterate, the entire assemblage of the movable joints of the positioner as pictured, by way of example, in the present embodiment is entirely nonmetallic.

FIG. 6 is a transparent side perspective view of an exemplary nonmetallic, radiolucent, articulating and lockable lower extremity anatomical positioner with articulating joints, in accordance with an embodiment of the present invention. This positioner functions similarly to the foregoing embodiment described, by way of example, in accordance with FIGS. 5A and 5B. In the present embodiment, the positioner may be positioned in a multiplicity of suitable locations within the x, y, and z coordinates with one hand via the action of simultaneously rotating winches, which are allowed to spin freely when the operator uses one hand control. Said free spinning winches are typically located within the center of an operating table or other suitable patient support so that the metal components of these winches and a spring reel counterbalance system are positioned away from the imaging bore or imaging array. One handed positioning of a nonmetallic boom 600 and a rotating cable windlass hub 601 is typically easy due to the equilibrium provided by the centrally situated spring reel counterbalance system and automatic hands free braking and locking provided by a hand control located at the end of boom 600. The hand control and automatic braking system may be effected via various different means such as, but not limited to, the action of a caliper and a rotor attached to the free spinning winch such that, when the operator lightly squeezes the hand control, all winches controlling both the vertical and horizontal rotation of the cable windlasses within hub 601 are allowed to spin freely to allow for typically easy positioning of the entirely nonmetallic boom and hub assembly. When the operator releases the hand control, the rotor and caliper attached to the remote winch is automatically locked, thereby typically halting rotation of the horizontal and vertical cable windlasses within hub 601 and lower extremity boom 600. This braking system is more fully disclosed an illustrated, by way of example Figure. In the present embodiment, a foot positioner 620 may be used as a traction control apparatus similarly to foot positioner 525 illustrated by way of example in FIGS. 5A and 5B. However, foot positioner 620 provides rotation of the foot only, without angulation. Both types of foot positioners have utility based upon various factors such as, but not limited to, surgeon preference, type of procedure, condition of patient, etc.

Figure 7:
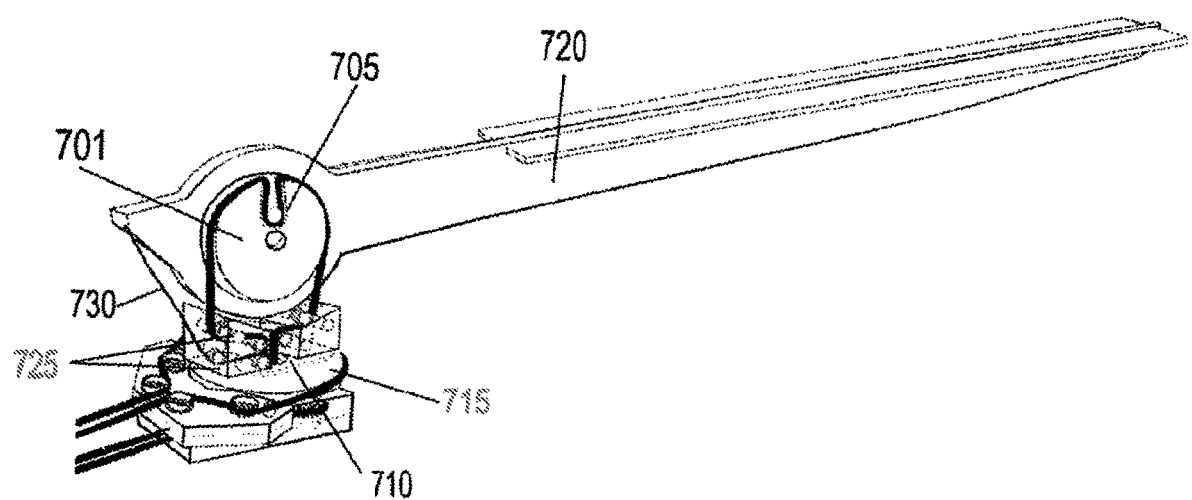
FIG. 7 is an exploded view of the inner components of an exemplary vertical turntable hub from an anatomic positioner, in accordance with an embodiment of the present invention.

FIG. 7 is a side perspective view of the inner components of an exemplary turntable hub from an anatomic positioner, in accordance with an embodiment of the present invention. In the present embodiment, the hub comprises a nonmetallic open cable windlass 701 with 180 degrees of rotation and a cable attachment point 705 at 12 o'clock. It is contemplated that in other embodiments or circumstances related to various different limbs and joints the optimal degree of rotation can be anywhere up to 360 degrees with either a sealed or an open windlass and with the cable attachment point in a multiplicity of suitable locations, for example, without limitation, at 8 o'clock or 1 o'clock, or any other setting which allows for full travel of the positioner with enough cable length to allow for concurrent angulation of joints along the limb or other extremity. In the present embodiment as depicted, cable windlass 701 interconnects thru a foramen opening 710 located at the centerpoint of a horizontal windlass to a powered winch (not shown) which controls vertical motion of a boom 720 thru the action of reeling and unreeling.

Sealed, channeled pulley blocks 720 with nonmetallic roller bearings 725 are arranged under vertical windlass 705 in such a fashion so as to communicate vertical motion to vertical windlass 705 thru foramen opening 710, which enables the actuation of cables to be achieved thru a swiveling base, horizontal windlass 715. Nonmetallic bearings may be made of a multiplicity of suitable materials such as, but not limited to, ceramic or various different plastics. Carbon Fiber, Polyethylethylketones (PEEK), DELRIN acetal polymer, TORLON polyamide-imide, PES Carbon Composite, as well as a plethora of other high performance polymers such as, but not limited to, Polyphenylene Sulfides, Polyetherimides, and Polyaryletherketones, as well as an array of emerging carbon fiber reinforced thermoplastic and polymer composites. Thru the action of the rotating vertical windlass 701 and horizontal windlass 715, boom 720 may allow for replication of the full range of motion of the human leg. A counterbalancing cable 430, which attaches to the trailing edge of boom 720 within the rotating windlass hub and passes thru foramen opening 710 via channeled pulley blocks 725, proceeds to an adjustable or non-adjustable spring reel or spring reels, which act as a counterbalance to boom 720. Using another simple pulley block, in some embodiments the spring reel tension cables may be directed thru the foramen opening in the same manner as the counterbalancing cable which may enable the spring reels to be located inside the operating room table or outside the operating room table. Placing the spring reels outside the operating room table may enable metallic spring reels to be used in configurations in which complete nonmetallic construction is desired, for example, without limitation, in the evolving Hybrid OR suite or in order to afford complete access to the entire patient and patient platform within the imaging bore, cone beam or other metal sensitive imaging platforms.

Figure 8:
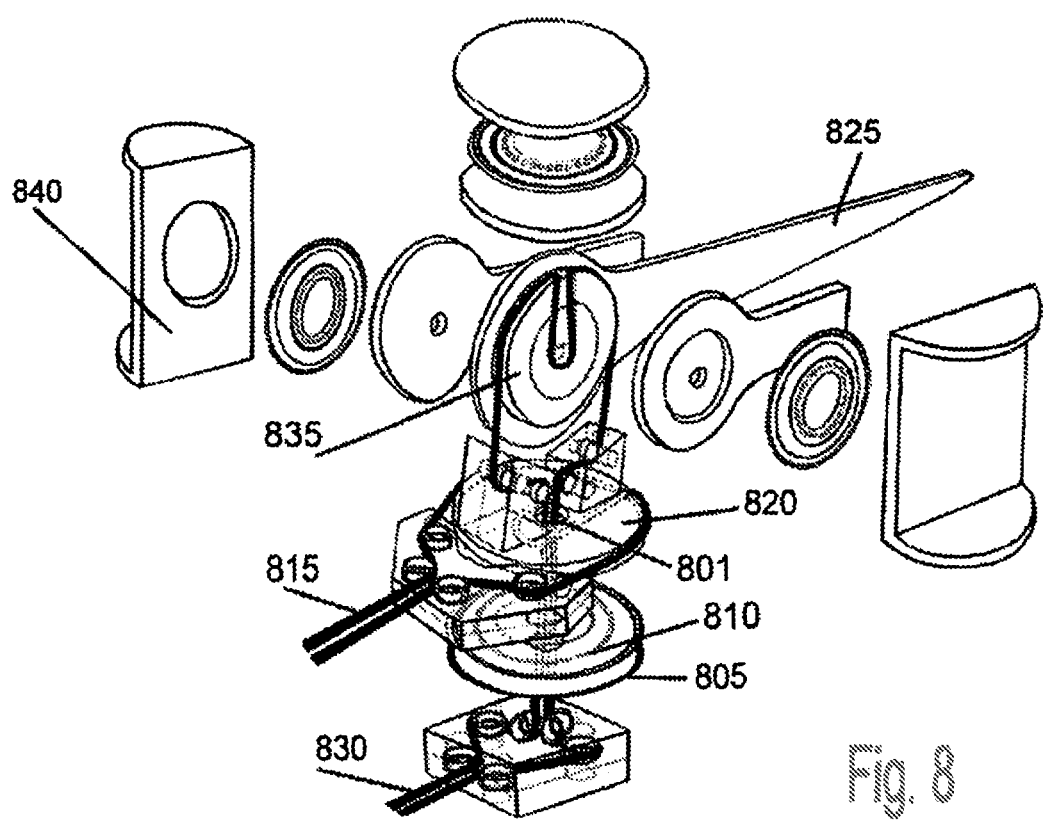
FIG. 8 is an exploded view of an exemplary turntable hub for an anatomical positioner, in accordance with an embodiment of the present invention.

FIG. 8 is an exploded view of an exemplary turntable hub for an anatomical positioner, in accordance with an embodiment of the present invention. A foramen type opening for cables typically cannot work correctly with the usage of an axel. Therefore, in the present embodiment, the hub comprises turntable bearings rather than axels which typically provide full and effortless rotation, while sharing any load across a wider segment than the inherent stress point which an axel represents and while also allowing transmission of cable actuation thru a foramen opening 801. Horizontal turntables 805 rotate upon nonmetallic bearings 810 when actuated thru the bi-directional action of a winch reeling cable 815.

A nonmetallic, cable actuated turntable 820 may be able to provide horizontal control of a boom 825. Sealed, channeled pulley blocks 830 comprise bearings embedded within a solid encasement of a synthetic material such as, but not limited to, Delrin®, which self-lubricates, similarly to the construction of a skateboard wheel. Those skilled in the art will readily recognize, in light of and in accordance with the teachings of the present invention, that pulley blocks may be made of a multiplicity of suitable materials such as, but not limited to, all manner of polymers, etc. Carbon Fiber, Polyethylethylketones (PEEK), DELRIN acetal polymer, TORLON polyamide-imide, PES Carbon Composite, as well as a plethora of other high performance polymers such as, but not limited to, Polyphenylene Sulfides, Polyetherimides, and Polyaryletherketones, as well as an array of emerging carbon fiber reinforced thermoplastic and polymer composites. In the present embodiment, A nonmetallic cable 830 communicates thru foramen opening 801 in order to deliver motive rotational force to a vertical windlass 835 attached to boom 825. Nonmetallic cable is used in the present embodiment, not only because it does not interfere with the imaging array, but also because nonmetallic cable exhibits superior strength to metallic cable typically without the stretching or sagging that is often associated with metallic cable fatigue. It is contemplated that various different types of cables may be used in some alternate embodiments such as, but not limited to, metallic cable, rope, rubber belts, etc.

In the present embodiment, vertical support members 840 comprised of high strength laminar sheets are placed on either side of the vertical windlass 835 to compress boom 825 and vertical turntables 845 between lateral supports 850 thereby providing strength thru right-angled, one-piece, laminar constructed support members 840. Support members 840 may provide buttressing to the sides of the hub and comprise ends that are bent to 90 degree so that supports 840 may be secured to bottom horizontal turntable 805 and to a top horizontal turntable, which could then be incorporated into an operating room table or to a modular Design. Nonmetallic PEEK and synthetic screws and fasteners, may be used in some embodiments to hold some of the components of the positioner together, have been omitted throughout the enclosed drawings and can be assumed as needed.

Figure 9:
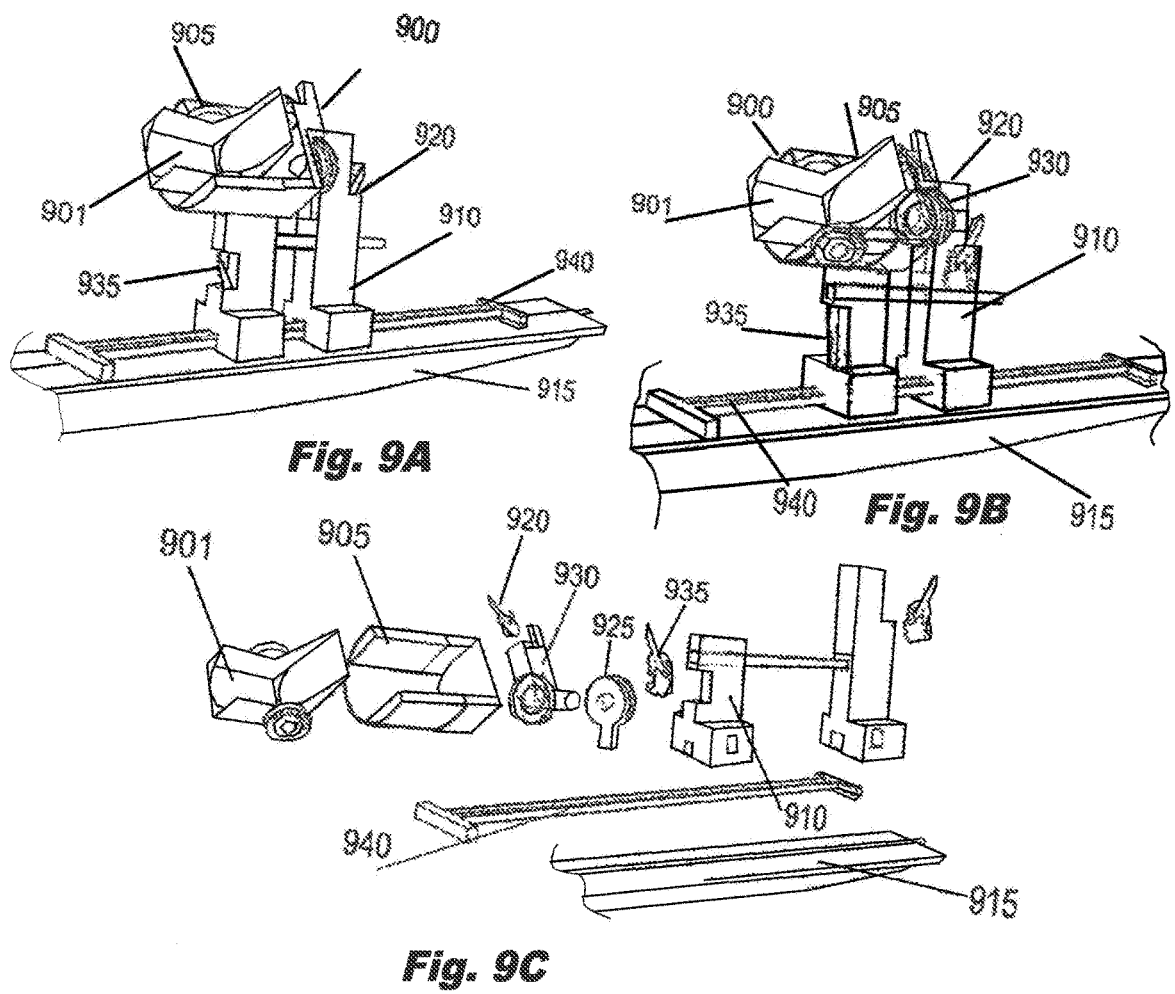
FIGS. 9A through 9C illustrates an exemplary leg positioner that may provide rotational angulation traction and distal caudal migration of the foot, in accordance with an embodiment of the present invention.

FIGS. 9A through 9C illustrates an exemplary leg positioner 900 that may provide rotation, angulation, traction and distal caudal migration of the foot, in accordance with an embodiment of the present invention. FIG. 9A is a side perspective view. FIG. 9B is a transparent side perspective view, and FIG. 9C is an exploded view. In the present embodiment, the motion of leg positioner 900 may allowing for anterior hip arthroplasty under full imaging conditions along the entirety of the limb, the hip, and the entire foot, which may be of enormous benefit for trauma cases and knee surgery when leg positioner 900 is advanced with the foot angulation set to recline. Hand controls 901 may provide one handed control of leg positioner 900 with automatic hands free locking.

Leg positioner 900 comprises an inner boot 901 which, with a (PEEK) spring loaded detent, allows for angulation from where the toe points straight up to full extension of the foot with toe flexion away from the body as much as possible. Boot 901 typically fits inside a rotational outer boot 905, which rests upon bearings located in a bidirectional leg positioning shuttle 910, such that the weight of the patient's leg is communicated to a counterbalanced boom 915. A spring actuated lever 920 allows for circumferential 180 degree rotation of rotational outer boot 905 when squeezed, as this action allows for a toothed block to free itself from a circumferential rack 925. Lever 920 is firmly fixed a top portion of shuttle 910. A housing 930 for lever 920 may be mounted to the sole of outer rotational boot 905, such that when lever 920 is depressed, the entire rotational boot 905 can rotate a full 180 degrees left or right and to lock automatically in place when lever 920 is released. A lever 935 acts as the actuation for bi-directional leg positioning shuttle 910, which travels along a slotted rack 940 allowing for positioning of the leg fully extended, with the knee bent, or anywhere in between these two positions for any sized patient. Some embodiments may comprise ceramic roller bearings at the bottom shuttle 910 to allow for virtually effortless migration of the leg distally or caudally when lever 935 is actuated, and a three pronged block drops into slotted rack 940, thereby retarding motion of shuttle 910 in either direction when lever 935 is released. The two vertical members of shuttle 910 communicate with each other via an additional slotted rack 945 firmly fixed to the upper portions of the members such that lever 920 remains locked into position atop shuttle 910 so that the taller member of shuttle 910, the traction member for the lower extremity, is slaved to the bidirectional control of the shorter member of shuttle 910. After bidirectional shuttle 910 is locked into place, lever 920 may be actuated as necessary in order to provide distal traction, as would be necessary during anterior hip arthroplasty, wherein the femur is subjected to intra-operative traction in order to expose the femoral head, so that it may be implanted with an artificial femoral shaft, or secured temporarily with a femoral hook, for example, without limitation, a hook able to be mounted to the housing of the leg positioner at the rotating Hub Assembly comprising the turntable bearings. When positioned more proximally, towards the patient's core, bidirectional positioning shuttle 910 and angulation inner boot 901, allow for knee revision surgery. When Fully extended a pair of leg positioners may have both of the rotational boots pointed in the same direction, with one leg positioner situated directly above the other, such that full lateral positioning of the patient is possible as well.

Figure 10:
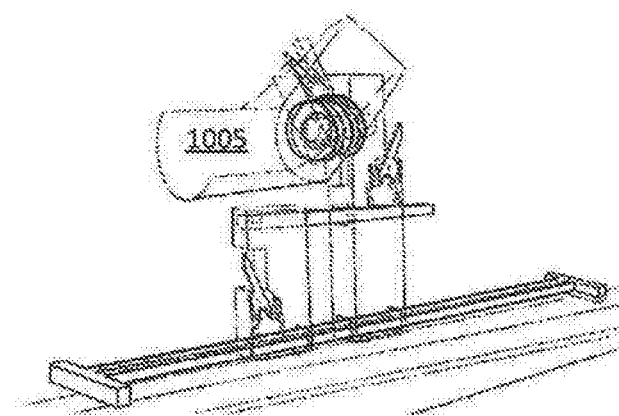
FIG. 10 is a transparent side perspective view of an exemplary leg positioner, in accordance with an embodiment of the present invention.

FIG. 10 is a transparent side perspective view of an exemplary leg positioner, in accordance with an embodiment of the present invention. In the present embodiment, the leg positioner comprises a rotational traction boot assembly 1005 without means for angulation.

Figure 11:
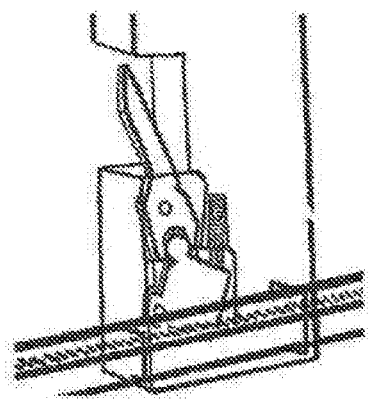
FIG. 11 is a partially transparent side perspective view of an exemplary hand actuated trigger with automatic hands free braking as incorporated into a leg positioner or traction rotational and angulation boot, in accordance with an embodiment of the present invention.

FIG. 11 is a partially transparent side perspective view of an exemplary hand actuated lever with automatic hands free braking as incorporated into a leg positioner or traction rotational and angulation boot, in accordance with an embodiment of the present invention. In the present embodiment, the lever actuates a pronged block so that the prongs of the block are engaged or disengaged from a rack comprising means with which the prongs may engage such as, but not limited to, slots, teeth, grooves, holes, etc. When an operator actuates the lever the block is pulled away from the rack so that the shuttle may slide freely along the rack, and when the operator releases the lever a spring or another type of mechanical force pushes the block back into engagement with the rack so that the shuttle is locked in place.

FIGS. 12A through 12C illustrate an exemplary anatomical positioner that may be actuated by a caliper and rotor system, in accordance with an embodiment of the present invention. FIG. 12A is a side perspective view. FIG. 12B is an exploded side perspective view, and FIG. 12C is an exploded view of a turntable hub portion of the positioner. In the present embodiment, the positioner is entirely non-metallic from the level of the patient's abdomen and lower, thereby generally allowing full access within the imaging bore of a variety of imaging technologies including, without limitation, Fluoroscopic C-arms or Cone beam Computer assisted Tomagraphy as exemplified by the 0-arm, typically without contributing metal streak or density artifact, or the so called "Black Hole" Artifact due to high attenuation objects in close proximity to various means of intra-operative patient imaging.

Some embodiments implementing calipers and rotors may comprise a minimal amount of metal components if constructed so as to utilize either Stainless Steel or Aluminum in the construction of a slotted brake rotor and caliper interface. This should usually present no problem to the intra-operative imaging of the entire hip, leg, knee and foot. The present embodiment may be particularly useful for providing universal access to the newly emerging anterior hip arthroplasty approach, which typically shortens recovery time when compared to the lateral hip arthroplasty approach, which severs major muscles necessitating prolonged recovery. Unfortunately, thus far, the anterior approach has often required hospitals to purchase expensive specialty orthopedic operating tables in order to effect this anterior approach. As such, this anterior hip arthroplasty approach is generally not available except to those with access to teaching hospitals or to the affluent.

The present embodiment teaches a method and apparatus for fashioning a portable modular component which may enable any conventional patient platform or hospital operating room table, to be converted in minutes into a specialty orthopedic operating table for surgical procedures of the lower extremities by merely rolling a portable anatomical positioning component to the foot of a conventional operating room table, adjusting for height and, hooking an attachment to the ubiquitous and standardized accessory side rails with which the overwhelming majority of operating room tables are either equipped with, or may be equipped with in less than one minute, thereby allowing access to this specialty procedure at virtually any hospital, even to those sites of limited financial means. Additionally, the present embodiment typically accomplishes this feat while generally eliminating all metallic components from interference with imaging of the patient anatomy from the hips thru the foot, while concurrently providing effortless counterbalancing of the weight of the lower extremity, as well as extreme ease of use thru a simple one position actuator and automatic hands free braking system for positioning of the lower extremity throughout the x, y, and z coordinates as necessary for surgical access. In the present embodiment, the modular rotor caliper actuated lower extremity positioner may be readily to incorporate either atop a small roll-around wheeled assembly equipped with a simple scissor lift and a side rail mount such that any conventional operating room table could readily be converted into a hip and knee specialty surgical table in a matter of minutes or may be ready to be incorporated into a dedicated table featuring iterations of these same rotor caliper patient positioning paradigms configured so as to position not only the lower extremities, but the upper extremities and the head as well all featuring effortless one handed positioning of all extremities utilizing inherently counter balanced, one handed, automatic braking. Some embodiments may be fully nonmetallic if configured with polymer calipers and slotted rotors, which is achievable in that the inherent counterbalance typically transforms the lever action of these designs into a state of balanced equilibrium, whereby the mechanical advantage represented by metallic components at key stress points such as, but not limited to at the caliper rotor interface may be eliminated. Other embodiments may comprise a caliper portion and a slotted rotor which directly interfaces said caliper portion of the apparatus that utilize a minimum amount of non-ferro magnetic metals within the hub, such that no metal or high attenuation, streak or black hole artifact presents during imaging.

FIG. 12C illustrates an exemplary lower extremity boom 7c comprised of a flat laminar sheet of carbon fiber, fixated to a flat laminar sheet with a 90 degree bend and buttressed on either side by smaller secondary booms 7d and 7e which provide lateral support to the assembly at the interface between boom 7c and the turntable hub assembly. Secondary booms 7d and 7e concurrently house flat ceramic turntable bearings 7x and 7y, although other suitable non ferro magnetic materials such as, but not limited to, Delrin® may be readily utilized. Said vertical turntable bearings 7x and 7y are sandwiched between two lateral supports 7f and 7e which fit between a bottom horizontal turntable bearing 7g and a top horizontal turntable bearing 7h and functionally represent "wheels rotating within wheels", thereby allowing full positioning of the entire boom assembly which replicates the anatomical positioning of the patient's leg.

FIG. 12C also illustrates an exemplary horizontal turntable slotted rotor. FIG. 7 xyz illustrates the slotted rotor which demonstrates optimal placement of this horizontal rotor such that it rotates circumferentially thru an open slotted caliper 7t when a hand actuator 7xx is squeezed by the operator during counterbalanced maneuvering of limb positioning boom 7c, and which then interfaces automatically as the slotted grooves interconnect along the entire interior of mounted horizontal caliper 7t, meshing the caliper and the Slotted rotor and thereby halting all rotation and automatically braking all motion of the limb as soon as the operator releases actuator 7xx. 7w illustrates a counterbalancing Spring reel (adjustable tension or non adjustable) which provides mechanical equilibrium via contributing constant downward force to the load end of the mechanism at the load end of the natural lever at position 7*xl*. 7*v* illustrates the vertical caliper.

It is contemplated that some embodiments may implement virtually any manner of caliper brakes and other types of brakes including, without limitation, hydraulic brakes hub brakes, drum brakes, etc. Even though hydraulic brakes typically require metallic lines, embodiments using hydraulic brakes may use a hand control to cable actuate a separate controller that actuates the hydraulic lines, which may be within the turntable hub, within the center of a table attached to a free spinning winch, outside of the room attached to powered winches, etc. In some embodiments the rotors may be implemented as flat sheets of material that are positioned between the turntables at the hub which are then linked to a stacked series of calipers that are all controlled via hand control units, such that the hand control units may control three calipers on the horizontal turntable and three calipers on the vertical turntable simultaneously. In some embodiments a parking brake rotor may be employed. Those skilled in the art will readily recognize, in light of and in accordance with the teachings of the present invention, that some fully nonmetallic embodiments with counterbalancing may feature nonmetallic caliper rotor tension band brakes with nonmetallic counterweights based upon the implementation of tension bands rather than springs. Additionally, such a nonmetallic caliper rotor arrangement could readily be utilized to augment cable windlass actuated embodiments with a secondary means of braking that is slaved to the primary means. Such as, but not limited to, a double braking system represented by a cable windlass/free spinning winch caliper closed system. In this non-limiting example, one caliper can control the free spinning winch located within the operating room table housing while another caliper may control the cable windlass itself within the turntable hub to create failsafe braking.

Figure 13:
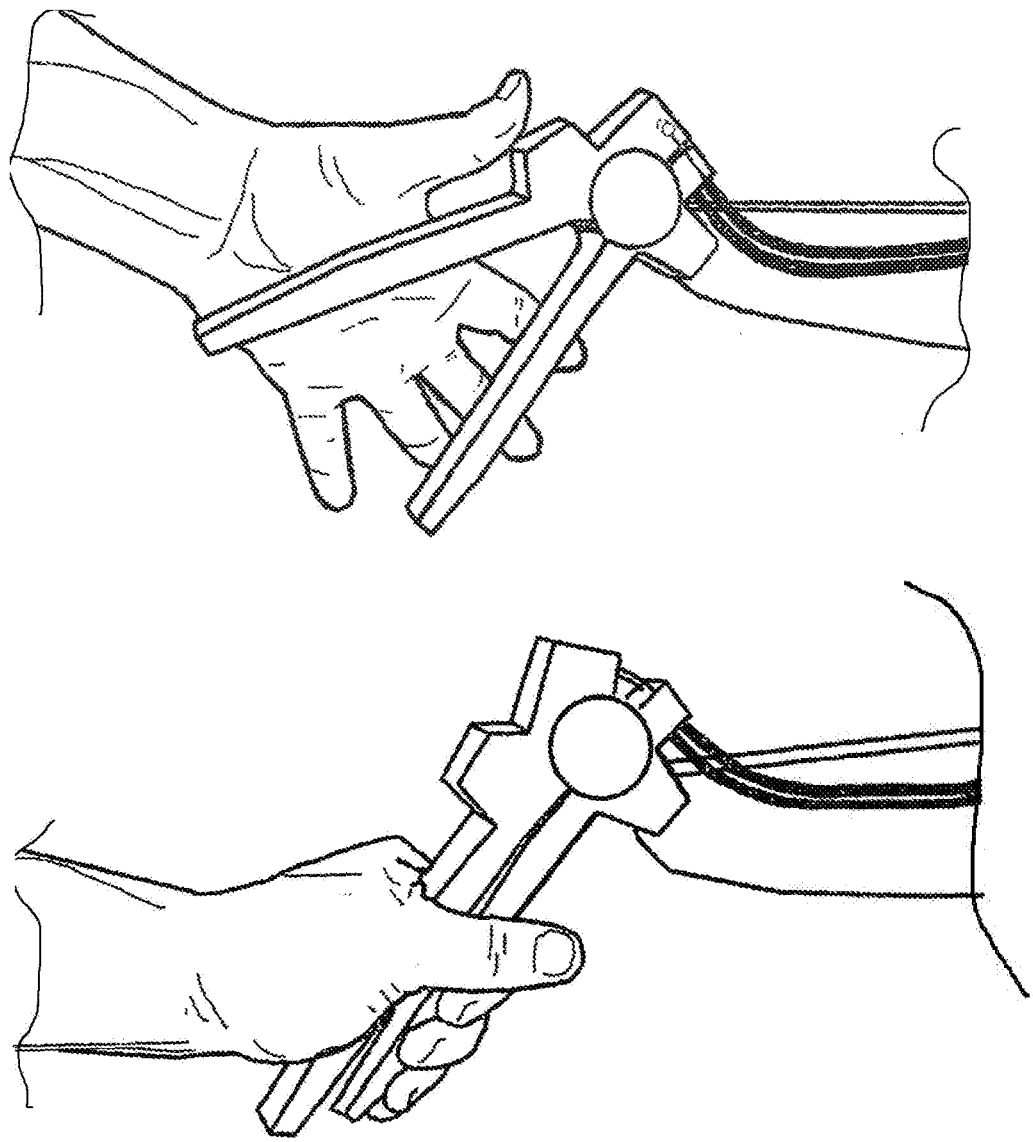
FIG. 13 illustrates an exemplary hand control unit comprising a lever able to harness one thru several control cables simultaneously so that horizontal and vertical directional control can be performed simultaneously with automatic hands free braking as soon as the hand control is released, in accordance with an embodiment of the present invention.

FIG. 13 illustrates an exemplary hand control unit comprising a lever able to harness one or several control cables simultaneously so that horizontal and vertical directional control may be performed simultaneously with automatic hands free braking as soon as the hand control is released, in accordance with an embodiment of the present invention. In lower extremity positioners, vertical and horizontal directional controls are typically managed simultaneously, whereas in head positioning caliper rotor embodiments, vertical adjustability is usually coordinated and actuated thru a vertical windlass, with a separate inner caliper rotor controlling angulation at the elbow of the positioner, such that the patient's head may be angled and arranged vertically and horizontally into the most advantageous position for surgical access. Concurrently, tilt and angulation of a skull clamp affixed to the head positioner is typically controlled thru a separate free spinning rotor controlling a parallelogram, such that three individual controls may be slaved to the hand control unit. Furthermore, in a cable windlass version of the head control unit with said cable windlass arrangement able to spin freely when the hand control allows the caliper to release a rotor which is connected to the cable winch, these same three directional controls may be coordinated thru the a single hand control.

Figure 14A:
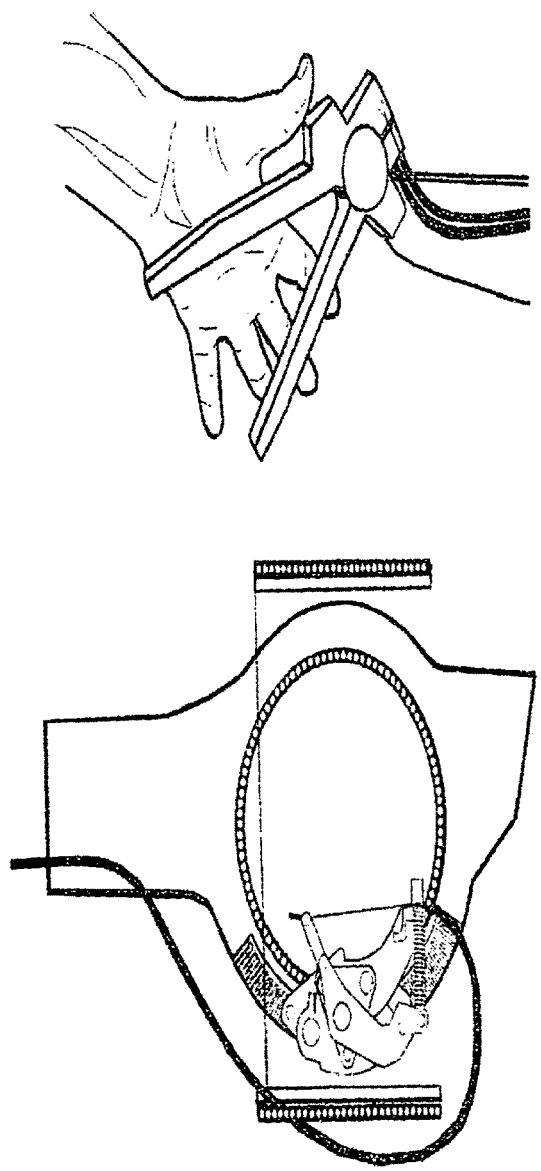
FIGS. 14A and 14B illustrate the spring action of an exemplary caliper rotor assembly with an intermeshing slotted rack in the automatic locking position, in accordance with an embodiment of the present invention.
Figure 14B:
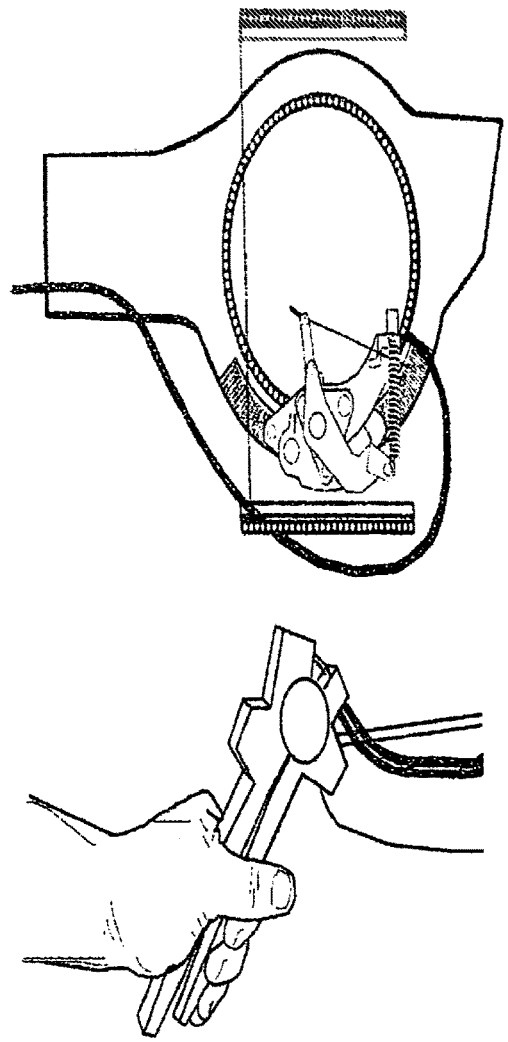

FIGS. 14A and 14B illustrate the spring action of an exemplary caliper rotor assembly with an intermeshing slotted rack in the automatic locking position, in accordance with an embodiment of the present invention. FIG. 14A shows a closed caliper with the hand control released, and FIG. 14B displays an open caliper with the hand control engaged allowing full position-ability. Referring to FIG. 14B, note the Spring is stretched via the action of the operator grip upon the hand control thereby pulling the cable. In the present embodiment, up to 4 rotor/caliper assemblies may be stopped with this design thereby controlling vertical motion, horizontal motion, angulation, and tilt thru a parallelogram as seen in the head control unit as well as in an elbow unit with full 90 degree angulation with the upper arm positioned anywhere from full ascending vertical to full descending vertical. The position of the spring in the caliper typically enables the spring to snap shut at the caliper allowing the hand control unit to be implemented without a spring.

Figure 15A:
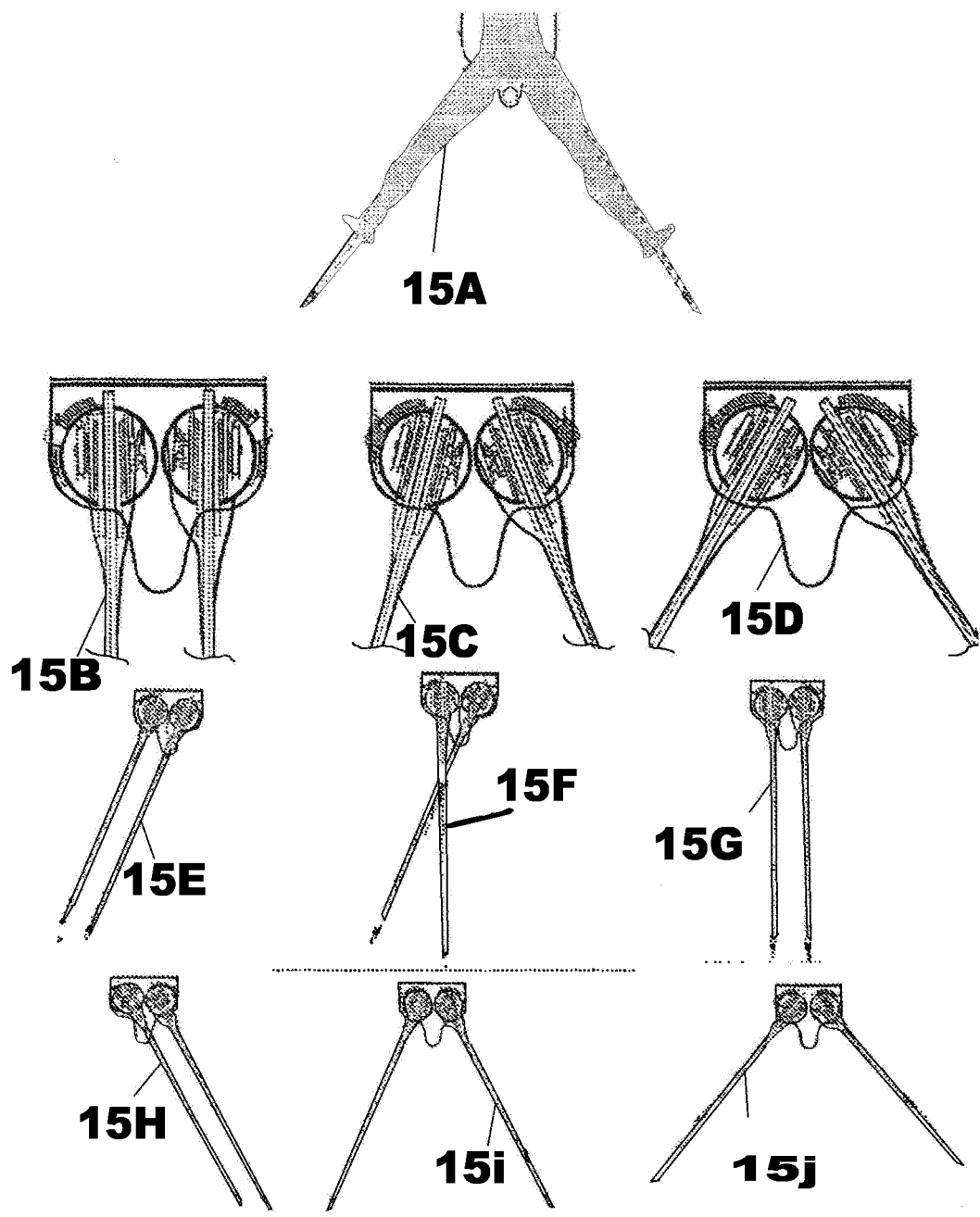
FIG. 15A displays the full range of HORIZONTAL motion available to an exemplary caliper rotor iteration of a leg positioner in 15A-15J, in accordance with an embodiment of the present invention.
Figure 15B:
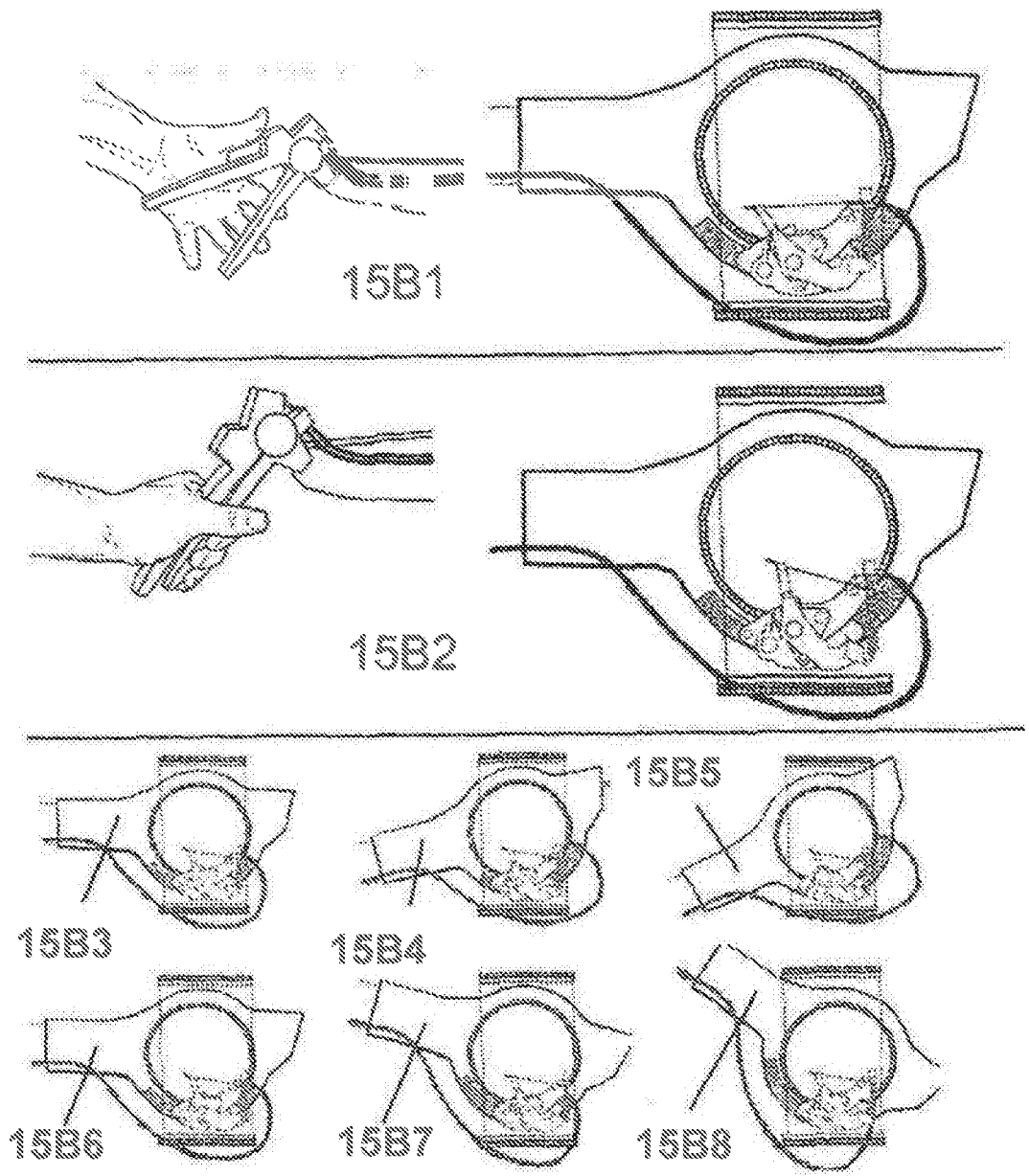
FIG. 15B displays the full range of VERTICAL motion available to an exemplary caliper rotor iteration of a leg positioner in 15B1-15B8 in accordance with an embodiment of the present invention.

FIG. 15A displays the full range of HORIZONTAL motion available to an exemplary caliper rotor iteration of a leg positioner in 15A-15J. FIG. 15B displays the full range of vertical motion available to an exemplary caliper rotor iteration of a leg positioner in FIGS. 15B1-15B8, in accordance with an embodiment of the present invention. Thru a slotted top and bottom turntable, nearly vertical positioning may be achieved with an exemplary arm positioner. See the arm positioner as illustrated by way of example in FIG. 21B.

Figure 16:
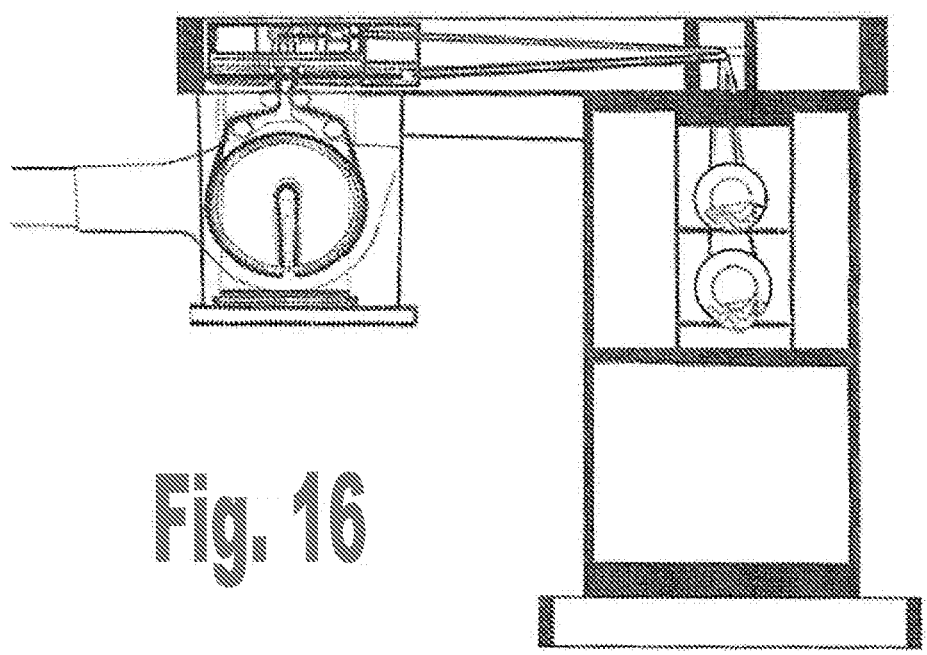
FIG. 16 illustrates an exemplary caliper windlass hybrid system with hand control actuation, in accordance with an embodiment of the present invention.

FIG. 16 illustrates an exemplary caliper windlass hybrid system with hand control actuation, in accordance with an embodiment of the present invention. In the present embodiment, an entire or table may be outfitted with fully nonmetallic leg, arm and head positioners, with the only metal components being the caliper rotor attached to the free spinning winch within the hub of the table. With the correct counterbalancing, an entirely nonmetallic rotor caliper may be constructed in that, rather than hold the weight as most companies do with ball joints. the perfectly balanced equilibrium of the counterbalanced positioners as laid forth according to method described in embodiments of the present invention allow that the braking rotor caliper need only arrest windlass rotation as opposed to holding the actual weight.

FIG. 17 illustrates exemplary rotor caliper equipped free spinning winches located within the hub of an operating room table, in accordance with an embodiment of the present invention. In the present embodiment, the location of the winches may increase the zone in which no metallic components are located to encompass nearly the entire patient.

FIG. 18 illustrates an exemplary caliper cable rotor hybrid system in use positioning in a Trendelennberg and a reverse Trendelenberg modality, in accordance with an embodiment of the present invention.

Figure 19A:
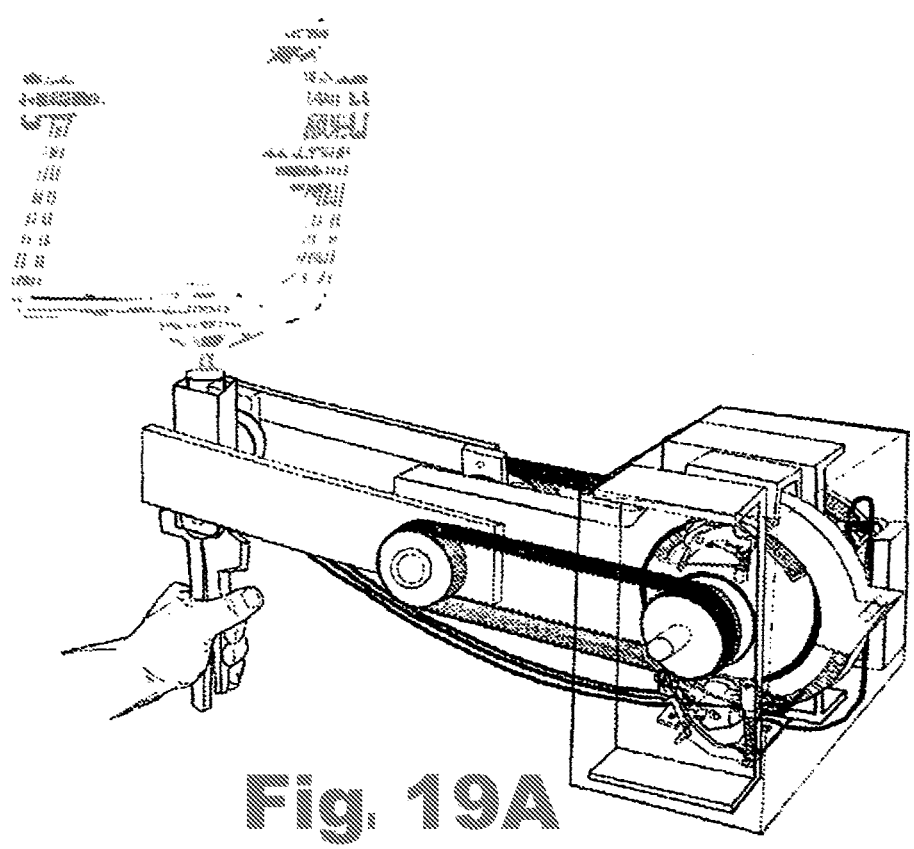
Figure 19B:
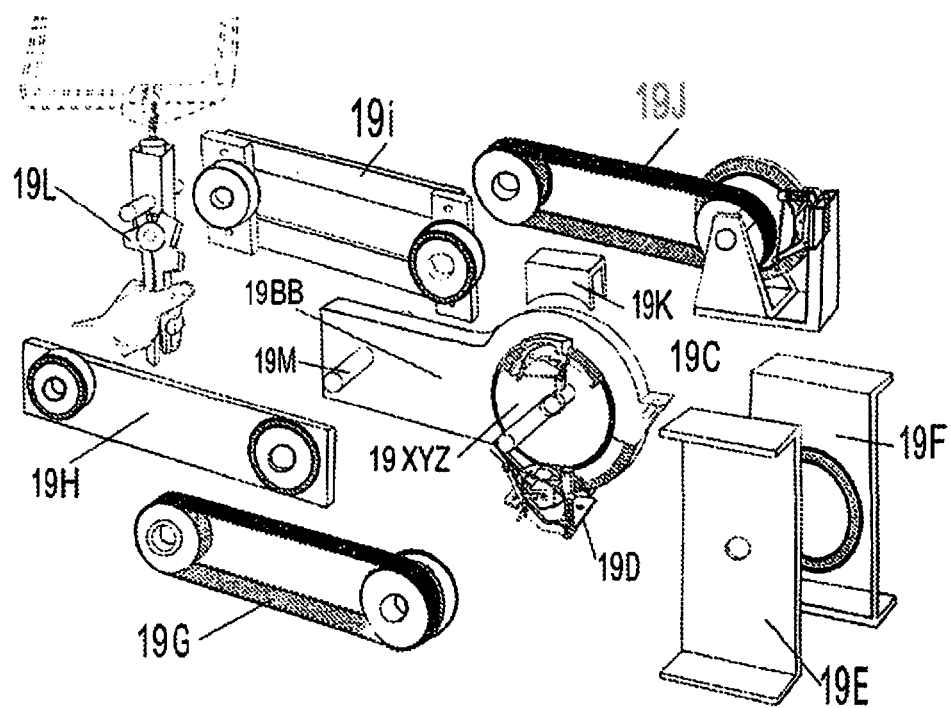

FIGS. 19A through 19C illustrate an exemplary hand operated radiolucent and primarily nonmetallic head positioner, accordance with an embodiment of the present invention. FIG. 19A is a side perspective view. FIG. 19B is an exploded view, and FIG. 19C illustrates the range of motion of the head positioner. In the present embodiment, the positioner may be used for neurosurgery and may be universally compatible with a wide variety of currently available skull clamps. As opposed to a positioner that comprises a multiplicity of screws to tighten by hand for adjustment, the present embodiment may achieve virtually effortless one handed positioning of both verticality and elongation, with an elbow bend able to maneuver thru 90 degrees of angulation, concurrent to an upper arm portion 11BB able to be manipulated to nearly vertical in both the ascending and descending modes and also featuring the ability to simultaneously control the exact angle of the skull clamp with automatic braking upon release.

Referring to FIG. 19B, a hand controlled caliper rotor interface is able to control positioning of upper arm assembly 11BB thru a range from 11 o'clock to 7 o'clock. Internal to this rotating vertical rotor, is a separate rotor caliper which rotates around a guide axel and is afforded stability thru a turntable bearing support 11*f* and a rotor guide 11K. Actuation of hand control 11L and the attached cable actuates the release of the calipers, with support of the head (average weight 10 lbs.) generally provided by the operator as the head is raised and positioned vertically or horizontally and away or towards the table with the assembly responding automatically to this positioning motion via alteration of the angulation of the Elbow turntables located on an articulating support 1*lh* and a Parallelogram support 1*li* with automatic locking of all calipers immediately upon release. Angulation of the skull clamp in a universal support member attached to hand control unit 1*l*L is effected via a free spinning caliper attached to the Parallelogram support 1*li* via a belt drive 11*j*. In some embodiments, the free spinning caliper and the parallelogram support may be connected by a cable windlass as illustrated by way of example in the Leg Positioning embodiment. The free spinning caliper rotor 11 xyz is able to mirror the positioning of a free spinning elbow belt drive 11*g*, with both connecting at a free spinning elbow joint 1*lm* as the entire assembly is positioned vertically, elongated, and bent at the elbow with wrist control of the tilt of the skull clamp attached to hand control unit 1*l*L effected via mirror image positioning of parallelogram support 1*li* as it rotates at elbow joint 1*lm* and causes belt drive 1*lj* and parallelogram support 1*li* to lock the tilt of the skull clamp when hand control unit 1*l*L is released. Referring to FIG. 19C, this mechanism is shown as the head positioner is positioned in various different configurations, with skull clamp tilt mirrored by the free spinning rotor of the skull clamp until the mechanism is locked by the release of hand control unit 11L.

Figure 20A:
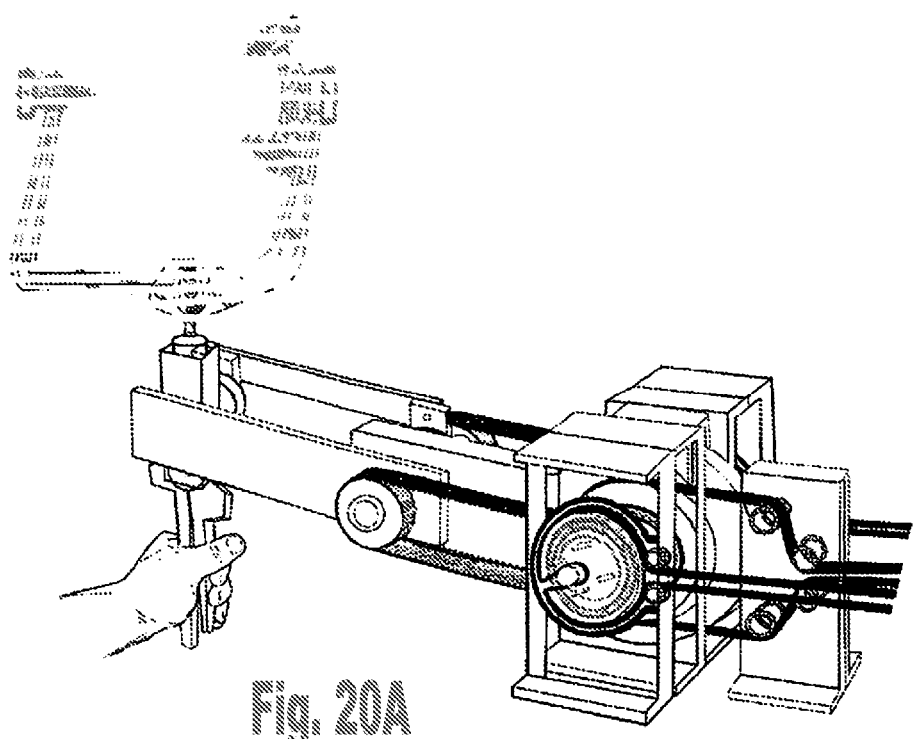
FIGS. 20A and 20B illustrate a head positioning unit employing a cable windlass system in accordance with an embodiment of the present invention.
Figure 20B:
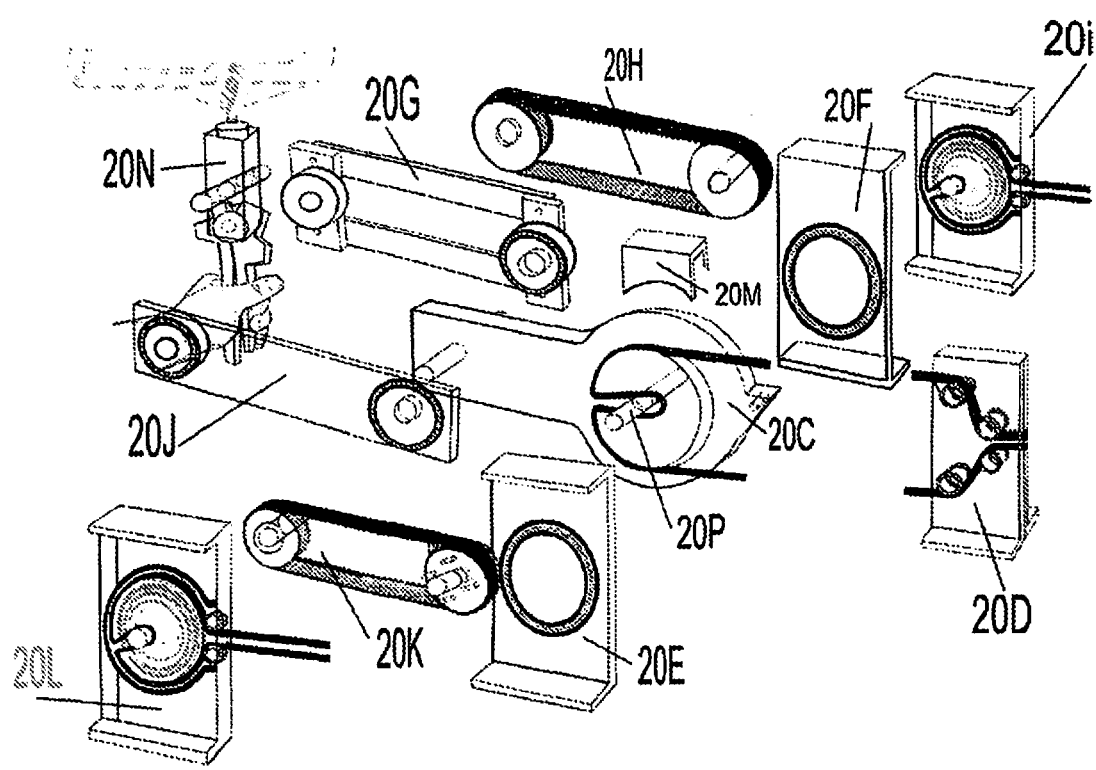

FIGS. 20A and 20B illustrate an head positioning unit employing a cable windlass system, in accordance with an embodiment of the present invention. FIG. 20A is a side perspective view, and FIG. 20B is an exploded view. In the present embodiment, the variable head positioning unit comprises an upper arm portion 12*c* with an attached windlass and nonmetallic cable threaded thru said windlass. A guide axel 12*p* is located thru and within the windlass and is free spinning due to a bearing surrounding guide axel 12*p*. Sealed and channeled pulley blocks 12D comprise an arrangement of the internal, free spinning bearings that may direct the ingress and egress of the nonmetallic windlass cable to the control winch. Vertical buttresses 12E and 12F are equipped with nonmetallic turntable bearings such that upper arm 12*c* may rotate vertically within the housing created by buttresses 12E and 12F. A swiveling control member 12*n* is attached to a hand control unit. Alternately, in a cable windlass/caliper controlled winch iteration, the hand control unit may be eliminated from consideration in the remotely controlled powered option of the head positioner. In the present embodiment, swiveling control member 12*n* is equipped with an axel which connects firmly to the leading edge of a parallelogram 12*g*, thereby transmitting the tilt of swiveling member 12*n* an elbow portion of parallelogram support 12*g*. The tilt of swiveling member 12*n*, having been transferred to the elbow of parallelogram support 12*g*, is then transmitted to the leading edge a belt drive 12*h* such that as swiveling member 12*n* tilts, this action is mirrored by an identical tilt at the leading edge of belt drive 12*h* which is then transmitted to the trailing edge of belt drive 12*h* via the action of the belt as it rotates in sequence to the tilt of member 12*n*. The tilt is then transmitted to a sealed windlass 12*i* . . . which is unconnected to upper arm assembly 12*c* and 12*f*. Thereby sealed cable windlass 12*i* is typically able to slave its vertical positioning up and down to the vertical action of the upper arm since these members remain connected at the elbow. Said vertical motion is then replicated thru equivalent upward and downward rotation of sealed cable windlass 12*i*. Simultaneously, any angulation or tilt of member 12*n* is also communicated to sealed cable windlass 12*i*.

Sealed cable windlass 12*i* typically allows for a 340 degree rotation before further rotation is halted via the cable attachment to windlass 12*i*. Said Cable attachment point to windlass 21*i* is clearly depicted as attaching to windlass 21*i* at the 8 o'clock position with the ingress and egress of the cable departing and entering a windlass 12L at the 3 o'clock position. This has been set as such in order to mirror windlass 12L, which connects to a belt drive 12*k* in order to actuate a full 90 degree bend of the elbow and typically allow a full bend to transpire throughout the entire vertical range of motion of the entire arm. In order to allow for a full 90 degree bend at the elbow joint, it is believed that should a windlass with only a 180 degree rotation be used, said windlass will only slightly bend at the joint before it seizes up, thereby acting as a brake to the entire mechanism of the positioner. As such, in the present embodiment, a Windlass with a 340 Degree rotation is used in the form of the sealed windlass design whereby Windlass 12L rotates via a connection to a turntable bearing situated within a channel placed inside windlass 12L. Additionally, it is believed (without limitation) that the placement of the cable attachment point in a location other than 8 o'clock may cause windlass 21*i* to have insufficient cable travel to allow the full 90 degree upward bend. Were this to be arranged as a leg positioner the same configuration may be followed with the exception that the cable entry point into the windlass would be located at the 10 o'clock coordinate thereby allowing for a 90 degree downward knee bend, which may be necessary for a Lithotomy positioner.

Arranged as such, the head positioner which may be hand controlled or remote controlled. In the hand controlled iteration support of the head during positioning as well as angulation at the elbow joint and upward and downward motion of the skull clamp inserted into swiveling member 12*n* may all be actuated by an operator grasping a hand control unit 12*n*, and thereby the controller may adjust the positioner for the exact tilt height and distance from the table smoothly and simultaneously with automatic braking upon release of hand control unit 12*n*.

FIGS. 21A1-21A12, FIGS. 21A, 21AA, and 21BB illustrate an exemplary upper extremity positioner actuated by a caliper rotor with a 90 degree elbow bend, in accordance with an embodiment of the present invention. FIG. 21A depicts an upper arm assembly 21F of upper extremity positioner with a counterbalancing cable 21P (See also FIG. 21BB) with a spring reel and is also mounted to the horizontal turntable base in FIG. 21AA, which displays the opposite side of the upper extremity positioner. Vertical travel of the upper arm assembly 21F is controlled via the intermeshing of a slotted rotor seen at the inferior edge of 21A, as said rotor travels through a caliper 21D when caliper 21D is released thru hand control 21*i* action at a lower arm assembly 21H, which also controls the release of a horizontal caliper 21N which intermeshes with a horizontal rotor 21M. Hand control 21*i* may also simultaneously release an inner elbow caliper/rotor mechanism 21C thereby allowing free spin of this inner caliper upon bearings and guides located around a guide axel 21E along with belt 21K and bearings 21G, which generally prevents the inner caliper from migrating sideways as it spins freely around guide axel 21E. A padded positioner 21J attaches to a raised carbon fiber fin atop lower arm assembly 21H.

Hand control actuation by the operator frees all calipers simultaneously allowing variable positioning of the patient's arm 21o anywhere in the x, y, and z coordinates while also allowing the elbow to bend a full 90 degrees upward. As such, the operator may lend some support to the elbow during positioning in order to generally prevent unwanted flexion of the elbow joint or the hand control unit may be equipped with two triggers with one trigger controlling both vertical and horizontal positioning simultaneously and a second trigger controlling the release of inner caliper 21C via an additional finger tap. In this manner, arm 21o may be positioned vertically and horizontally with separate elbow positioning to follow. Alternatively, all calipers may be released at once as the natural rigidity of the patient's arm 21o fastened into lower arm assembly 21H via straps will typically offer enough resistance to elbow bend such that the operator will have to push the hand control 21i unit forward at lower arm assembly 21H in order to commence the elbow bend. After the arm has been positioned satisfactorily, the release of the hand control unit will lock all members into position automatically.

Hand control actuation by the operator frees all calipers simultaneously allowing variable positioning of the patient's arm 130 anywhere in the x, y, and z coordinates while also allowing the elbow to bend a full 90 degrees upward. As such, the operator may lend some support to the elbow during positioning in order to generally prevent unwanted flexion of the elbow joint or the hand control unit may be equipped with two triggers with one trigger controlling both vertical and horizontal positioning simultaneously and a second trigger controlling the release of inner caliper 13c via an additional finger tap. In this manner, arm 130 may be positioned vertically and horizontally with separate elbow positioning to follow. Alternatively, all calipers may be released at once as the natural rigidity of the patient's arm 130 fastened into lower arm assembly 13i via straps will typically offer enough resistance to elbow bend such that the operator will have to push the hand control unit forward at lower arm assembly 13i in order to commence the elbow bend. After the arm has been positioned satisfactorily, the release of the hand control unit will lock all members into position automatically.

Referring to FIG. 21B, the full range of vertical positioning of arm positioner 21 is shown, which is approximately 170 degrees of vertical travel which falls Just short of perpendicular to the horizon with all of said positions able to be replicated along the entire 180 degrees of horizontal positioning. By replicating arm positioner 21 without a top turntable (with alteration to scale as well) and mounting such an apparatus at the end of a Patient bed after equipping said apparatus with a foot holder, the apparatus becomes a fully radiolucent and nonmetallic lithotomy positioner, which may be utilized for facilitating difficult births in the live imaging environment as well as for other image assisted procedures requiring such positioning. Moreover, the elbow may be further lifted to raise upwards as the boot arranged on a turntable swivel may autocorrect the knee angulation naturally so that this positioner could also be mounted atop a portable platform with a scissors lift for height adjustability thereby converting any patient operating room table into such a radiolucent lithotomy positioner to facilitate imaging of difficult and high risk births. Additionally, an entirely nonmetallic embodiment of such a lithotomy positioner could also be constructed along the same lines as described above via utilization of a cable windlass as the nonmetallic means of operation within the turntable hub with said cables then entering and spooling thru a pulley block arrangement onto a caliper rotor actuated, free spinning winch located under the turntable hub and above the scissors lift or on a dedicated table. Said free spinning caliper and rotor winch could be located within the base of the table. In this manner, the entire birth canal may be visualized without metal interference to the imaging array during high risk births.

Figure 22:
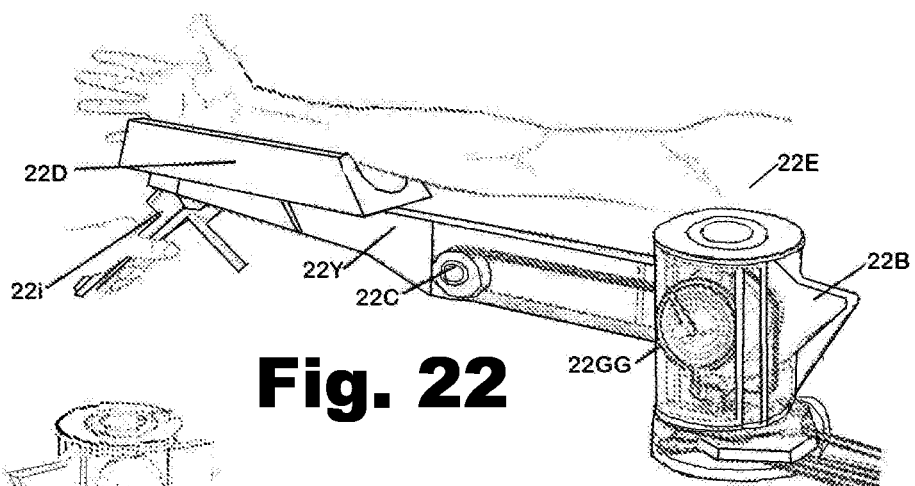
FIGS. 22, 22AA, 22BB illustrates an exemplary cable windlass actuated upper extremity arm positioner, in accordance with an embodiment of the present invention.
Figure 22A:
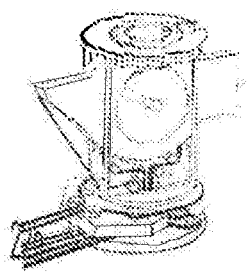
Figure 22B:
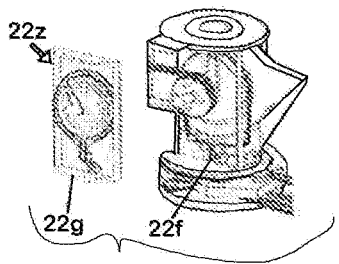

FIG. 22 illustrates an exemplary cable windlass actuated upper extremity arm positioner, in accordance with an embodiment of the present invention. In the present embodiment, the positioner may be hand operated 22i via the utilization of a caliper rotor assembly 22GG attached to a free spinning winch located within the center of the operating room table. The positioner may also be remotely controlled via communication of control cables with a control winch to be located outside of the operating room table. As can be, the cable windlass 22f of the upper arm portion 22D communicates cable travel thru a foramen opening located in the center of the horizontal windlass. A free spinning toothed hub 14z that transmits belt drive rotation to a structure 22g, which is another belt drive toothed hub which is pin connected to a forearm structure 22Y such that as forearm structure 22Y is bent to a 90 degree angle this motion is mirrored thru the action of the belt drive by the free spinning toothed hub 22Y which is pin connected to a sealed, free spinning cable windlass 22G such that as the elbow joint of hub 22C moves in unison with forearm structure 22Y. This movement causes sealed windlass 22G to spin accordingly. Free spinning windlass 22G also spins in concert with the vertical positioning of the upper arm along the entire 170 degrees (just short of perpendicular) vertical travel of the entire arm assembly such that a cable attachment point 22z shown in the default 10 o'clock position for the arm positioner when parallel to the horizon is seen to rotate clockwise to the 1 o'clock setting when arm 22E is positioned at the maximum 170 degrees of vertical (nearly perpendicular to the floor) setting. In this position, should the forearm then be moved to a full 90 degree upward bend, cable attachment 22z would be seen to rotate clockwise from the 1 o'clock position to the 4 o'clock position.

Similarly, the arm positioner to again be restored to the default setting, with cable attachment point 22z set at the 10 o'clock setting and the arm to be positioned at the maximum downward position, cable attachment point 22z would have rotated counterclockwise to approximately the 7 o'clock setting with almost no travel left, which may be a problem if the elbow needs to be bent downward, which it does not need to do. At this point, should the elbow joint then be positioned to its full 90 degrees of upward bend with the upper arm remaining at its maximum downward setting, cable attachment point 22z would then rotate clockwise within the sealed windlass, returning finally to the 10 o'clock setting. As has been stated previously, without the 340 degrees of rotation afforded by this sealed windlass arrangement as depicted 22g and if the assembly may work with only 180 degrees of cable rotation as are typically utilized in lower extremity positioners, no such 90 degrees of elbow bend would be possible.

Figure 23A:
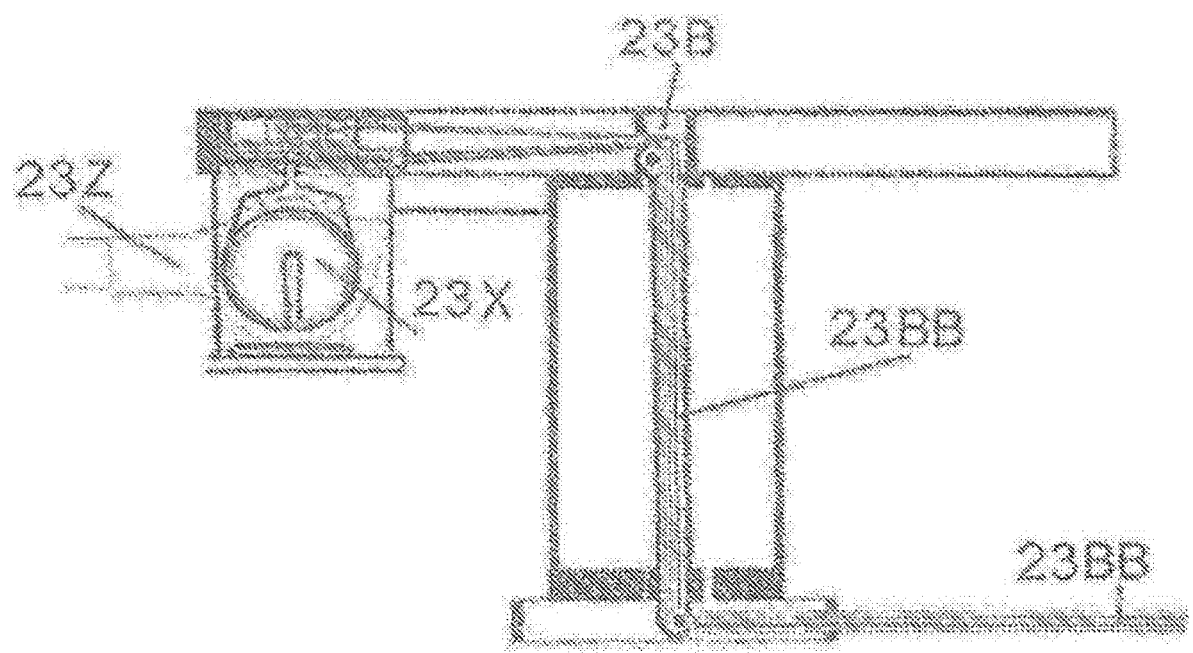
FIGS. 23A through 23D illustrate an exemplary anatomical positioner in use on an operating room table capable of Trendelenberg positioning, in accordance with an embodiment of the present invention.
Figure 23B:
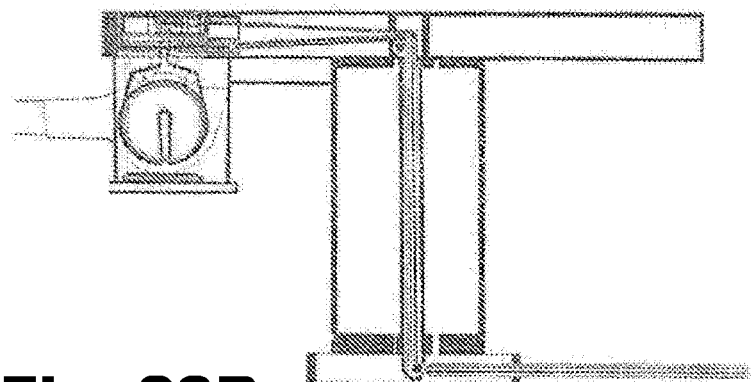
Figure 23C:
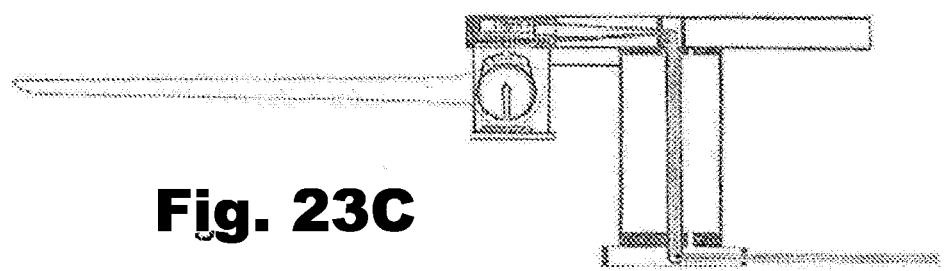
Figure 23D:
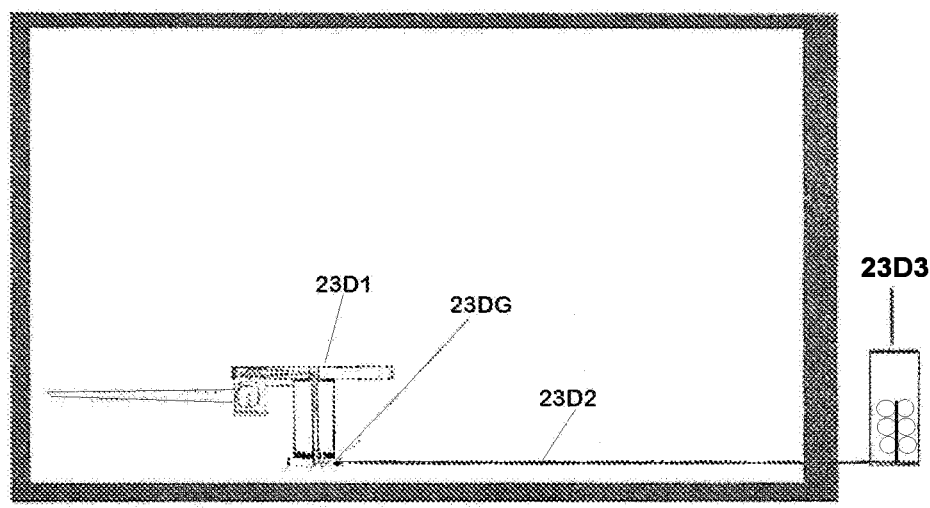

FIGS. 23A through 23D illustrate an exemplary anatomical positioner in use on an operating room table capable of Trendelenberg positioning, in accordance with an embodiment of the present invention. FIGS. 23A, 23B and 23C are diagrammatic side views, and FIG. 23D shows the table in a hybrid operating room. In the present embodiment, the table is fully nonmetallic. Referring to FIG. 23A, the placement of a center drive axel rod 15B equipped with an inline arrangement of free spinning pulley bearings is shown, such that control cables 15BB may ingress and egress thru center drive point over the free spinning pulleys on axel rod 15B thereby ingressing and egressing into a cable windlass 15x where rotation of windlass 15x results in vertical positioning of a positioning boom 15z. FIGS. 23B and 23C illustrate views of the entire table with leg positioners. Referring to FIG. 23D, control cables are housed in a protective covering and exit the hybrid operating room over axel rod 15g. An adjustable cable tensioner pulley rod keeps a steady pressure upon the control cables in order to generally eliminate unwanted slack from the control cables and to relieve tension slightly during Trenedelenberg tilt and Reverse Trenedelenberg tilt of the table top axis in order to not introduce stress to the inner mechanisms. This tension may be restored via the application of slight tension by cable tensioner axel rod 15g after table top positioning has been completed. A rudimentary arrangement of powered winches in a computer coordinated control console is located outside of the operating room, thereby allowing remote control of the entire nonmetallic table and all cable driven anatomic positioners, which may include, without limitation, remotely powered cable windlass iterations of upper and lower extremity positioners as well as head and neck positioners completely within a live imaging bore, and perhaps in pinpoint coordination with surgical robotics.

A computer coordinated and/or controlled embodiment of the present invention, may include hardware systems to enable electronically controlled and powered actuation of at least one of at least one primarily non-metallic anatomical positioner actuation cable. Some related embodiment may also be configured to include a remote actuation control system that is configured by conventional computer hardware and software to remotely actuate at least one of the primarily non-metallic cables in at least partial coordination with a surgical robotic and an image guidance system. Those skilled in the art will readily recognize, in light of the teachings of the present invention, a multiplicity of alternative means to implement machine powered controlled actuation of any of the various actuation cables of the present invention. For example, without limitation, instead of routing the various actuation cables externally to a remote controlled actuation module, an embodiment of the present invention may include actuation powered motors or pistons within the assemblies in any of the described or possible embodiments of the present invention. It is contemplated that any such internal machine controlled actuation means may be powered by any suitable power source depending on the actuator type, such as, without limitation, electricity, air pressure, hydraulic pressure, etc.

Figure 24:
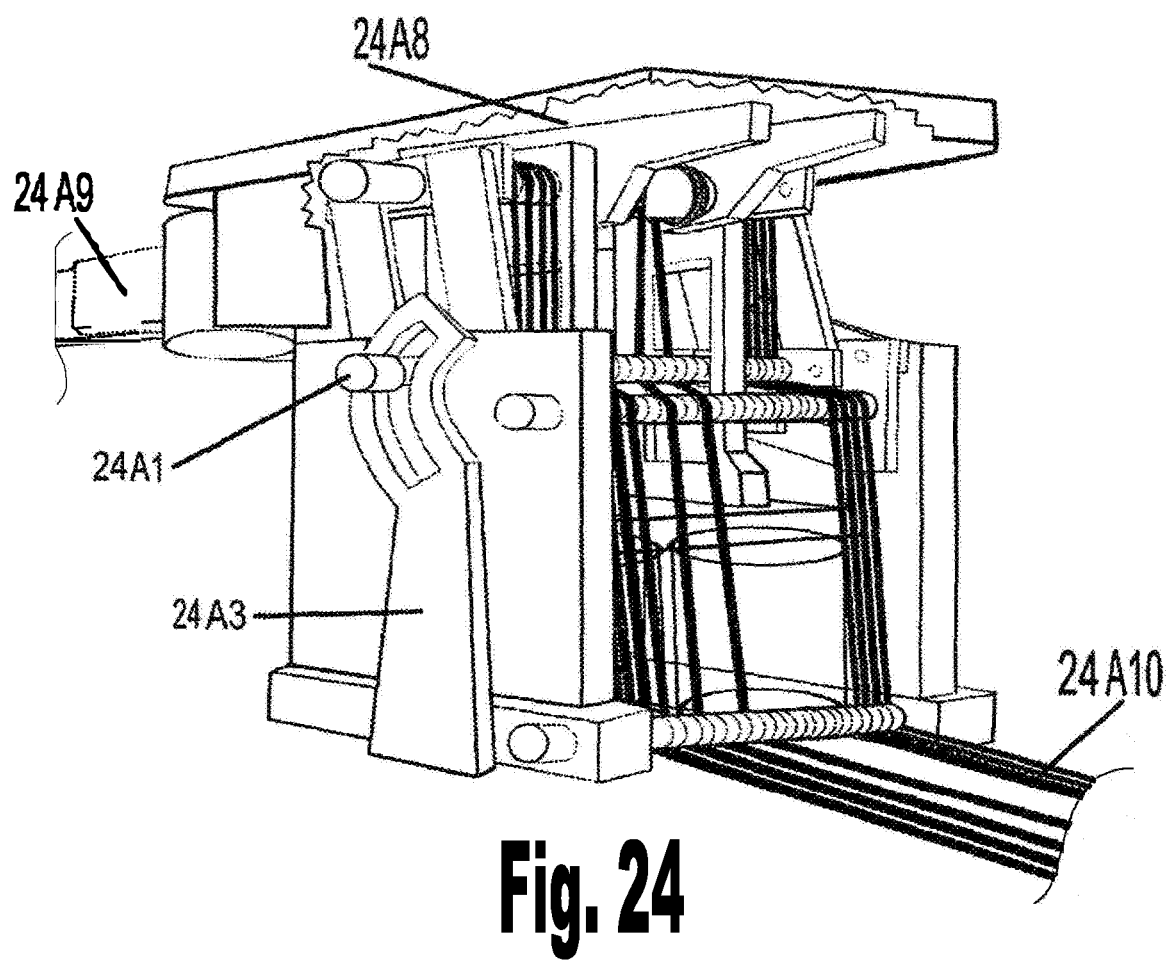
FIGS. 24A through 24I illustrate an exemplary remotely operated, nonmetallic, height adjustable Trendelenberg and reverse Trendelenberg imaging compatible operating table, in accordance with an embodiment of the present invention.

FIG. 24A illustrate an exemplary remotely operated, nonmetallic, height adjustable Trendelenberg and reverse Trendelenberg imaging compatible operating table, in accordance with an embodiment of the present invention. Referring to FIG. 24A, in the present embodiment, the table is shown with a cable windlass actuated lower extremity positioner for anterior approach hip arthroplasty. 16A 1=A Parallelogram Mounted Axel Rod. 16 A2=Parellogram which maintains cable length as Parallelogram mounted Axel Rod travels Vertically thru 16A3. 16A3=Axel Rod Guide (s). 16 A 4=Center Point Axel Rod. 16 AS=Fixed Point Axel Rod. 16 A 6=Lower Axel Rod. 16 A 7=Trendelenberg Chinese Windlass and Trendelenberg Tilt Mounts. 16 A 8=Table Top thru which travel CONTROL CABLES to Leg Positioner. 16A 9=Leg positioner. 16Al O=Control Cables.

FIG. 24B illustrates the same table shown with an inflatable airbag suspension (capable of 5000 lbs. of lift). 16AA 1=Inflatable Airbag Suspension System installed in the Table Base. 16AA 2=Table in a Low Vertical Adjustment Mode. 16AA 3=Table Positioned in a fully Extended Vertical Mode. 16AA4=Table Shown in a Reverse Trendelenberg Mode. 16AA5=Table Shown in a Trendelenberg Mode. This will more fully depict the positioning of the center drive cable w Axel Rod as SEEN FROM ABOVE . . . as well as displaying more fully the Remotely operated CABLE WINDLASS Actuation of said 100% Non Metallic Imaging Bore Compatible Table. The table is shown here being lifted via an inflatable airbag suspension from the automotive industry. In some practical embodiments, the automotive suspension bags may be employed to drive pistons to control a Trendelenberg and Reverse trendelenburg positioning of the table top. However, in some alternate embodiments, the table base may be raised and lowered via a multiplicity of suitable means such as, but not limited to, a series of Chinese cable windlasses, remotely actuated via offsite winches, a scissor lift, jacks, automotive suspension bag, etc.

FIGS. 24C thru 24G depict frame by frame height adjustment and Trendelenberg and Reverse Trenedelenberg Positioning of a fully nonmetallic imaging table with center drive cables able to raise and tilt without changing in total length via the interaction of the control cables thru a fixed entry point of a center point axel rod over a parallelogram mounted axel rod which maintains total cable length as it rotates thru fixed degrees of arc thru axel rod guides and then exits the parallelogram at another fixed point axel rod before said cables move downward to the lower axel rod to leave the imaging bore or hybrid operating room. The ability to relax the cables before height and tilt adjustments due to the actions of the cable tensioning axel rod generally aids in the adjustments of the table.

Figure 24I:
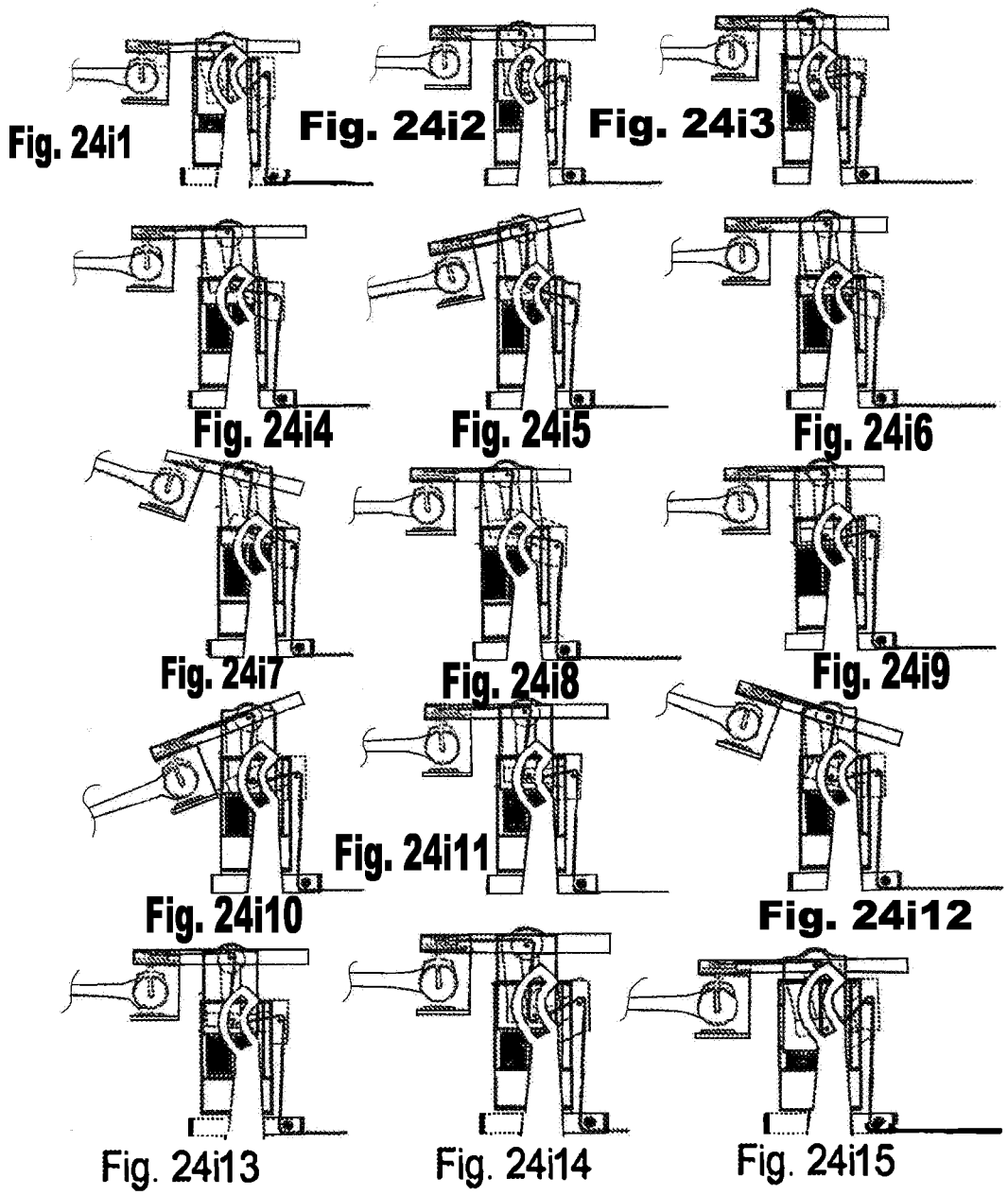

FIGS. 24H and 24I depict this table being raised and lowered via the inflation and deflation of an auto suspension air bag, as one exemplary embodiment for raising the table.

An alternate embodiment of the present invention comprises a hub assembly similar to those illustrated by way of example in the foregoing embodiments yet that use different mechanisms such as, but not limited to, axels, metal components, universal joints, etc. Another alternate embodiment may provide a leg positioner without automatic braking for traction and positioning or for rotation and angulation. Yet other alternate embodiments may comprise a control handle that uses a separate control for each movement.

FIG. 25 illustrates an exemplary embodiment of a lower extremity positioner configured as a modular device which can readily convert any operating room table into a platform for hip and knee surgical procedures, to include the anterior approach to hip arthroplasty. FIG. 25 1a. Illustrates a variable, adjustable width assembly which can attach the FIG. 24 lower extremity positioning modular device to operating table 1e, via interaction of FIG. 1d, a female slotted channel attached to the lower extremity module, connectable to 1e, a male side-rail attachment connected to the operating table 1c. FIG. 25 1b illustrates a height adjustable scissor lift, such that, through the action of scissor lift 1b and width assembly attachment 1a, the Leg Lower Extremity Positioner Module FIG. 25 may mount to operating table 1e.

FIG. 26a illustrates, an exemplary embodiment of the lower extremity positioning module. FIG. 26b illustrates the lower extremity module attached to an operating table.

FIG. 27A illustrates an exemplary embodiment of a hand actuated cable rotor operating table, utilizing the present invention in concert with a conventional height adjustable table in accordance with an embodiment of the present invention; 27A1 illustrates the nonmetallic portions of the operating table in accordance with an embodiments of the present invention; 27A2 illustrates the metallic conventional height adjustable table portion in accordance with an embodiment of the present invention; 27A3 illustrates the Height Adjustable and Trendelenberg Tilt components of the conventional metallic operating table FIG. 27B illustrates an exemplary embodiment of a hand actuated caliper rotor operating table, in accordance with an embodiment of the present invention; FIG. 27C illustrates a set of hand actuated caliper rotor upper extremity positioners in accordance with an embodiment of the present invention; FIG. 27D illustrates a hand actuated caliper rotor head and neck positioner in accordance with an embodiment of the present invention; FIG. 27E illustrates a set of hand actuated caliper rotor lower extremity positioners in accordance with an embodiment of the present invention;

FIG. 28 a illustrates, an exemplary embodiment of a conventional operating room table equipped with hybrid cable windlass/caliper rotor actuated free spinning winch iterations of the lower and upper extremity and head and neck positioners in a hand operated, automatic locking modality, with control cables connected to the caliper rotor actuated free spinning winches located in the table base.

Figure 28A:
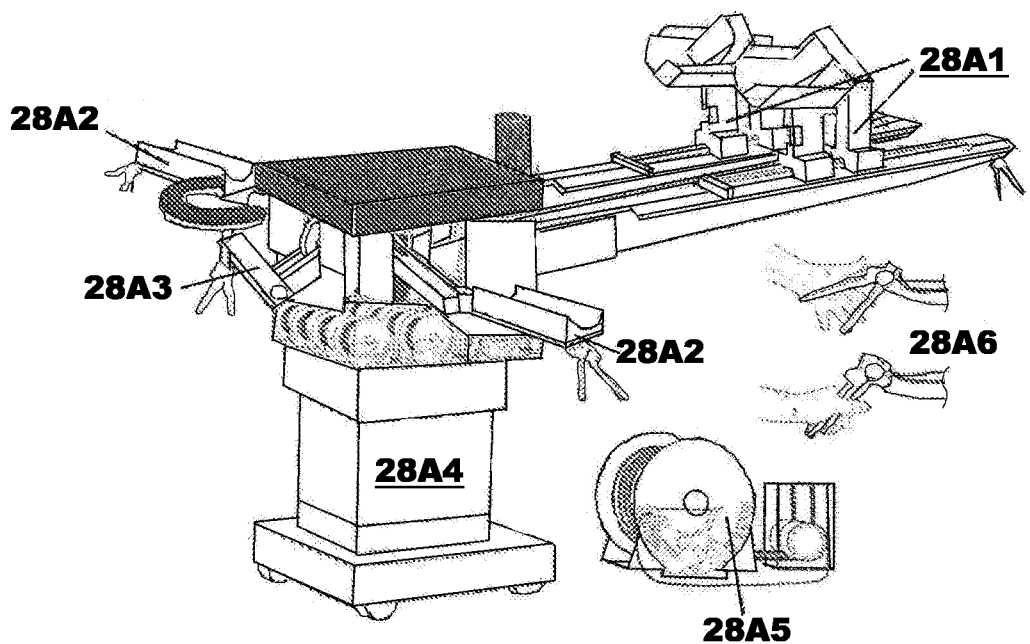
FIG. 28A a illustrates an exemplary embodiment of a hand actuated cable windlass/caliper rotor hybrid operating room table, in accordance with an embodiment of the present invention.

FIG. 28a1 illustrates the lower extremity positioners with hand actuation.

FIG. 28a2 illustrates the upper extremity positioners with hand actuation.

FIG. 28a3 illustrates the head and neck positioner with hand actuation.

FIG. 28a4 illustrates the caliper rotor actuated free spinning winches and spooling unspooling control cables, located inside of the conventional operating table.

FIG. 28a5 illustrates the free spinning control cable winch with caliper rotor actuation, with FIG. 28a6 illustrating the hand controls, with hands on control and automatic hands free locking.

FIG. 28b illustrates, an exemplary embodiment of a conventional operating room table equipped with hybrid cable windlass/caliper rotor actuated free spinning winch with transparent illustrations of all positioners.

FIG. 28c illustrates, an exemplary embodiment of a free spinning non metallic cable control winch with caliper rotor actuation.

Figure 29:
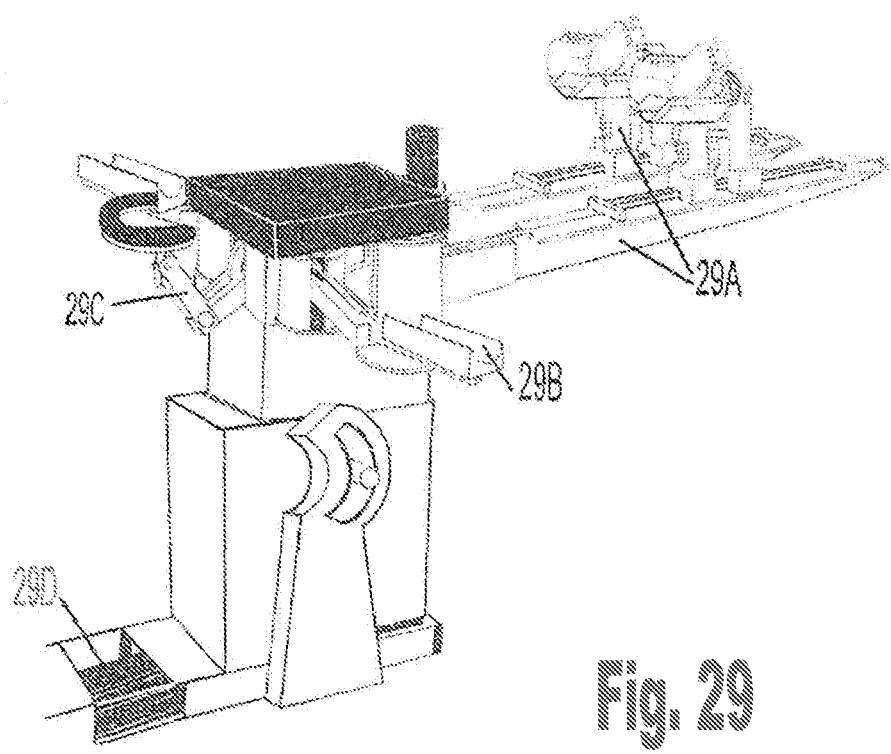
FIG. 29 illustrates an exemplary embodiment of a remote controlled cable windlass actuated primarily non-metallic set of head and neck, upper, and lower extremity positioners, with trendelenberg, reverse trendelenberg tilt and height adjustability in accordance with an embodiment of the present invention.

FIG. 29 illustrates, an exemplary embodiment of a fully non metallic, remotely controlled, operating table with variable xyz positioning and locking of the upper and lower extremities, the head and neck, height adjustability and Trendelenberg and reverse Trendelenberg positioning, for use within the imaging bore and hybrid operating rooms, either alone or in direct coordination with image guidance surgical systems and surgical robotics.

29a illustrates the cable windlass actuated non metallic lower extremity positioners.

29b illustrates the cable windlass actuated upper extremity positioners.

29c illustrates the cable windlass actuated head and neck positioner.

29d illustrates the ingress and egress of non metallic control cables.

FIG. 30, 30a illustrates, exemplary transparent views of the remotely operated non metallic height adjustable, Trendelenberg positionable operating table with cable windlass actuated lower and upper extremity, and head and neck positioners.

30a illustrates a transparent side view.

30b illustrates a partially transparent oblique view with non metallic control cables communicating thru an variable axel bearing rod assembly which maintains control cable length throughout variable positioning of the table.

30c depicts the remote control assembly with powered winches and spring reel/spirator counterbalances, the movements of which may or may not be coordinated via a computer program.

Figure 31:
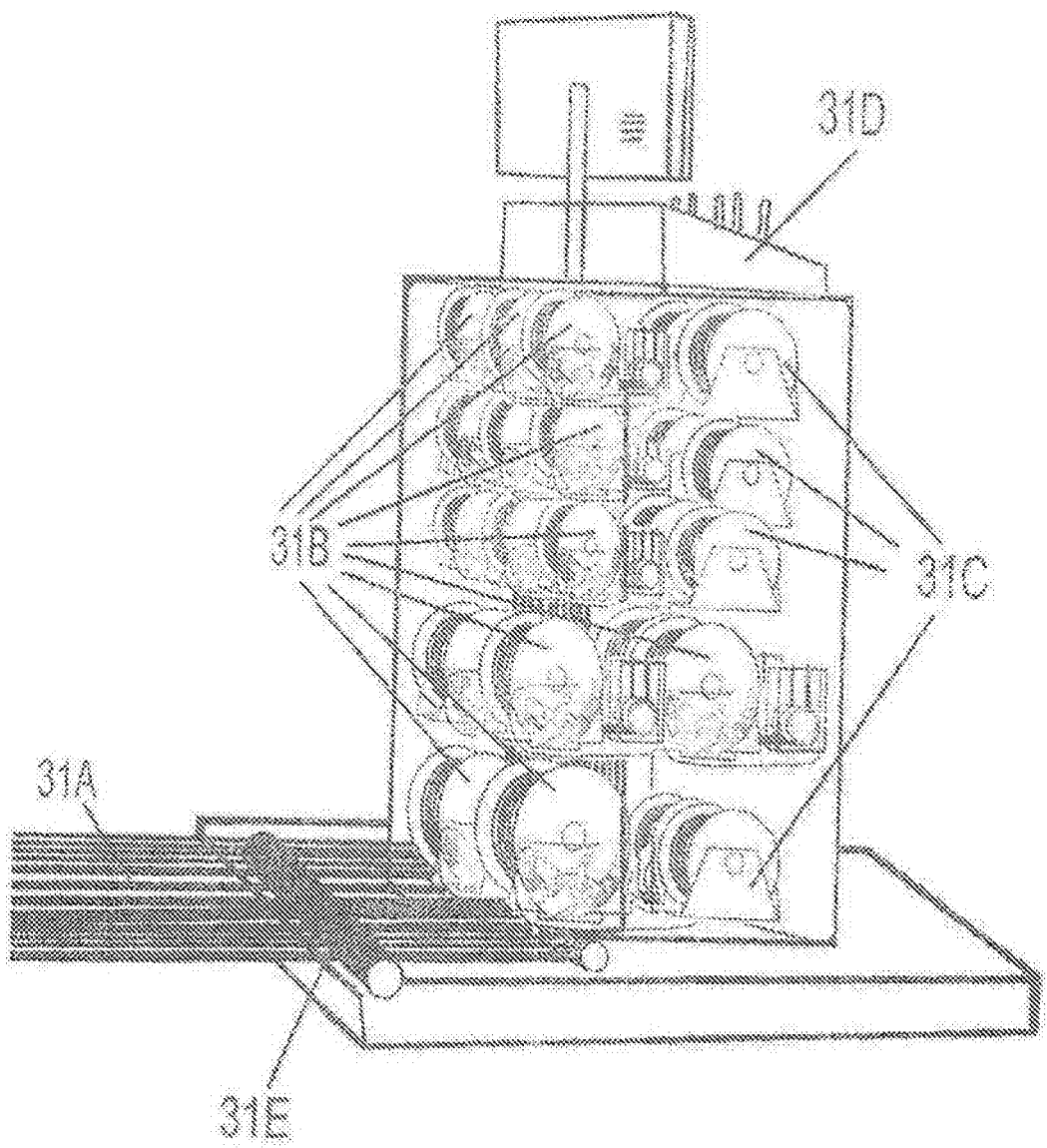
FIG. 31 illustrates an exemplary embodiment of a cable control assembly for the non metallic, remotely operable, height adjustable, Trendelenberg reverse Trendelenberg operating table with remotely operable upper, lower and head and neck positioning in accordance with an embodiment of the present invention.

FIG. 31 illustrates an exemplary embodiment of a cable control assembly for the non metallic, remotely operable, height adjustable, Trendelenberg reverse Trendelenberg operating table with remotely operable upper, lower and head and neck positioning.

31A illustrates the ingress and egress of the non metallic control cables into the assembly.

31B illustrates the powered winches which remotely actuate positioning of the table and the patient extremities.

31C illustrates the spring reel/spirators which use spring reeled cable to provide counterbalancing to the load end of the extremity positioners, for purposes of providing mechanical equilibrium. In alternative embodiments, non-metallic mechanical equilibrium may be achieved by attaching variable tension bands to the load ends of the fulcrum point on the extremity positioners, in the manner of weight lifting equipment, or by simply suspending weights from the load end of the positioners.

31D illustrates an exemplary control panel for the operation of the positioning of the table and the patient via control of the cable winches. This control of the winches may or may not be coordinated via a computer program combining loaded and realtime data from the imaging array, fiducials mounted to the table and the positioners which track exact location migration and positioning, and robotic movement, such that the table and positioners can interact seamlessly as one surgical tool during image guided and robotic surgeries, with pinpoint coordination of movement of the table and positioners within the array.

Figure 32A:
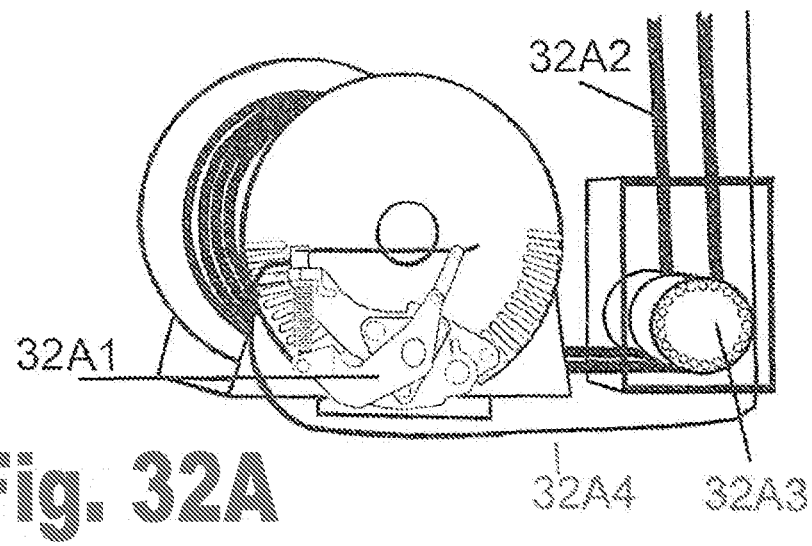
FIG. 32A illustrates an exemplary iteration of a powered cable control winch, in accordance with an embodiment of the present invention.

FIG. 32A illustrates an exemplary iteration of a powered cable 32A2 control winch 32A3 with a secondary caliper rotor added as a means 32A4 of automatic braking 31A1 under the loss of power to the winches.

Figure 32B:
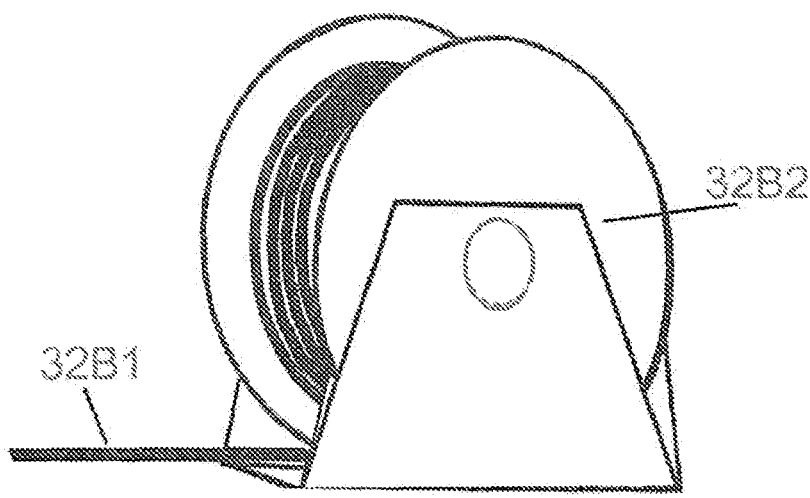
FIG. 32B illustrates an exemplary variable or fixed tension spring reel, in accordance with an embodiment of the present invention.

FIG. 32B illustrates a variable, or fixed tension spring reel 32B2, with cable pull 32B1 providing counterbalancing to the positioners at the load end of the fulcrum point.

Figure 33:
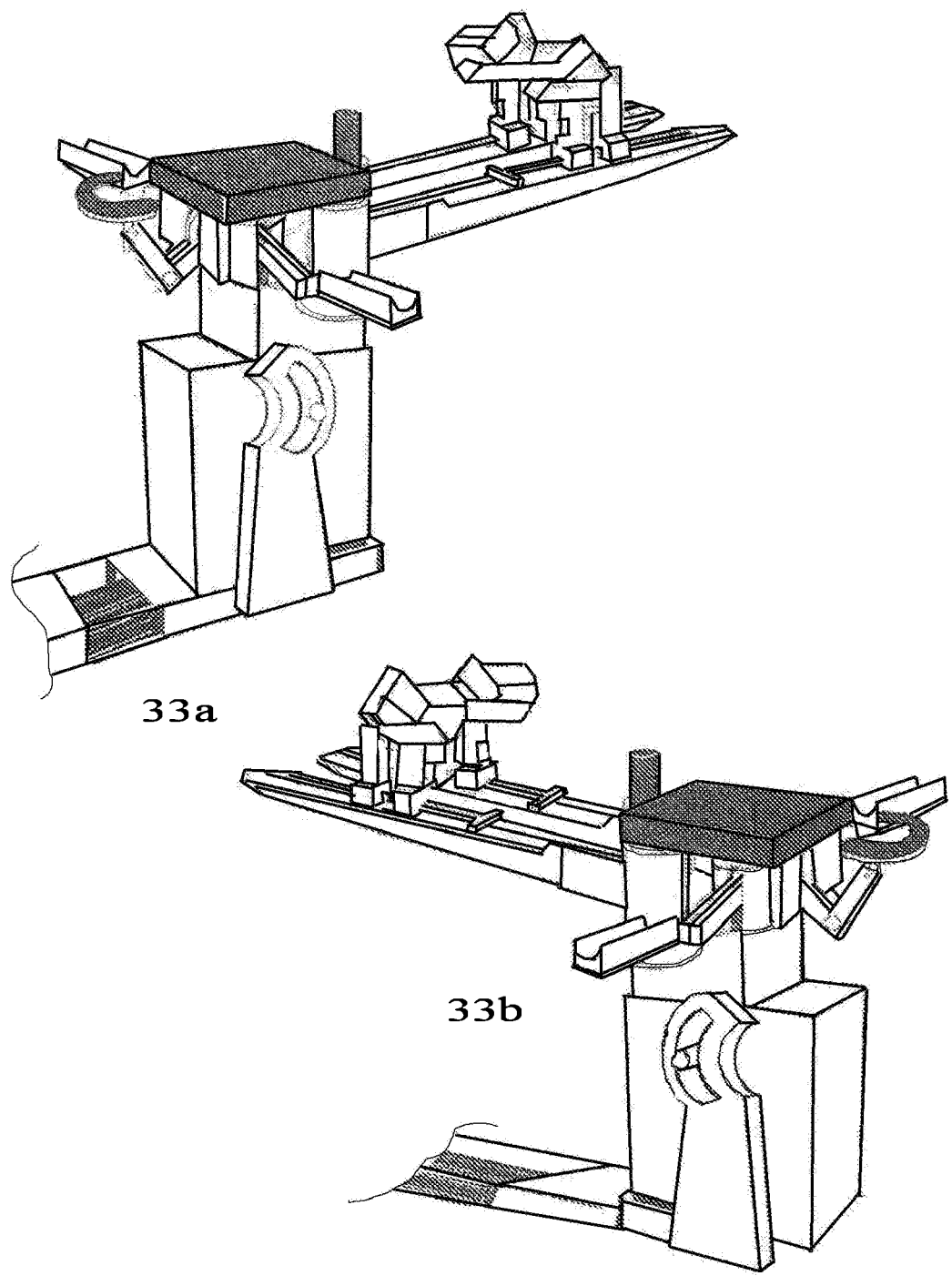
FIG. 33, illustrates exemplary views, 33A illustrating the cable control and counterbalance cables with egress from the head portion of the operating table and 33B illustrating the cable control and counterbalancing cables with egress from the foot portion of the operating table, of a remotely operated primarily non-metallic height adjustable, trendelenberg tilt, flexion extension operating table, in accordance with an embodiment of the present invention.

FIGS. 33a and b, illustrates exemplary views, FIG. 33 a from a right side perspective and FIG. 33b from a left side perspective, of a remotely operated primarily non-metallic height adjustable, operating table, in accordance with an embodiment of the present invention.

It is contemplated that some embodiments may employ various different means for providing one handed control with a finger tap for additional control. For example, without limitation, in one such embodiment, a head positioner may enable the elbow to be locked by moving the entire unit with one hand. Then, an extra lever or trigger may enable the user to tap this lever with one finger to provide finger controlled fine tuning of the positioner in one or more directions of travel. Some embodiments may employ tension bands for braking.

In the exemplary embodiments, the methods and apparatus disclosed are fashioned and constructed either with no metal components or with minimal metal components in order to optimize interaction with the imaging array and evolving hybrid or paradigm, necessitating not only the usage of carbon fiber, synthetics and polymers, but also necessitating a means of design and construction that enables said components to be functional. As such, it is contemplated that some practical embodiments of the present embodiment may comprise not only nonmetallic and substantially nonmetallic means of construction and implementation, but also may implement these methods and apparatuses as constructed using various different types of metal, in that the methods function with equal validity and utility in both the nonmetallic and the metallic iterations. The methods and apparatuses disclosed in the foregoing represent improvements with respect to the nonmetallic imaging environment and also achieve exceptional functionality regardless of composition. While not ideal, in many practical embodiments having various degrees of utility as required by the needs of the particular application, those skilled in the art will readily recognize that any, or all, of the foregoing non-metallic components of the present invention may be replaced with substantially non-metallic, primarily non-metallic, or even mostly metallic, counterpart components having potential corresponding degradation of the radiolucent aspect of substantially non-metallic versions, which in some applications may be acceptable in light benefitting from the many other novel utilities provided by various other aspects of the present invention.

Those skilled in the art will readily recognize, in light of and in accordance with the teachings of the present invention, that any of the foregoing steps may be suitably replaced, reordered, removed and additional steps may be inserted depending upon the needs of the particular application. Moreover, the prescribed method steps of the foregoing embodiments may be implemented using any physical and/or hardware system that those skilled in the art will readily know is suitable in light of the foregoing teachings. For any method steps described in the present application that can be carried out on a computing machine, a typical computer system can, when appropriately configured or designed, serve as a computer system in which those aspects of the invention may be embodied.

All the features disclosed in this specification, including any accompanying abstract and drawings, may be replaced by alternative features serving the same, equivalent or similar purpose, unless expressly stated otherwise. Thus, unless expressly stated otherwise, each feature disclosed is one example only of a generic series of equivalent or similar features.

It is noted that according to USA law 35 USC § 112 (1), all claims must be supported by sufficient disclosure in the present patent specification, and any material known to those skilled in the art need not be explicitly disclosed. However, 35 USC § 112 (6) requires that structures corresponding to functional limitations interpreted under 35 USC § 112 (6) must be explicitly disclosed in the patent specification. Moreover, the USPTO's Examination policy of initially treating and searching prior art under the broadest interpretation of a "mean for" claim limitation implies that the broadest initial search on 112(6) functional limitation would have to be conducted to support a legally valid Examination on that USPTO policy for broadest interpretation of "mean for" claims. Accordingly, the USPTO will have discovered a multiplicity of prior art documents including disclosure of specific structures and elements which are suitable to act as corresponding structures to satisfy all functional limitations in the below claims that are interpreted under 35 USC § 112 (6) when such corresponding structures are not explicitly disclosed in the foregoing patent specification. Therefore, for any invention element(s)/structure(s) corresponding to functional claim limitation(s), in the below claims interpreted under 35 USC § 112 (6), which is/are not explicitly disclosed in the foregoing patent specification, yet do exist in the patent and/or non-patent documents found during the course of USPTO searching, Applicant(s) incorporate all such functionally corresponding structures and related enabling material herein by reference for the purpose of providing explicit structures that implement the functional means claimed. Applicant(s) request(s) that fact finders during any claims construction proceedings and/or examination of patent allowability properly identify and incorporate only the portions of each of these documents discovered during the broadest interpretation search of 35 USC § 112 (6) limitation, which exist in at least one of the patent and/or non-patent documents found during the course of normal USPTO searching and or supplied to the USPTO during prosecution. Applicant(s) also incorporate by reference the bibliographic citation information to identify all such documents comprising functionally corresponding structures and related enabling material as listed in any PTO Form-892 or likewise any information disclosure statements (IDS) entered into the present patent application by the USPTO or Applicant(s) or any $3^{rd}$ parties. Applicant(s) also reserve its right to later amend the present application to explicitly include citations to such documents and/or explicitly include the functionally corresponding structures which were incorporate by reference above.

Thus, for any invention element(s)/structure(s) corresponding to functional claim limitation(s), in the below claims, that are interpreted under 35 USC § 112 (6), which is/are not explicitly disclosed in the foregoing patent specification, Applicant(s) have explicitly prescribed which documents and material to include the otherwise missing disclosure, and have prescribed exactly which portions of such patent and/or non-patent documents should be incorporated by such reference for the purpose of satisfying the disclosure requirements of 35 USC § 112 (6). Applicant(s) note that all the identified documents above which are incorporated by reference to satisfy 35 USC § 112 (6) necessarily have a filing and/or publication date prior to that of the instant application, and thus are valid prior documents to incorporated by reference in the instant application.

Having fully described at least one embodiment of the present invention, other equivalent or alternative methods of implementing a non-metallic, articulating patient positioning system according to the present invention will be apparent to those skilled in the art. Various aspects of the invention have been described above by way of illustration, and the specific embodiments disclosed are not intended to limit the invention to the particular forms disclosed. The particular implementation of the non-metallic, articulating patient positioning system may vary depending upon the particular context or application. By way of example, and not limitation, the non-metallic, articulating patient positioning systems described in the foregoing were principally directed to nonmetallic implementations; however, similar techniques may instead be applied to implementations in which a small amount or large amount of metal material may be used, which implementations of the present invention are contemplated as within the scope of the present invention. The invention is thus to cover all modifications, equivalents, and alternatives falling within the spirit and scope of the following claims. It is to be further understood that not all of the disclosed embodiments in the foregoing specification will necessarily satisfy or achieve each of the objects, advantages, or improvements described in the foregoing specification.

Claim elements and steps herein may have been numbered and/or lettered solely as an aid in readability and understanding. Any such numbering and lettering in itself is not intended to and should not be taken to indicate the ordering of elements and/or steps in the claims.

The corresponding structures, materials, acts, and equivalents of all means or step plus function elements in the claims below are intended to include any structure, material, or act for performing the function in combination with other claimed elements as specifically claimed.

The Abstract is provided to comply with 37 C.F.R. Section 1.72(b) requiring an abstract that will allow the reader to ascertain the nature and gist of the technical disclosure. It is submitted with the understanding that it will not be used to limit or interpret the scope or meaning of the claims. The following claims are hereby incorporated into the detailed description, with each claim standing on its own as a separate embodiment.

The invention claimed is:

1. An apparatus comprising:
an elongated anatomical support member;
two buttressing members, wherein the two buttressing members and
the elongated anatomical support member comprise at least one layer of laminar sheeting, and wherein said two buttressing members are engaged with respective sides of said elongated anatomical support member, and wherein said two buttressing members are further configured to resist lateral flexing of at least a portion of said elongated anatomical support member and such that normal anatomic loading forces in the direction of gravity put upon said elongated anatomical support member are not transmitted to said two buttressing members, and in which said resisting of lateral flexing of said elongated anatomical support member is perpendicular to the plane formed by said at least one layer of laminar sheeting;
a radiolucent rotatable joint formed by engaging said two buttressing members and said elongated anatomical support member with turntable bearings and two lateral supports thereby providing a fixed axis for rotation of the said elongated anatomical support member in the plane formed by said at least one layer of laminar sheeting of said elongated anatomical support member; and,
at least a portion of said at least one layer of laminar sheeting of said elongated anatomical support member proximal to said fixed axis is configured to be perpendicular to said fixed axis, parallel to said two buttressing members, and at least a portion of said at least one layer of laminar sheeting and said two buttressing members are formed of material that do not cause imaging artifacts when medically imaged, and in which said portion of said at least one layer of laminar sheeting of said radiolucent rotatable joint is configured to engage with said turntable bearings thereby forming a buttressed rotatable joint.

2. The apparatus of claim 1, further comprising a radiolucent turntable hub assembly connected to said buttressed rotatable joint via a connector, wherein said connector is formed of material(s) that does not cause imaging artifacts when medically imaged, wherein said radiolucent turntable hub assembly is configured to rotate in a plane perpendicular to the plane of rotation of the radiolucent rotatable joint so as to allow the elongated anatomical support member be positionable in vertical and horizontal orientations without offsets between its x, y, and z axes.

3. The apparatus as recited in claim 2, further comprising at least one radiolucent cable windlass in engagement with said anatomical support member for positioning said radiolucent rotatable joint, wherein said at least one radiolucent cable windlass comprises at least one layer of laminar sheeting of radiolucent material in and engages with a radiolucent cable, and said at least one radiolucent cable windlass further comprising a caliper rotor, said caliper rotor being configured to actuate said elongated anatomical support member.

4. The apparatus as recited in claim 3, further comprising a remote actuation control system configured to remotely actuate said radiolucent cable, wherein the remote actuation control system is in coordination with a surgical robotic and an image guidance system.

5. The apparatus as recited in claim 2, further comprising a radiolucent head positioner being configured for selective position both vertically and horizontally.

6. The apparatus as recited in claim 2, further comprising:
a extremity support assembly to provide support for one of an ankle, a hand, and a head, said extremity support assembly located at a distal portion of said anatomical support member;
means for controlling tilt of said extremity support assembly; and
means for locking a position of said extremity support assembly.

7. The apparatus as recited in claim 2, further comprising:
a joint assembly operable to support an upper extremity, a lower extremity, and/or a head and neck, said joint assembly being further configured with
means for selective angulation of said joint assembly; and
means for locking a position of said joint assembly.

8. The apparatus as recited in claim 1, in which a portion of said elongated anatomical support member that is buttressed with said two buttressing members is configured to be proximal to said turntable bearings, and in which a portion of said two buttressing members is comprised of material that does not cause imaging artifacts when medically imaged.

9. The apparatus as recited in claim 1, in which a portion of said turntable bearings is comprised of material that does not cause imaging artifacts when medically imaged.

10. The apparatus as recited in claim 1, in which said buttressed rotatable joint is coupled to a patient care platform, the patient care platform having an upper torso support portion and a lower torso support portion, said buttressed rotatable joint being coupled with at least one of the upper and lower torso support portions to enable angular articulation thereof.

11. The apparatus as recited in claim 1, further comprising at least one anatomic supporting member engaged with said elongated anatomical support member, that enables extended variable angular articulation.

12. The apparatus of claim 1, further comprising:
a plurality of cable windlasses, each comprising at least one layer of laminar sheeting of radiolucent material;
at least one winch in engagement with a radiolucent cable for spooling said radiolucent cable, in which said at least one winch is located within a hub; and
in which said at least one winch is controllable remotely and in which said at least one winch further comprises a rotor mechanism configured to at least enable vertical travel of said elongated anatomical support member, and in which, said rotor travels through a caliper, said rotor mechanism and caliper being configured such that when said caliper is released, a horizontal caliper is released, which intermeshes with a horizontal rotor such that said elongated anatomical support member thru the rotation of said at least one windlass located in said hub rotates, and at least one spring reel counterbalances said at least one elongated anatomical support member.

13. A system comprising:

an elongated anatomical support member;

two buttressing members, wherein the buttressing members and the elongated anatomical support member comprise at least one layer of laminar sheeting, and wherein said two buttressing members are engaged with respective sides of said elongated anatomical support member, and wherein said buttressing members are further configured to resist lateral flexing of at least a portion of said elongated anatomical support member on the sides where said buttressing members are engaged with said elongated anatomical support member such that normal anatomic loading forces in the direction of gravity put upon said elongated anatomical support member are not transmitted to said two buttressing members, and in which aid resisting of lateral flexing of said elongated anatomical support member is perpendicular to the plane formed by said at least one layer of laminar sheeting of said elongated anatomical support member;

a radiolucent rotatable joint formed by engagement of said two buttressing members and said elongated anatomical support member with turntable bearings and two lateral supports that provides a fixed axis for rotation of the said elongated anatomical support member in the plane formed by said at least one layer of laminar sheeting of said elongated anatomical support member;

a portion of said at least one layer of laminar sheeting of said elongated anatomical support member proximal to said fixed axis is perpendicular to said fixed axis, and at least a portion of said at least one layer of laminar sheeting and said two buttressing members are substantially artifact-free and formed of material that does not cause imaging artifacts when medically imaged, and in which said portion is configured to engage with said turntable bearings thereby forming a buttressed rotatable joint;

a patient care platform, in which the buttressed rotatable joint is structurally integrated with a central structural member of said patient care platform, which central structural member is a main load bearing member; and at least one load supporting member, said at least one load supporting member being engaged with said buttressed rotatable joint to enable variable angular articulation.

* * * * *